United States Patent [19]

Andrew et al.

[11] Patent Number: 5,280,027
[45] Date of Patent: Jan. 18, 1994

[54] ANTI-TUMOR COMPOUNDS

[75] Inventors: Robert G. Andrew; Andrew J. Barker, both of Macclesfield; Francis T. Boyle, Congleton; James M. Wardleworth, Macclesfield, all of England

[73] Assignees: Imperial Chemical Industries PLC; National Research Development Corporation, London, England

[21] Appl. No.: 708,046

[22] Filed: May 30, 1991

[30] Foreign Application Priority Data

May 30, 1990 [GB] United Kingdom .................. 9011989

[51] Int. Cl.$^5$ .................. C07D 239/96; C07D 239/95; C07D 239/90; A61K 31/505
[52] U.S. Cl. .................................. 514/259; 514/260; 544/284; 544/285; 544/287
[58] Field of Search ...................... 544/285, 287, 284; 514/259, 260

[56] References Cited

U.S. PATENT DOCUMENTS

| 4,447,608 | 5/1984 | Jones et al. ........................ 544/287 |
| 4,857,530 | 8/1989 | Berman et al. ..................... 514/259 |
| 4,981,856 | 1/1991 | Hughes .............................. 514/259 |
| 4,985,441 | 1/1991 | Hughes et al. ..................... 514/260 |
| 4,992,550 | 2/1991 | Hughes ............................. 544/284 |

FOREIGN PATENT DOCUMENTS

| 0284338 | 9/1988 | European Pat. Off. . |
| 0365763 | 5/1990 | European Pat. Off. . |
| 1021196 | 3/1966 | U.S.S.R. . |
| 2188319 | 9/1987 | United Kingdom . |
| 2227016 | 7/1990 | United Kingdom . |

OTHER PUBLICATIONS

Fessenden et al. "Organic Chemistry" 2nd Ed. pp. 714–721 (1982) Willard Press.

Primary Examiner—Mukund J. Shah
Assistant Examiner—Matthew V. Grumbling
Attorney, Agent, or Firm—Cushman, Darby & Cushman

[57] ABSTRACT

The invention relates to quinazoline derivatives, or pharmaceutically-acceptable salts thereof, which possess anti-tumour activity; to processes for their manufacture; and to pharmaceutical compositions containing them.

The invention provides a quinazoline of the formula:

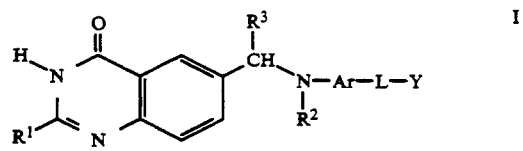

wherein
$R^1$ includes hydrogen, amino and alkyl or alkoxy each of up to 4 carbon atoms;
$R^2$ includes hydrogen, alkyl, hydroxyalkyl and halogenoalkyl each of up to 4 carbon atoms;
$R^3$ is hydrogen or alkyl or up to 3 carbon atoms;
Ar is phenylene or heterocyclene;
L is a group of the formula —CO.NH—, —NH.CO—, —CO.NR$^4$—, —NR$^4$.CO—, —CH=CH— or —CO.O—, wherein R$^4$ is alkyl of up to 4 carbon atoms; and Y is a branched alkyl group bearing substituents Y$^2$ and Y$^3$ the definition of each independently including hydroxy, cyano, aryl and heteroaryl, and the definition of Y$^3$ also optionally including sulpho, N-phenylsulphonylcarbamoyl and 5-tetrazolyl; or a pharmaceutically-acceptable salt thereof.

10 Claims, No Drawings

ANTI-TUMOR COMPOUNDS

This invention relates to novel anti-tumour compounds and more particularly it relates to quinazoline derivatives, or pharmaceutically-acceptable salts thereof, which possess anti-tumour activity. The invention includes novel quinazoline derivatives and processes for their manufacture; novel pharmaceutical compositions containing said quinazoline derivatives and the use of said quinazoline derivatives in the manufacture of novel medicaments for use in the production of an anti-tumour effect in a warm-blooded animal such as man.

One group of anti-tumour compounds comprises the antimetabolites, such as aminopterin and methotrexate, which are inhibitors of enzymes which utilise folic acid derivatives. A newer compound of this type which showed considerable promise in clinical trials is known as CB3717 and is described and claimed in United Kingdom Patent Specification No. 2065653B. Despite its promising activity against human breast, ovarian and liver cancer however, CB3717 shows symptoms of toxicity in humans, particularly in relation to the liver and kidney [Calvert, Alison, Harland, Robinson, Jackman, Jones, Newell, Siddik, Whiltshaw, McElwain, Smith and Harrap, *J. Clin. Oncol.*, 1986, 4, 1245; Cantwell, Earnshaw and Harris, *Cancer Treatment Reports*, 1986, 70, 1335; Bassendine, Curtin, Loose, Harris and James, *J. Hepatol.*, 1987, 4, 39; Vest, Bork and Hasen, *Eur. J. Cancer Clin. Oncol.*, 1988, 24, 201; Cantwell, Macaulay, Harris, Kaye, Smith, Milsted and Calvert, *Eur. J. Cancer Clin. Oncol.*, 1988, 24, 733; Sessa, Zucchetti, Ginier, Willems, D'Incalci and Cavalli, *Eur. J. Cancer Clin. Oncol.*, 1988, 24, 769].

Compounds of the CB3717-type are believed to act as anti-tumour agents by inhibiting the enzyme thymidylate synthase, which enzyme catalyses the methylation of deoxyuridine monophosphate to produce thymidine monophosphate which is required for DNA synthesis. The anti-tumour activity of CB3717 may be assessed in vitro by determining its inhibitory effect on that enzyme, and in cell cultures by its inhibitory effect on cancer cell lines such as the mouse leukaemia cell line L1210, the mouse lymphoma cell line L5178Y TK-/- and the human breast cancer cell line MCF-7.

Other compounds of the CB3717-type may therefore have their anti-tumour activity assessed and compared with that of CB3717 by their activity against, for example, the same enzyme and the same cancer cell lines.

Antimetabolites, such as aminopterin and methotrexate, which are inhibitors of enzymes which utilise folic acid derivatives, have also shown promise in the treatment of various allergic diseases such as allergic rhinitis, atopic dermatitis and psoriasis. The quinazoline derivatives of the present invention, being antimetabolites, are thus of value as therapeutic agents in the treatment of, for example, allergic conditions such as psoriasis.

European Patent Application No. 0316657 (published May 24, 1989) discloses a series of quinazoline derivatives which lack the amino acid residue of compounds of the CB3717-type. The disclosed compounds are reported to possess inhibitory activity against thymidylate synthase. Among the disclosed compounds are quinazoline derivatives wherein the amino acid residue of compounds of the CB3717-type is replaced by a residue derived from 5-aminotetrazole.

It is also known from European Patent Application No. 0365763 (published May 2, 1990) that quinazoline derivatives of, for example, the CB3717-type, but wherein the amino acid residue, has been replaced by, for example, a halogeno, cyano or phenylsulphonyl residue, retain activity against thymidylate synthase and the L1210 cell-line.

We have now found that the quinazoline derivatives of the present invention possess CB3717-type activity.

According to the invention there is provided a quinazoline of the formula I (set out hereinafter)

wherein $R^1$ is hydrogen or amino, or alkyl or alkoxy each of up to 4 carbon atoms;

or $R^1$ is alkyl of up to 3 carbon atoms which bears a hydroxy substituent, or which bears one, two or three fluoro substituents;

or $R^1$ is hydroxyalkoxy of up to 3 carbon atoms or alkoxyalkoxy of up to 4 carbon atoms;

wherein the quninazoline ring may bear no further substituent or may bear one further substituent selected from halogeno and from alkyl and alkoxy each of up to 3 carbon atoms;

wherein $R^2$ is hydrogen, alkyl, alkenyl, alkynyl, hydroxyalkyl, halogenoalkyl or cyanoalkyl each of up to 4 carbon atoms;

wherein $R^3$ is hydrogen or alkyl of up to 3 carbon atoms;

wherein Ar is phenylene or heterocyclene which may be unsubstituted or may bear one or two substituents selected from halogeno, hydroxy, amino and nitro, and from alkyl, alkoxy and halogenoalkyl each of up to 3 carbon atoms;

wherein L is a group of the formula —CO.NH—, —NH.CO—, —CO.NR$^4$—, —NR$^4$.CO—, —CH=CH— or —CO.O—, wherein $R^4$ is alkyl of up to 4 carbon atoms;

and wherein Y is a group of the formula

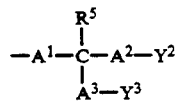

in which $R^5$ is hydrogen or alkyl of up to 3 carbon atoms;

$A^1$ is a direct link or is alkylene of up to 4 carbon atoms, $A^2$ is a direct link to $Y^2$ or is alkylene of up to 4 carbon atoms, $A^3$ is a direct link to $Y^3$ or is alkylene of up to 4 carbon atoms wherein optionally a constituent methylene group is replaced by an oxy, thio, sulphinyl, sulphonyl, imino or hydroxymethylene group;

$Y^2$ is hydroxy, amino, cyano, halogeno or trifluoroacetyl, or alkoxy, alkylamino, dialkylamino, halogenoalkyl, alkylthio, alkylsulphinyl, alkylsulphonyl, alkanoyloxy, alkanoyl or hydroxyalkanoyl each of up to 4 carbon atoms, or aryl, arylthio, arylsulphinyl or arylsulphonyl each of up to 10 carbon atoms, or heteroaryl, heteroarylthio, heteroarylsulphinyl or heteroarylsulphonyl;

and $Y^3$ has any of the meanings defined above for $Y^2$, or in addition $Y^3$ is sulpho, N-hydroxycarbamoyl, N-cyanocarbamoyl, carbazoyl or sulphamoyl, or N-alkylsulphamoyl, N,N-dialkylsulphamoyl, N-acylsulphamoyl, N-alkylcarbamoyl, N,N-dialkylcarbamoyl, N-alkylcarbamoyloxy, N,N-dialkylcarbamoyloxy or N-alkylsulphonylcarbamoyl each of up to 4 carbon atoms, N-phenylsulphonylcarbamoyl or 5-tetrazolyl;

and wherein each of said aryl, arylthio, arylsulphinyl, arylsulphonyl, heteroaryl, heteroarylthio, heteroarylsulphinyl or heteroarylsulphonyl groups may be unsubstituted or may bear one or two substituents selected from hydroxy, oxo, thioxo, amino, nitro, cyano, carbamoyl and halogeno, from alkyl, N-alkylcarbamoyl, N,N-dialkylcarbamoyl, alkylthio, alkylsulphinyl, alkylsulphonyl, alkoxy and halogenoalkyl each of up to 4 carbon atoms, and from phenyl and phenylalkyl of up to 10 carbon atoms;

and wherein said phenyl and phenylalkyl substituents or said N-phenylsulphonylcarbamoyl group may bear a substituent selected from nitro, cyano and halogeno and from alkyl and alkoxy each of up to 3 carbon atoms;

or a pharmaceutically-acceptable salt thereof;

provided that, in the group of the formula -L-Y, no constituent methylene or methine group is attached to more than one heteroatom which is not in a heteroaryl ring.

The chemical formulae referred to herein by Roman numerals are set out for convenience on a separate sheet hereinafter. In this specification the term "alkyl" includes both straight and branched chain alkyl groups but references to individual alkyl groups such as "propyl" are specific for the straight chain version only. An analogous convention applies to other generic terms.

It will be observed that a quinazoline of the invention may possess one or more asymmetric carbon atoms and it can therefore exist in racemic and optically active forms. It is to be understood that this invention encompasses a racemic form of the quinazoline and any optically-active form thereof which possesses anti-tumour activity, it being a matter of common general knowledge how a racemic compound may be separated into its optically-active forms.

It will also be observed that a quinazoline of the invention of the formula stated above wherein L is a group of the formula —CH=CH— may exist as two geometric isomers. It is to be understood that this invention encompasses any geometric isomer which possesses anti-tumour activity, it being a matter of common general knowledge how geometric isomers may be separated.

Within the present invention it is to be understood that a quinazoline of the formula I may exhibit the phenomenon of tautomerism and that the formulae drawings presented within this specification can represent only one of the possible tautomeric forms. It is to be understood that the invention encompasses any tautomeric form which possesses anti-tumour activity and is not to be limited merely to any one tautomeric form utilised within the formulae drawings.

It is also to be understood that certain quinazolines of the formula I can exist in solvated as well as unsolvated forms such as, for example, hydrated forms. It is to be understood that the invention encompasses all such solvated forms which possess anti-tumour activity.

Suitable values for the generic radicals referred to above include those set out below.

A suitable value for $R^1$, $R^2$ or $R^4$ when it is alkyl of up to 4 carbon atoms, or for an alkyl substituent of up to 4 carbon atoms which may be present as a substituent on an aryl, arylthio, arylsulphinyl, arylsulphonyl, heteroaryl, heteroarylthio, heteroarylsulphinyl or heteroarylsulphonyl group is, for example, methyl, ethyl, propyl, isopropyl, butyl, isobutyl, sec-butyl or tert-butyl.

A suitable value for $R^3$ or $R^5$ when it is alkyl of up to 3 carbon atoms, or for an alkyl substituent of up to 3 carbon atoms which may be present as a further substituent on the quinazoline ring, as a substituent on Ar, or as a substituent on a phenyl or phenylalkyl substituent or on a N-phenylsulphonylcarbamoyl group is, for example, methyl, ethyl, propyl or isopropyl.

A suitable value for $R^2$ when it is alkenyl is, for example, prop-2-enyl, but-2-enyl, but-3-enyl or 2-methylprop-2-enyl.

A suitable value for $R^2$ when it is alkynyl is, for example, prop-2-ynyl or but-3-ynyl.

A suitable value for $R^1$, $Y^2$ or $Y^3$ when it is alkoxy of up to 4 carbon atoms, or for an alkoxy substituent of up to 4 carbon atoms which may be present as a substituent on an aryl, arylthio, arylsulphinyl, arylsulphonyl, heteroaryl, heteroarylthio, heteroarylsulphinyl or heteroarylsulphonyl group is, for example, methoxy, ethoxy, propoxy, isopropoxy, butoxy, isobutoxy or tert-butoxy.

A suitable value for an alkoxy substituent of up to 3 carbon atoms which may be present as a further substituent on the quinazoline ring, as a substituent on Ar, or as a substituent on a phenyl or phenylalkyl substituent or on a N-phenylsulphonylcarbamoyl group is, for example, methoxy, ethoxy, propoxy or isopropoxy.

A suitable value for $Y^2$ or $Y^3$ when it is alkylthio of up to 4 carbon atoms, or for an alkylthio substituent of up to 4 carbon atoms which may be present as a substituent on an aryl, arylthio, arylsulphinyl, arylsulphonyl, heteroaryl, heteroarylthio, heteroarylsulphinyl or heteroarylsulphonyl group is, for example, methylthio, ethylthio, propylthio, isopropylthio, butylthio or isobutylthio.

A suitable value for $Y^2$ or $Y^3$ when it is halogeno, or for a halogeno substituent which may be present as a further substituent on the quinazoline ring, as a substituent on Ar, as a substituent on an aryl, arylthio, arylsulphinyl, arylsulphonyl, heteroaryl, heteroarylthio, heteroarylsulphinyl or heteroarylsulphonyl group, or as a substituent on a phenyl or phenylalkyl substituent or on a N-phenylsulphonylcarbamoyl group is, for example, fluoro, chloro or bromo.

A suitable value for $R^1$ when it is substituted alkyl is, for example, fluoromethyl, difluoromethyl, trifluoromethyl, 2-fluoroethyl, 3-fluoropropyl, hydroxymethyl, 2-hydroxyethyl or 3-hydroxypropyl.

A suitable value for $R^1$ when it is substituted alkoxy is, for example, 2-hydroxyethoxy, 2-methoxyethoxy, 3-methoxypropoxy or 2-ethoxyethoxy.

A suitable value for $R^2$ when it is hydroxyalkyl, halogenoalkyl or cyanoalkyl is, for example, 2-hydroxyethyl, 3-hydroxypropyl, 2-fluoroethyl, 2-chloroethyl, 2-bromoethyl, 3-fluoropropyl, 3-chloropropyl, cyanomethyl, 2-cyanoethyl or 3-cyanopropyl.

A suitable value for Ar when it is phenylene is, for example, 1,3- or 1,4-phenylene.

A suitable value for Ar when it is heterocyclene is, for example, a 5-membered or 6-membered aromatic (that is, fully unsaturated) heterocyclene ring which contains up to 3 heteroatoms selected from the group consisting of nitrogen and sulphur, for example, thienylene, pyridylene, pyrimidinylene or thiazolylene.

A suitable halogenoalkyl substituent in Ar is, for example, fluoromethyl, difluoromethyl or trifluoromethyl.

A suitable value for $Y^2$ or $Y^3$ when it is aryl, or for the aryl group when $Y^2$ or $Y^3$ is arylthio, arylsulphinyl or arylsulphonyl, is, for example, phenyl or naphthyl.

A suitable value for $Y^2$ or $Y^3$ when it is heteroaryl, or for the heteroaryl group when $Y^2$ or $Y^3$ is heteroarylthio, heteroarylsulphinyl or heteroarylsulphonyl is, for example, a 5-membered or 6-membered heterocyclic ring which contains up to 3 heteroatoms selected from the group consisting of oxygen, nitrogen and sulphur and which ring is optionally fused to a benzo ring, for example, furyl, thienyl, pyridyl, quinolyl, isoquinolyl, pyrazinyl, pyrimidinyl, pyridazinyl, quinoxalinyl, quinazolinyl, cinnolinyl, indolyl, imidazolyl, benzimidazolyl, pyrazolyl, oxazolyl, isoxazolyl, thiazolyl, 1,2,3-triazolyl or 1,2,4-triazolyl, which may be attached through any available position including through any available nitrogen atom and which may bear one or two substituents including a substituent on any available nitrogen atom.

A particular value for $Y^2$ or $Y^3$ when it is heteroaryl, or for the heteroaryl group when $Y^2$ or $Y^3$ is heteroarylthio, heteroarylsulphinyl or heteroarylsulphonyl is, for example, furyl, thienyl, pyridyl, imidazolyl, oxazolyl, isoxazolyl, thiazolyl, 1,2,3-triazolyl or 1,2,4-triazolyl, which may be attached through any available position.

A particular value for $Y^2$ or $Y^3$ when it is heteroaryl which bears one or two oxo or thioxo substituents, or for the heteroaryl group bearing such substituents when $Y^2$ or $Y^3$ is heteroarylthio, heteroarylsulphinyl or heteroarylsulphonyl, is, for example, 1,2-dihydro-2-oxoquinolinyl (especially 1,2-dihydro-2-oxoquinolin-3-yl and 1,2-dihydro-2-oxoquinolin-6-yl), 3,4-dihydro-4-oxoquinazolinyl (especially 3,4-dihydro-4-oxoquinazolin-5-yl, 3,4-dihydro-4-oxoquinazolin-6-yl, 3,4-dihydro-4-oxoquinazolin-7-yl and 3,4-dihydro-4-oxoquinazolin-8-yl), 5-oxo-1,2,4-triazolyl (especially 5-oxo-1,2,4-triazol-3-yl), 1,2-dihydro-2-oxopyridyl (especially 1,2-dihydro-2-oxopyrid-3-yl, 1,2-dihydro-2-oxopyrid-4-yl and 1,2-dihydro-2-oxopyrid-6-yl), 1,4-dihydro-4-oxopyridyl (especially 1,4-dihydro-4-oxopyrid-2-yl and 1,4-dihydro-4-oxopyrid-3-yl), 3,4-dihydro-4-oxopyrimidinyl (especially 3,4-dihydro-4-oxopyrimidin-2-yl and 3,4-dihydro-4-oxopyrimidin-5-yl) and 1,2,3,4-tetrahydro-2,4-dioxopyrimidinyl (especially 1,2,3,6-tetrahydro-2,6-dioxopyrimidin-4-yl and 1,2,3,4-tetrahydro-2,4-dioxopyrimidin-5-yl), or the corresponding thioxo-substituted compounds.

A suitable value for $A^1$, $A^2$ or $A^3$ when it is alkylene is, for example, methylene, ethylene, ethylidene, trimethylene, propylidene, isopropylidene, propylene, 1-ethylethylene, tetramethylene or isobutylidene.

A suitable value for $A^3$ when it is alkylene of up to 4 carbon atoms wherein a constituent methylene group is replaced by an oxy, thio, sulphinyl, sulphonyl, imino or hydroxymethylene group is, for example, 2-oxatrimethylene, 2-oxatetramethylene, 3-oxatetramethylene, 2-thiatrimethylene, 2-thiatetramethylene, 3-thiatetramethylene, 2-oxido-2-thiatrimethylene, 2,2-dioxido-2-thiatrimethylene, 2-azatrimethylene, hydroxymethylene [—CH(OH)—], 2-hydroxyethylene or 2-hydroxytrimethylene.

A suitable value for $Y^2$ or $Y^3$, or for a substituent which may be present on an aryl, arylthio, arylsulphinyl, arylsulphonyl, heteroaryl, heteroarylthio, heteroarylsulphinyl or heteroarylsulphonyl group when it is alkylamino, dialkylamino, halogenoalkyl, alkylsulphinyl, alkylsulphonyl, alkanoyloxy, alkanoyl or hydroxyalkanoyl is, for example, methylamino, ethylamino, propylamino, isopropylamino, butylamino, dimethylamino, N-ethyl-N-methylamino, diethylamino, N-methyl-N-propylamino, N-methyl-N-isopropylamino, fluoromethyl, difluoromethyl, trifluoromethyl, 2-fluoroethyl, 3-fluoropropyl, pentafluoroethyl, heptafluoropropyl, chloromethyl, dichloromethyl, methylsulphinyl, ethylsulphinyl, propylsulphinyl, isopropylsulphinyl, butylsulphinyl, methylsulphonyl, ethylsulphonyl, propylsulphonyl, isopropylsulphonyl, butylsulphonyl, acetoxy, propionyloxy, butyryloxy, acetyl, propionyl, butyryl, 2-hydroxyacetyl or 3-hydroxypropionyl.

A suitable value for $Y^3$ when it is one of the additional meanings of N-alkylsulphamoyl, N,N-dialkylsulphamoyl, N-acylsulphamoyl, N-alkylcarbamoyl, N,N-dialkylcarbamoyl, N-alkylcarbamoyloxy, N,N-dialkylcarbamoyloxy or N-alkylsulphonylcarbamoyl is, for example, N-methylsulphamoyl, N-ethylsulphamoyl, N,N-dimethylsulphamoyl, N-acetylsulphamoyl, N-propionylsulphamoyl, N-methylcarbamoyl, N-ethylcarbamoyl, N,N-dimethylcarbamoyl, N-methylcarbamoyloxy, N-ethylcarbamoyloxy, N,N-dimethylcarbamoyloxy, N-methylsulphonylcarbamoyl, N-ethylsulphonylcarbamoyl, N-propylsulphonylcarbamoyl or N-isopropylsulphonylcarbamoyl.

Suitable values for substituents which may be present on an aryl, arylthio, arylsulphinyl, arylsulphonyl, heteroaryl, heteroarylthio, heteroarylsulphinyl or heteroarylsulphonyl group are, for example:
  for N-alkylcarbamoyl: N-methylcarbamoyl, N-ethylcarbamoyl and N-propylcarbamoyl;
  for N,N-dialkylcarbamoyl: N,N-dimethylcarbamoyl;
  for phenylalkyl: benzyl, phenethyl, phenylpropyl and phenylbutyl.

A suitable pharmaceutically-acceptable salt of a quinazoline of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a quinazoline of the invention which is sufficiently acidic is an alkali metal salt, for example a sodium or potassium salt, an alkaline earth metal salt, for example a calcium or magnesium salt, an ammonium or tetra(2-hydroxyethyl)ammonium salt or a salt with an organic base which affords a physiologically-acceptable cation, for example a salt with methylamine, trimethylamine or tris(2-hydroxyethyl)amine.

According to a further aspect of the invention there is provided a quinazoline of the formula I
wherein $R^1$ is hydrogen or amino, or alkyl or alkoxy each of up to 4 carbon atoms;
or $R^1$ is alkyl of up to 3 carbon atoms which bears a hydroxy substituent, or which bears one, two or three fluoro substituents;
or $R^1$ is hydroxyalkoxy of up to 3 carbon atoms or alkoxyalkoxy of up to 4 carbon atoms;
wherein the quinazoline ring may bear no further substituent or may bear one further substituent selected from halogeno and from alkyl and alkoxy each of up to 3 carbon atoms;
wherein $R^2$ is hydrogen, alkyl, alkenyl, alkynyl, hydroxyalkyl, halogenoalkyl or cyanoalkyl each of up to 4 carbon atoms;
wherein $R^3$ is hydrogen or alkyl of up to 3 carbon atoms;
wherein Ar is phenylene or heterocyclene which may be unsubstituted or may bear one or two substituents selected from halogeno, hydroxy, amino and nitro, and from alkyl, alkoxy and halogenoalkyl each of up to 3 carbon atoms;

wherein L is a group of the formula —CO.NH—, —NH.CO—, —CO.NR⁴—, —NR⁴.CO—, —CH=CH— or —CO.O—, wherein R⁴ is alkyl of up to 4 carbon atoms;

and wherein Y is a group of the formula

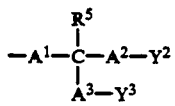

in which $R^5$ is hydrogen or alkyl of up to 3 carbon atoms;

$A^1$ is a direct link or is alkylene of up to 4 carbon atoms, $A^2$ is a direct link to $Y^2$ or is alkylene of up to 4 carbon atoms, $A^3$ is a direct link to $Y^3$ or is alkylene of up to 4 carbon atoms;

$Y^2$ is hydroxy, amino, cyano, halogeno or trifluoroacetyl, or alkoxy, alkylamino, dialkylamino, halogenoalkyl, alkylthio, alkylsulphinyl, alkylsulphonyl, alkanoyloxy, alkanoyl or hydroxyalkanoyl each of up to 4 carbon atoms, or aryl, arylthio, arylsulphinyl or arylsulphonyl each of up to 10 carbon atoms, or heteroaryl;

and $Y^3$ has any of the meanings defined above for $Y^2$, or in addition $Y^3$ is sulpho, N-hydroxycarbamoyl, N-cyanocarbamoyl, carbazoyl or sulphamoyl, or N-alkylsulphamoyl, N,N-dialkylsulphamoyl, N-acylsulphamoyl, N-alkylcarbamoyl, N,N-dialkylcarbamoyl, N-alkylcarbamoyloxy, N,N-dialkylcarbamoyloxy or N-alkylsulphonylcarbamoyl each of up to 4 carbon atoms, N-phenylsulphonylcarbamoyl or 5-tetrazolyl;

and wherein each of said aryl, arylthio, arylsulphinyl, arylsulphonyl or heteroaryl groups may be unsubstituted or may bear one or two substituents selected from hydroxy, oxo, thioxo, amino, nitro, cyano, carbamoyl and halogeno, from alkyl, N-alkylcarbamoyl, N,N-dialkylcarbamoyl, alkylthio, alkylsulphinyl, alkylsulphonyl, alkoxy and halogenoalkyl each of up to 4 carbon atoms, and from phenyl and phenylalkyl of up to 10 carbon atoms;

and wherein said phenyl and phenylalkyl substituents or said N-phenylsulphonylcarbamoyl group may bear a substituent selected from nitro, cyano and halogeno and from alkyl and alkoxy each of up to 3 carbon atoms;

or a pharmaceutically-acceptable salt thereof;

provided that, in the group of the formula -L-Y, no constituent methylene or methine group is attached to more than one heteroatom which is not in a heteroaryl ring.

Particular novel compounds of the invention are, for example, quinazolines of the formula I wherein Y is a group of the formula

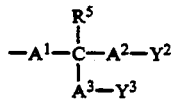

and wherein:

(a) $R^1$ is hydrogen, amino, methyl, ethyl, methoxy or fluoromethyl and the quinazoline ring may bear no further substituent or may bear one further substituent selected from fluoro, chloro, bromo, methyl and methoxy; and $R^2$, $R^3$, Ar, L, $A^1$, $A^2$, $A^3$, $R^5$, $Y^2$ and $Y^3$ have any of the meanings defined hereinbefore;

(b) $R^2$ is hydrogen, methyl, ethyl, propyl, prop-2-enyl, prop-2-ynyl, 2-hydroxyethyl, 3-hydroxypropyl, 2-fluoroethyl, 2-bromoethyl or cyanomethyl; and $R^1$, the quinazoline ring substituents, $R^3$, Ar, L, $A^1$, $A^2$, $A^3$, $R^5$, $Y^2$ and $Y^3$ have any of the meanings defined hereinbefore;

(c) $R^3$ is hydrogen, methyl or ethyl, and $R^1$, the quinazoline ring substituents, $R^2$, Ar, L, $A^1$, $A^2$, $A^3$, $R^5$, $Y^2$ and $Y^3$ have any of the meanings defined hereinbefore;

(d) Ar is 1,4-phenylene which is unsubstituted or which bears one or two substituents selected from fluoro, chloro, bromo, hydroxy, amino, nitro, methyl, methoxy and trifluoromethyl, or Ar is thienylene, pyridylene, pyrimidinylene or thiazolyene; and $R^1$, the quinazoline ring substituents, $R^2$, $R^3$, L, $A^1$, $A^2$, $A^3$, $R^5$, $Y^2$ and $Y^3$ have any of the meanings defined hereinbefore;

(e) L is a group of the formula —CO.NH—, —CO.NR⁴— or —CO.O—, wherein R⁴ is methyl or ethyl; and $R^1$, the quinazoline ring substituents, $R^2$, $R^3$, Ar, $A^1$, $A^2$, $A^3$, $R^5$, $Y^2$ and $Y^3$ have any of the meanings defined hereinbefore;

(f) $A^1$ is a direct link or is methylene, ethylene, ethylidene, trimethylene, propylidene, propylene, tetramethylene or isobutylidene, $A^2$ is a direct link to $Y^2$ or is methylene, ethylene, ethylidene, trimethylene, propylidene, propylene, tetramethylene or isobutylidene, and $A^3$ is a direct link to $Y^3$ or is methylene, ethylene, ethylidene, trimethylene, propylidene, propylene, tetramethylene or isobutylidene, or $A^3$ is 2-oxatrimethylene, 2-thiatrimethylene, 2-oxido-2-thiatrimethylene, 2,2-dioxido-2-thiatrimethylene, 2-azatrimethylene, hydroxymethylene, 2-hydroxyethylene or 2-hydroxytrimethylene; and $R^1$, the quinazoline ring substituents, $R^2$, $R^3$, Ar, L, $R^5$, $Y^2$ and $Y^3$ have any of the meanings defined hereinbefore;

(g) $Y^2$ and $Y^3$ each independently is hydroxy, amino, cyano, chloro, trifluoroacetyl, methoxy, ethoxy, propoxy, butoxy, tert-butoxy, methylamino, ethylamino, dimethylamino, diethylamino, trifluoromethyl, methylthio, ethylthio, methylsulphinyl, ethylsulphinyl, methylsulphonyl, ethylsulphonyl, acetoxy, propionyloxy, acetyl, 2-hydroxyacetyl, phenyl, phenylthio, phenylsulphinyl, phenylsulphonyl, thienyl, pyridyl, quinolyl, pyrimidinyl, quinazolinyl, imidazolyl, benzimidazolyl, isoxazolyl, thiazolyl, 1,2,3-triazolyl, 1,2,4-triazolyl, 1,2,4-triazolylthio, 1,2,4-triazolylsulphinyl or 1,2,4-triazolylsulphonyl, and wherein any aryl or heteroaryl group so defined may be unsubstituted or may bear one or two substituents selected from hydroxy, oxo, thioxo, amino, nitro, cyano, carbamoyl, fluoro, chloro, bromo, methyl, ethyl, N-methylcarbamoyl, N,N-dimethylcarbamoyl, methylthio, methylsulphinyl, methylsulphonyl, methoxy and trifluoromethyl; and $R^1$, the quinazoline ring substituents, $R^2$, $R^3$, Ar, L, $A^1$, $A^2$, $A^3$ and $R^5$ have any of the meanings defined hereinbefore;

(h) $Y^2$ is hydroxy, amino, cyano, chloro, methoxy, ethoxy, propoxy, tert-butoxy, methylamino, ethylamino, dimethylamino, diethylamino, methylthio, ethylthio, methylsulphinyl, ethylsulphinyl, methylsulphonyl, ethylsulphonyl, acetoxy, propionyloxy, acetyl or propionyl, or $Y^2$ is phenyl, phenylthio, phenylsulphinyl, phenylsulphonyl, thienyl, thiazolyl, pyridyl, 1,2,4-triazolyl, 1,2,4-triazolylthio, 1,2,4-triazolylsulphinyl or 1,2,4-triazolylsulphonyl, and wherein any of said eleven last named groups for $Y^2$ may be unsubstituted or may bear one or two substituents selected from hydroxy, amino, nitro, cyano, fluoro, chloro, bromo, methyl, ethyl, methoxy and trifluoromethyl, and wherein, in addition, any of said 5 last-named groups for $Y^2$ may bear an oxo or thioxo substituent, and $Y^3$ is phenyl, thienyl, pyridyl, imidazolyl, oxazolyl, isoxazolyl, thiazolyl or 1,2,4-triazolyl, and wherein each of said groups may be unsubstituted or may bear one or two substituents selected from hydroxy, amino, nitro, cyano, fluoro, chloro, bromo, methyl, ethyl, methylthio, methylsulphinyl, methylsulphonyl, methoxy and trifluoromethyl, and wherein, in addition said pyridyl or 1,2,4-triazolyl group may bear an oxo or thioxo substituent; and $R^1$, the quinazoline ring substituents, $R^2$, $R^3$, Ar, L, $A^1$, $A^2$, $A^3$ and $R^5$ have any of the meanings defined hereinbefore; and (i) $Y^2$ is phenyl which may be unsubstituted or may bear one or two substituents selected from hydroxy, amino, nitro, cyano, fluoro, chloro, bromo, methyl, methoxy and trifluoromethyl, and $Y^3$ is sulpho, N-hydroxycarbamoyl, N-cyanocarbamoyl, carbazolyl, sulphamoyl, N-methylsulphamoyl, N-ethylsulphamoyl, N-acetylsulphamoyl, N-methylcarbamoyl, N-ethylcarbamoyl, N-methylcarbamoyloxy, N-methylsulphonylcarbamoyl, N-ethylsulphonylcarbamoyl, N-isopropylsulphonylcarbamoyl, N-phenylsulphonylcarbamoyl or 5-tetrazolyl, and said N-phenylsulphonylcarbamoyl group may bear a substituent selected from nitro, cyano, fluoro, chloro, methyl and methoxy; and $R^1$, the quinazoline ring substituents, $R^2$, $R^3$, Ar, L, $A^1$, $A^2$, $A^3$ and $R^5$ have any of the meanings defined hereinbefore;
or a pharmaceutically-acceptable salt thereof; provided that, in any group of the formula -L-Y, no constituent methylene or methine group is attached to more than one heteroatom which is not in a heteroaryl ring.

A particular quinazoline of the invention has the formula I wherein $R^1$ is hydrogen, amino, methyl, ethyl, methoxy or fluoromethyl; wherein the quinazoline ring may bear no further substituent or may bear one further substituent selected from fluoro, chloro, methyl and methoxy;

wherein $R^2$ is hydrogen, methyl, ethyl, propyl, prop-2-enyl, prop-2-ynyl, 2-hydroxyethyl, 3-hydroxypropyl, 2-fluoroethyl, 2-bromoethyl or cyanomethyl;

wherein $R^3$ is hydrogen, methyl or ethyl;

wherein Ar is 1,4-phenylene, thienylene, pyridylene, pyrimidinylene or thiazolylene which is unsubstituted or which bears one or two substituents selected from fluoro, chloro, bromo, hydroxy, amino, nitro, methyl, methoxy and trifluoromethyl;

wherein L is a group of the formula —CO.NH—, —CO.NR$^4$— or —CO.O—, wherein $R^4$ is methyl or ethyl; and
wherein Y is a group of the formula

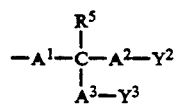

in which
$R^5$ is hydrogen, methyl or ethyl;
$A^1$ is a direct link or is methylene, ethylene, ethylidene, trimethylene, propylidene, propylene, tetramethylene or isobutylidene, $A^2$ is a direct link to $Y^3$ or is methylene, ethylene, ethylidene, trimethylene, propylidene, propylene, tetramethylene or isobutylidene, $A^3$ is a direct link to $Y^3$ or is methylene, ethylene, ethylidene, trimethylene, propylidene, propylene, tetramethylene or isobutylidene; $Y^2$ is hydroxy, amino, cyano, chloro, trifluoroacetyl, methoxy, ethoxy, methylamino, ethylamino, dimethylamino, diethylamino, trifluoromethyl, methylthio, ethylthio, methylsulphinyl, ethylsulphinyl, methylsulphonyl, ethylsulphonyl, acetoxy, propionyloxy, acetyl, 2-hydroxyacetyl, phenyl, phenylthio, phenylsulphinyl, phenylsulphonyl, thienyl, pyridyl, quinolyl, pyrimidinyl, quinazolinyl, imidazolyl, benzimidazolyl, thiazolyl, 1,2,3-triazolyl or 1,2,4-triazolyl;

and $Y^3$ has any of the meanings defined immediately above for $Y^2$, or in addition $Y^3$ may be sulpho, N-hydroxycarbamoyl, N-cyanocarbamoyl, carbazolyl, sulphamoyl, N-methylsulphamoyl, N-ethylsulphamoyl, N-acetylsulphamoyl, N-methylcarbamoyl, N-ethylcarbamoyl, N-methylcarbamoyloxy, N-methylsulphonylcarbamoyl, N-ethysulphonylcarbamoyl, N-isopropylsulphonylcarbamoyl, N-phenylsulphonylcarbamoyl or 5-tetrazolyl; and wherein each of said phenyl, phenylthio, phenylsulphinyl, phenylsulphonyl or heteroaryl groups may be unsubstituted or may bear one or two substituents selected from hydroxy, oxo, thioxo, amino, nitro, cyano, carbamoyl, fluoro, chloro, bromo, methyl, ethyl, N-methylcarbamoyl, N,N-dimethylcarbamoyl, methylthio, methylsulphinyl, methylsulphonyl, methoxy, trifluoromethyl, phenyl and benzyl; and wherein said phenyl or benzyl substituents or said N-phenylsulphonylcarbamoyl group may bear a substituent selected from nitro, cyano, fluoro, chloro, methyl and methoxy;
or a pharmaceutically-acceptable salt thereof;

provided that, in the group of the formula -L-Y, no constituent methylene or methine group is attached to more than one heteroatom which is not in a heteroaryl ring.

A further particular quinazoline of the invention has the formula I wherein $R^1$ is methyl; wherein $R^2$ is methyl, ethyl, prop-2-ynyl or 2-fluoroethyl;

wherein the quinazoline ring may bear no further substituent or may bear a 7-fluoro or 7-methyl substituent;

wherein $R^3$ is hydrogen;

wherein Ar is 1,4-phenylene or thien-2,5-diyl, or is pyrid-2,5-diyl or thiazol-2,5-diyl each with the group -L-Y in the 2-position, or is 2-fluoro-1,4-phenylene with the group -L-Y in the 1-position;

wherein L is a group of the formula —CO.NH—; and
wherein Y is a group of the formula

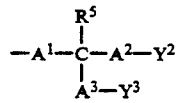

in which
$R^5$ is hydrogen or methyl;
$A^1$ is a direct link or is methylene or ethylene, $A^2$ is a direct link to $Y^2$ or is methylene or ethylene, $A^3$ is a direct link to $Y^3$ or is methylene or ethylene;

$Y^2$ is hydroxy, amino, cyano, chloro, methoxy, methylamino, ethylamino, dimethylamino, diethylamino, methylthio, ethylthio, acetoxy, phenyl, phenylthio, 2-thienyl, 2-pyridyl, 3-pyridyl, 4-pyridyl, 6-pyridyl, 3-quinolyl, 4-quinolyl, 2-pyrimidinyl, 4-pyrimidinyl, 6-quinazolinyl, 2-imidazolyl, 2-thiazolyl, 5-thiazolyl, 1,2,4-triazol-1-yl or 1,2,4-triazol-3-yl; and $Y^3$ has any of the meanings defined above for $Y^2$ or in addition $Y^3$ may be N-methylcarbamoyl, N-methylsulphonylcarbamoyl, N-phenylsulphonylcarbamoyl or 5-tetrazolyl;

and wherein each of said phenyl, phenylthio or heteroaryl groups may be unsubstituted or may bear one or two substituents selected from hydroxy, oxo, amino, nitro, cyano, carbamoyl, fluoro, chloro, methyl, methoxy, trifluoromethyl and benzyl;

and wherein said benzyl substituent or said N-phenylsulphonylcarbamoyl group may bear a substituent selected from nitro, fluoro, chloro, methyl or methoxy;

or a pharmaceutically-acceptable salt thereof; provided that, in the group of the formula -L-Y, no constituent methylene or methine group is attached to more than one heteroatom which is not in a heteroaryl ring.

A further particular quinazoline of the invention has the formula I wherein
$R^1$ is methyl;
wherein $R^2$ is methyl, ethyl or prop-2-ynyl;
wherein the quinazoline ring may bear no further substituent or may bear a 7-fluoro or 7-methyl substituent;
wherein $R^3$ is hydrogen;
wherein Ar is 1,4-phenylene or thien-2,5-diyl, or is thiazol-2,5-diyl with the group -L-Y in the 2-position, or is 2-fluoro-1,4-phenylene with the group -L-Y in the 1-position;
wherein L is a group of the formula —CO.NH— and
wherein Y is a group of the formula
$-A^1-CH(A^3-Y^3)-A^2-Y^2$ in which
$A^1$ is a direct link to the methine group or is methylene,
$A^2$ is a direct link to $Y^2$ or is methylene,
$A^3$ is a direct link to $Y^3$ or is methylene;
$Y^2$ is hydroxy, cyano, acetoxy or 1,2-dihydro-2-oxopyrid-6-yl, or $Y^2$ is phenyl or phenylthio which may be unsubstituted or may bear a substituent selected from nitro, chloro, methyl, methoxy and trifluoromethyl; and
$Y^3$ has any of the meanings defined above for $Y^2$ or in addition $Y^3$ is N-methylsulphonylcarbamoyl, N-phenylsulphonylcarbamoyl or 5-tetrazolyl; and wherein said N-phenylsulphonylcarbamoyl group may bear a substituent selected from nitro, chloro, methyl and methoxy;
or a pharmaceutically-acceptable salt thereof; provided that, in the group of the formula -L-Y, no constituent methylene or methine group is attached to more than one heteroatom.

A preferred quinazoline of the invention has the formula I
wherein $R^1$ is amino or methyl;
wherein $R^2$ is methyl, ethyl, prop-2-ynyl or 2-fluoroethyl;
wherein the quinazoline ring may bear no further substituent or may bear a 7-fluoro, 7-chloro, 7-bromo or 7-methyl substituent;
wherein $R^3$ is hydrogen;
wherein Ar is 1,4-phenylene or thien-2,5-diyl, or is pyrid-2,5-diyl or thiazol-2,5-diyl each with the group -L-Y in the 2-position, or is 2-fluoro-1,4-phenylene with the group -L-Y in the 1-position;
wherein L is a group of the formula —CO.NH—; and
wherein Y is a group of the formula

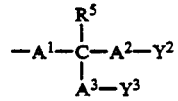

in which
$R^5$ is hydrogen or methyl;
$A^1$ is a direct link or is methylene, $A^2$ is a direct link to $Y^2$ or is methylene, $A^3$ is a direct link to $Y^3$ or is methylene, ethylene, trimethylene, 2-thiatrimethylene or hydroxymethylene; $Y^2$ is hydroxy, amino, cyano, methoxy, ethoxy, tert-butoxy, methylamino, dimethylamino, methylthio, methylsulphinyl, methylsulphonyl, acetoxy or acetyl, or $Y^2$ is phenyl, phenylthio, thiazolyl, 1,2,4-triazolyl, 1,2,4-triazolylthio, 1,2,4-triazolylsulphinyl or 1,2,4-triazolylsulphonyl and wherein any of said seven last-named groups may be unsubstituted or may bear one substituent selected from hydroxy, nitro, fluoro, chloro, methyl, methoxy and trifluoromethyl;
and $Y^3$ is phenyl, thienyl, pyridyl, isoxazolyl or thiazolyl, and wherein each of said groups may be unsubstituted or may bear one or two substituents selected from hydroxy, nitro, fluoro, chloro, methyl, methoxy and trifluoromethyl, or in addition said pyridyl group may bear an oxo substituent;
or a pharmaceutically-acceptable salt thereof.

A further particular quinazoline of the invention has the formula I
wherein $R^1$ is methyl;
wherein $R^2$ is methyl, ethyl, prop-2-ynyl or 2-fluoroethyl;
wherein the quinazoline ring may bear no further substituent or may bear a 7-fluoro, 7-chloro, 7-bromo or 7-methyl substituent;
wherein $R^3$ is hydrogen;
wherein Ar is 1,4-phenylene or thien-2,5-diyl, or is pyrid-2,5-diyl or thiazol-2,5-diyl each with the group -L-Y in the 2-position, or is 2-fluoro-1,4-phenylene with the group -L-Y in the 1position;
wherein L is a group of the formula —CO.NH—; and
wherein Y is a group of the formula

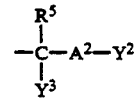

in which
$R^5$ is hydrogen or methyl;
$A^2$ is a direct link to $Y^2$ or is methylene;
$Y^2$ is phenyl which may be unsubstituted or may bear a substituent selected from nitro, chloro, methyl, methoxy and trifluoromethyl; and
$Y^3$ is N-methylcarbamoyl, N-methylsulphonylcarbamoyl, N-phenylsulphonylcarbamoyl or 5-tetrazolyl, and wherein said N-phenylsulphonylcarbamoyl group may bear a substituent selected from nitro, fluoro, chloro, methyl or methoxy;
or a pharmaceutically-acceptable salt thereof.

A further preferred quinazoline of the invention has the formula I
wherein $R^1$ is amino or methyl;
wherein $R^2$ is methyl, ethyl or prop-2-ynyl;

wherein the quinazoline ring may bear no further substituent or may bear a 7-fluoro, 7-chloro, 7-bromo or 7-methyl substituent;

wherein $R^3$ is hydrogen;

wherein Ar is 1,4-phenylene or thien-2,5-diyl, or is thiazol-2,5-diyl with the group -L-Y in the 2-position, or is 2-fluoro-1,4-phenylene with the group -L-Y in the 1-position;

wherein L is a group of the formula —CO.NH—; and wherein Y is a group of the formula $$—CH(A^3—Y^3)—A^2—Y^2$$

in which $A^2$ is a direct link to $Y^2$ or is methylene or ethylene;

$A^3$ is a direct link to $Y^3$ or is methylene;

$Y^2$ is hydroxy, cyano, methoxy, ethoxy, tert-butoxy, dimethylamino, phenyl, 1,2,4-triazol-3-ylthio or 1,2,4-triazol-3-ylsulphinyl; and $Y^3$ is phenyl or 3-nitrophenyl;

or a pharmaceutically-acceptable salt thereof.

A further preferred quinazoline of the invention has the formula I wherein $R^1$ is methyl;

wherein $R^2$ is methyl, ethyl or prop-2-ynyl;

wherein the quinazoline ring may bear no further substituent or may bear a 7-fluoro, 7-chloro, 7-bromo or 7-methyl substituent;

wherein $R^3$ is hydrogen;

wherein Ar is 1,4-phenylene or thien-2,5-diyl, or is thiazol-2,5-diyl with the group -L-Y in the 2-position, or is 2-fluoro-1,4-phenylene with the group -L-Y in the 1-position;

wherein L is a group of the formula —CO.NH—; and wherein Y is a group of the formula $$—CH(Y^3)—Y^2$$

in which $Y^2$ is phenyl which may be unsubstituted or may bear a nitro substituent; and $Y^3$ is N-methylsulphonylcarbamoyl, N-phenylsulphonylcarbamoyl or 5-tetrazolyl, and wherein said N-phenylsulphonylcarbamoyl group may bear a substituent selected from nitro, chloro, methyl and methoxy; or a pharmacuetically-acceptable salt thereof.

An especially preferred quinazoline of the invention has the formula I wherein $R^1$ is methyl;

wherein $R^2$ is methyl or prop-2-ynyl;

wherein the quinazoline ring may bear no further substituent or may bear a 7-fluoro, 7-bromo or 7-methyl substituent;

wherein $R^3$ is hydrogen;

wherein Ar is 1.4-phenylene or is 2-fluoro-1,4-phenylene with the group -L-Y in the 1-position;

wherein L is a group of the formula —CO.NH—; and wherein Y is a group of the formula $$—CH(Y^3)—A^2—Y^2$$

in which $A^2$ is methylene or ethylene;

$Y^2$ is hydroxy; and $Y^3$ is 3-nitrophenyl;

or a pharmaceutically-acceptable salt thereof.

A further especially preferred quinazoline of the invention has the formula I wherein $R^1$ is methyl;

wherein $R^2$ is prop-2-ynyl;

wherein the quinazoline ring may bear no further substituent or may bear a 7-fluoro or 7-methyl substituent;

wherein $R^3$ is hydrogen;

wherein Ar is 1.4-phenylene or is 2-fluoro-1,4-phenylene with the group -L-Y in the 1-position;

wherein L is a group of the formula —CO.NH—; and wherein Y is a group of the formula $$—CH(Y^3)—Y^2$$

in which $Y^2$ is phenyl which may be unsubstituted or may bear a nitro substituent; and $Y^3$ is N-methylsulphonylcarbamoyl, N-phenylsulphonylcarbamoyl, N-(4-methoxyphenylsulphonyl)carbamoyl or 5-tetrazolyl; or a pharmaceutically-acceptable salt thereof.

Specific especially preferred compounds of the invention include, for example, the following quinazolines of the formula I; or pharmaceutically-acceptable salts thereof:

N-[2-hydroxy-1-(3-nitrophenyl)ethyl]-p-]N-(2-methyl-4-oxo-3,4-dihydroquinazolin-6-ylmethyl)-N-(prop-2-ynyl)amino]benzamide, p-[N-(2,7-dimethyl-4-oxo-3,4-dihydroquinazolin-6-ylmethyl)-N-(prop-2-ynyl)amino]-N-[2-hydroxy-1-(3-nitrophenyl)ethyl]benzamide, p-[N-(2,7-dimethyl-4-oxo-3,4-dihydroquinazolin-6-ylmethyl)-N-(prop-2-ynyl)amino]-o-fluoro-N-[2-hydroxy-1-(3-nitrophenyl)ethyl]benzamide, p-[N-(2,7-dimethyl-4-oxo-3,4-dihydroquinazolin-6-ylmethyl)-N-methylamino]-N-[2-hydroxy-1-(3-nitrophenyl)ethyl]benzamide and p-[N-(7-bromo-2-methyl-4-oxo-3,4-dihydroquinazolin-6-ylmethyl)-N-(prop-2-ynyl)amino]-N-[2-hydroxy-1-(3-nitrophenyl)ethyl]benzamide.

A further group of specific especially preferred compounds includes, for example, the following quinazolines of the formula I, or pharmaceutically-acceptable salts thereof:

o-fluoro-p-[N-(2-methyl-4-oxo-3,4-dihydroquinazolin-6-ylmethyl)-N-(prop-2-ynyl)amino]-N-[3-nitro-α-(5-tetrazolyl)benzyl]benzamide, p-[N-(2,7-dimethyl-4-oxo-3,4-dihydroquinazolin-6-ylmethyl)-N-(prop-2-ynyl)amino]-N-[3-nitro-α-(5-tetrazolyl)benzyl]benzamide, p-[N-(7-fluoro-2-methyl-4-oxo-3,4-dihydroquinazolin-6-ylmethyl)-N-(prop-2-ynyl)amino]-N-[3-nitro-α-(5-tetrazolyl)benzyl]benzamide, N-[p-[N-(2-methyl-4-oxo-3,4-dihydroquinazolin-6-ylmethyl)-N-(prop-2-ynyl)amino]benzoyl-(3-nitrophenyl)glycine N-(4-methoxyphenylsulphonyl)amide and N-[p-[N-(2,7-dimethyl-4-oxo-3,4-dihydroquinazolin-6-ylmethyl)-N-(prop-2-ynyl)amino]benzoyl-(3-nitrophenyl)glycine N-(methylsulphonyl)amide.

A quinazoline of the invention, or a pharmaceutically-acceptable salt thereof, may be prepared by any process known to be applicable to the preparation of chemically-related compounds. Such processes are provided as a further feature of the invention and are illustrated by the following representative examples, processes (a) to (f).

(a) A preferred process for the manufacture of a quinazoline of the invention comprises the reaction of a compound of the formula II (set out hereinafter) wherein $R^1$ and $R^3$ have the meanings stated above, provided that when $R^1$ is amino, hydroxyalkyl or hydroxyalkoxy any amino or hydroxy group is protected by a conventional protecting group, $R^6$ is hydrogen or a protecting group and Z is a displaceable group, with a compound of the formula:

HNR²—Ar—L—Y wherein $R^2$, Ar, L and Y have the meanings stated above, provided that when there is an amino, alkylamino or hydroxy group in $R^2$, Ar or Y, any amino or alkylamino group is protected by a conventional protecting group and any hydroxy group may be protected by a conventional protecting group or alternatively any hydroxy group need not be protected, whereafter any undesired protecting group in $R^1$, $R^2$, Ar and Y is removed.

The reaction is preferably carried out in the presence of a suitable base such as, for example, an alkali or alkaline earth metal carbonate or hydroxide, for example sodium carbonate, potassium carbonate, calcium carbonate, sodium hydroxide or potassium hydroxide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is preferably carried out in a suitable inert solvent or diluent, for example N,N-dimethylformamide, N,N-dimethylacetamide, M-methylpyrrolidin-2-one or dimethylsulphoxide and at a temperature in the range, for example, 25° to 150° C., conveniently at or near 80° C.

A suitable protecting group for a hydroxy group may be, for example, an esterifying group, for example an acetyl or benzoyl group, which may be removed by hydrolysis with a base, for example sodium hydroxide, or provided that $R^2$, L and Y do not contain an alkenyl or alkynyl group, the protecting group may be, for example, an α-arylalkyl group, for example a benzyl group, which may be removed by hydrogenation over a catalyst, for example palladium-on-charcoal.

A suitable protecting group for an amino or alkylamino group may be, for example, an alkoxycarbonyl group, for example a tert-butoxycarbonyl group which may be removed by treatment with an organic acid, for example trifluoroacetic acid; or it may be, for example, a benzyloxycarbonyl group which may be removed by treatment with a Lewis acid, for example boron tris(trifluoroacetate).

A suitable alternative protecting group for a primary amino group is, for example, a phthaloyl group which may be removed by treatment with an alkylamine, for example dimethylaminopropylamine, or with hydrazine.

A suitable value for $R^6$ when it is a protecting group is, for example, a pivaloyloxymethyl group which may be removed by hydrolysis with a base, for example sodium hydroxide, or by reaction with a base such as ammonia gas in a suitable inert solvent or diluent, for example methanol or ethanol Z may be, for example, a halogeno or sulphonyloxy group, for example a chloro, bromo, methanesulphonyloxy or toluene-p-sulphonyloxy group.

The compound of the formula:

HNR²—Ar-13 L—Y wherein L is a group of the formula —CO.NH— or —CO.NR⁴— wherein $R^4$ has the meanings stated above, used as a starting material above, may be obtained by the reaction of an acid of the formula:

O₂N—Ar—CO₂H or a reactive derivative thereof, wherein Ar has the meaning stated above with an amine of the formula:

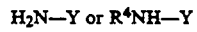
H₂N—Y or R⁴NH—Y wherein $R^4$ and Y have the meanings stated above and any amino or alkylamino group in Ar and Y is protected by a conventional protecting group as stated above and any hydroxy group in Ar and Y may be protected by a conventional protecting group as stated above or alternatively any hydroxy group need not be protected. Thereafter the nitro group may be reduced by conventional means to an amino group which in turn may be alkylated with a compound of the formula $R^2$-Z wherein $R^2$ and Z have the meanings stated above.

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol or an alcohol such as 1-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide, for example dicyclohexylcarbodiimide.

The compound of the formula:

HNR²—Ar—L—Y wherein L is a group of the formula —NH.CO— or —NR⁴.CO— wherein $R^4$ has the meaning stated above, used as a starting material above, may be obtained by the reaction of an amine of the formula:

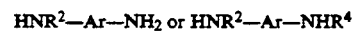
HNR²—Ar—NH₂ or HNR²—Ar—NHR⁴ wherein Ar has the meaning stated above with an acid of the formula:

HO₂C—Y or a reactive derivative thereof, wherein Y has the meaning stated above and any amino or alkylamino group in Ar and Y is protected by a conventional protecting group as stated above and any hydroxy group in Ar and Y may be protected by a conventional protecting group as stated above or alternatively any hydroxy group need not be protected.

The compound of the formula:

HNR²—AR—L—Y wherein L is a group of the formula —CH=CH—, used as a starting material above, may be obtained by the reaction of an aldehyde of the formula:

HNG¹—AR—CHO wherein Ar has the meaning stated above and $G^1$ is a conventional protecting group for an amino group as stated above, for example an alkoxycarbonyl group, with a triphenylphosphonium salt of the formula:

$$(Ph)_3P^+\text{—}CH_2\text{—}Y\ Z^-$$

wherein Y has the meaning stated above and wherein $Z^-$ is an anion, for example the bromide ion, and any amino or alkylamino group in Ar and Y is protected by a conventional protecting group as stated above and any hydroxy group in Ar and Y may be protected by a conventional protecting group as stated above or alternatively any hydroxy group need not be protected.

The reaction may be carried out in solution in dimethyl sulphoxide in the presence of dimsyl sodium. Thereafter the protecting group $G^1$ may be removed by conventional means and whereafter the amine of the formula:

$$H_2N\text{—}Ar\text{—}CH\text{=}CH\text{—}Y$$

may be alkylated with a compound of the formula $R^2\text{—}Z$ wherein $R^2$ and Z have the meanings stated above. The protecting group $G^1$ may be chosen such that it may be removed while the conventional protecting group on any amino, alkylamino and imino group in Ar and Y remains intact.

The triphenylphosphonium salt of the formula:

$$(Ph)_3P^+\text{—}CH_2Y\ Z^-$$

used as a starting material above may be obtained by the reaction of triphenylphosphine with a compound of the formula:

$$Y\text{—}CH_2\text{—}Z$$

wherein Y and Z have the meanings stated above.

Alternatively the compound of the formula:

$$HNR^2\text{—}AR\text{—}L\text{—}Y$$

wherein L is a group of the formula —CH=CH—, used as a starting material above, may be obtained by the reaction of an aldehyde of the formula:

$$O_2N\text{—}Ar\text{—}CHO$$

wherein Ar has the meaning stated above with a triphenylphosphonium salt of the formula:

$$(Ph)_3P^+\text{—}CH_2\text{—}Y\ Z^-$$

wherein Y and $Z^-$ have the meanings stated above and any amino or alkylamino group in Ar and Y is protected by a conventional protecting group as stated above and any hydroxy group in Ar and Y may be protected by a conventional protecting group as stated above or alternatively any hydroxy group need not be protected.

The reaction may be carried out in solution in dimethylsulphoxide in the presence of dimsyl sodium. Thereafter the nitro group may be reduced by conventional means to an amino group which in turn may be alkylated with a compound of the formula $R^2$-Z wherein $R^2$ and Z have the meanings stated above.

The compound of the formula:

$$HNR^2\text{—}Ar\text{—}L\text{—}Y$$

wherein L is a group of the formula —CO.O—, used as a starting material above, may be obtained by the reaction of an acid of the formula:

$$O_2N\text{—}Ar\text{—}CO_2H$$

or a conventional reactive derivative thereof, wherein Ar has the meaning stated above with an alcohol of the formula:

$$HO\text{—}Y$$

wherein Y has the meaning stated above and any amino, alkylamino or hydroxy group in Ar and Y is protected by a conventional protecting group. Thereafter the nitro group may be reduced by conventional means to an amino group which in turn may be alkylated with a compound of the formula $R^2$-Z wherein $R^2$ and Z have the meanings stated above.

(b) A further preferred process for the manufacture of a quinazoline of the invention wherein L is a group of the formula —CO.NH— or —CO.$NR^4$—, comprises the reaction of an acid of the formula III, or a reactive derivative thereof, with a compound of the formula:

$$H_2N\text{—}Y\ \text{or}\ R^4NH\text{—}Y$$

wherein $R^1$, $R^2$, $R^3$, $R^4$, $R^6$, Ar and Y have the meanings stated above and any amino or alkylamino group in $R^1$, Ar and Y is protected by a conventional protecting group as stated above and any hydroxy group in $R^1$, $R^2$, Ar and Y may be protected by a conventional protecting group as stated above or alternatively any hydroxy group need not be protected, whereafter the protecting groups are removed by conventional means.

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol or an alcohol such as 1-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide, for example dicyclohexylcarbodiimide.

The reaction is preferably carried out in the presence of a suitable base as stated above, in a suitable solvent or diluent such as methylene chloride, N,N-dimethylformamide, N,N-dimethylacetamide, N-methylpyrrolidin-2-one or dimethylsulphoxide and at a temperature in the range, for example, 10° to 100° C., conveniently at or near laboratory temperature.

The carboxylic acid used as starting material may be obtained by the reaction of a compound of the formula II wherein $R^1$, $R^4$ and Z have the meanings stated above, with a compound of the formula:

$$HNR^2\text{—}Ar\text{—}CO_2R^7$$

wherein $R^2$ and Ar have the meanings stated above and $R^7$ is a protecting group which can be removed to provide a carboxylic acid. $R^7$ may be, for example, a methyl or an ethyl group which may be removed by hydrolysis with a base, for example sodium hydroxide or R⁷ may be, for example, a tert-butyl group which may be removed by cleavage with an organic acid, for example trifluoroacetic acid.

The protecting group for the carboxy group in R⁷ may be, for example, an esterifying group which can be removed while the protecting group for any amino, alkylamino and hydroxy group in R¹, R², Ar and Y is retained.

(c) A further preferred process for the manufacture of a quinazoline of the invention wherein L is a group of the formula —CO.O—, comprises the reaction, in the presence of a suitable base as stated above, of an acid of the formula III, or a reactive derivative thereof, with a compound of the formula:

HO—Y wherein R¹, R², R³, R⁶, Ar and Y have the meanings stated above and any amino, alkylamino or hydroxy group in R¹, R², Ar and Y is protected by a conventional protecting group as stated above, whereafter the protecting groups are removed by conventional means.

The reaction is preferably carried out in a suitable solvent or diluent such as N,N-dimethylformamide, N,N-dimethylacetamide, N-methylpyrrolidin-2-one or dimethylsulphoxide at a temperature in the range 10° to 100° C., conveniently at or near laboratory temperature.

(d) A further preferred process for the manufacture of a quinazoline of the invention, wherein R¹ is alkoxy, hydroxyalkoxy or alkoxyalkoxy, comprises the reaction of a compound of the formula IV wherein R¹ has the last-mentioned meaning stated above, provided that when there is a hydroxy substituent in R¹ it is protected by a conventional protecting group as stated above, and Z is a displaceable group, with a compound of the formula:

HNR²—Ar—L—Y wherein R², Ar, L and Y have the meanings stated above, provided that when there is an amino, alkylamino or hydroxy group in R², Ar or Y any amino or alkylamino group is protected by a conventional protecting group as stated above and any hydroxy group may be protected by a conventional protecting group, as stated above or alternatively any hydroxy group need not be protected, whereafter the protecting groups are removed by conventional means, as stated above and the R¹ group situated at the 4-position of the quinazoline ring is cleaved by hydrolysis with a base, for example sodium hydroxide, to form a quinazoline of the invention.

(e) A further preferred process for the manufacture of a quinazoline of the invention wherein there is an alkysulphinyl, arylsulphinyl, heteroarylsulphinyl, alkylsulphonyl, arylsulphonyl or heteroarylsulphonyl group in Y, comprises the oxidation of a compound of the formula I wherein there is an alkylthio, arylthio or heteroarylthio group in Y, with a suitable oxidising agent.

A suitable oxidising agent is, for example, any reagent known to oxidise a thio group to a sulphinyl or sulphonyl group, for example, hydrogen peroxide, a peracid such as 3-chloroperbenzoic acid or peroxyacetic acid, or chromium trioxide. When a compound carrying a sulphinyl group is required the required stoichiometric amount of any one of the above oxidising agents may be used in order to reduce the production of a compound carrying a sulphonyl group. Alternatively a milder oxidising agent may be used, for example sodium or potassium metaperiodate. It will be appreciated that when a compound of the formula I containing a sulphonyl group is required, it may be obtained by the oxidation of the corresponding sulphinyl compound as well as by the oxidation of the corresponding thio compound.

(f) A further preferred process for the manufacture of a quinazoline of the invention wherein there is an alkanoyloxy group in Y, comprises the acylation of a compound of the formula I wherein there is a hydroxy group in Y.

Suitable conditions for the acylation reaction include, for example, reaction of the hydroxy group with an alkanoic acid, or a reactive derivative thereof, as stated above.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carring out one of the aforesaid processes using an optically active starting material, or by resolution of a racemic form of said compound using a conventional procedure.

As stated above a quinazoline derivative of the present invention possesses anti-tumour activity. This activity may be assessed, for example, using one or more of the procedures set out below:

(a) An in vitro assay which determines the ability of a test compound to inhibit the enzyme thymidylate synthase. Thymidylate synthase was obtained in partially purified form from L1210 mouse leukaemia cells and utilised using the procedures described by Jackman et al. (*Cancer Res.*, 1986, 46, 2810 and Sikora et al., *Biochem. Pharmacol.* 1988, 37, 4047);

(b) An assay which determines the ability of a test compound to inhibit the growth of the leukaemia cell line L1210 in cell culture. The test is similar to that described in UK Patent Specification No. 2065653B and has been described by Jones et al., *J. Med. Chem.*, 1985, 28, 1468;

(c) An assay which determines the ability of a test compound to inhibit the growth of the human breast cancer cell line MCF-7 in cell culture. The test is similar to that described by Lippman et al. (*Cancer Res.*, 1976, 36, 4595); and (d) A cloning assay which determines the ability of a test compound to be cytotoxic to the lymphoma cell line L5178Y TK-/- in vitro. The lymphoma cell line L5178Y TK-/- is deficient in the enzyme thymidine kinase which phosphorylates thymidine and thus operates to generate a pool of thymidylate when de novo synthesis of thymidylate is prevented by the presence of an effective amount of an inhibitor of thymidylate synthase. The L5178Y TK-/- cell line is thereby more sensitive to the presence of an inhibitor of thymidylate synthase in cloning assays. [L5178Y TK-/- was obtained by mutation of the parent L5178Y cell line which is described by, for example, Fischer et al., *Methods in Medical Research*, 1964, 10, 247]. The assay utilises a double layer soft-agar cloning technique similar to that described by Courtenay et al. (*British J. Cancer*, 1976, 34, 39). Each test compound is added at a range of concentrations to L5178Y TK-/- cells which have entered exponential growth phase in cell culture and the cells are incubated for 18 hours, harvested, washed with fresh culture medium and plated into soft-agar for clonogenic evaluation. After about 12 days colonies of cells are stained and counted.

Although the pharmacological properties of the quinazolines of the invention vary with structural changes, in general quinazolines of the invention posses activity in one or more of the above tests (a) to (d):

Test (a) $IC_{50}$ in the range, for example, 0.005–10 μM;
Test (b) $IC_{50}$ in the range, for example, 0.1–100 μM;
Test (c) $IC_{50}$ in the range, for example, 0.1–100 μM;
Test (d) The dose required to reduce the fraction of surviving cells to 10% of those treated lies in the range, for example, 1–100 μM.

In general those quinazolines of the invention which are especially preferred possess activity in one or more of the above tests (a) to (d):

Test (a) $IC_{50}$ in the range, for example, 0.005–2 μM;
Test (b) $IC_{50}$ in the range, for example, 0.1–10 μM;
Test (c) $IC_{50}$ in the range, for example, 0.1–10 μM;
Test (d) The dose required to reduce the fraction of surviving cells to 10% of those treated lies in the range, for example, 1–50 μM.

Thus, by way of example, N-diphenylmethyl-p-[N-(2-methyl-4-oxo-3,4-dihydroquinazolin-6-ylmethyl)-N-(prop-2-ynyl)amino]benzamide has an $IC_{50}$ of ~2 μM against thymidylate synthase [Test (a)], an $IC_{50}$ of ~7 μM against the L1210 cell line [Test (b)], and an $IC_{50}$ of ~1.5 μM against the MCF-7 cell line [Test (c)]; N-[p-[N-(2-methyl-4-oxo-3,4-dihydroquinazolin-6-ylmethyl)-N-(prop-2-ynyl)amino]benzoyl]-(3-nitrophenyl)glycine N-(4-methoxyphenylsulphonyl)amide has an $IC_{50}$ ~0.01 μM in Test (a), an $IC_{50}$ of ~25 μM in Test (b), and an $IC_{50}$ of ~1 μM in Test (c); and p-[N-(2,7-dimethyl-4-oxo-3,4-dihydroquinazolin-6-ylmethyl)-N-(prop-2-ynyl)amino[-N-[2-hydroxy-1-(3-nitrophenyl)ethyl]benzamide has an $IC_{50}$ of ~0.02 μM in Test (a), an $IC_{50}$ of ~3.4 μM in Test (b), and an $IC_{50}$ of ~0.1 μM in Test (c).

A quinazoline of the present invention may itself be active or it may be a pro-drug which is converted in vivo to an active compound.

A quinazoline of the invention, or a pharmaceutically-acceptable salt thereof, may be administered to a warm-blooded animal, including a human, in the form of a pharmaceutical composition which comprises the quinazoline, or a pharmaceutically-acceptable salt thereof, in association with a pharmaceutically-acceptable diluent or carrier.

The composition may be in a form suitable for oral administration, as a tablet or capsule, or, especially for parenteral injection (including intravenous, subcutaneous, intramuscular, intravascular or infusion), as a sterile solution, suspension or emulsion, or for topical administration, as an ointment or cream, or for rectal administration as a suppository.

The composition may contain, in addition to the quinazoline of the invention, one or more other anti-tumour substances, for example those selected from, for example, mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide; and biological response modifiers, for example interferon.

In general the above compositions may be prepared in a conventional manner using conventional excipients.

The quinazoline will normally be administered to a warm-blooded animal at a unit dose within the range 50–5000 mg per square meter body area of the animal, i.e. approximately 1–100 mg/kg, and this normally provides a therapeutically-effective dose. A unit dose form such as a tablet or capsule will usually contain, for example, 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage will be determined by the practitioner who is treating any particular patient.

According to a further feature of the present invention there is provided a method for producing an anti-tumour effect in a warm-blooded animal, such as man, in need of such treatment which comprises administering to said animal an effective amount of a quinazoline of the present invention, or a pharmaceutically-acceptable salt thereof. The invention also provides the use of a quinazoline of the present invention, or a pharmaceutically-acceptable salt thereof, in the manufacture of a novel medicament for use in the production of an anti-tumour effect in a warm blooded animal, such as man.

A quinazoline of the present invention is expected to possess a wide range of anti-tumour activities. CB3717 showed promising activity against human breast, ovarian and liver cancer and consequently it is expected that a quinazoline of the present invention will possess anti-tumour activity against these cancers. It is in addition expected that a quinazoline of the present invention will possess anti-tumour activity against a range of leukaemias, lymphoid malignancies and solid tumours such as carcinomas and sarcomas. Such tumours require thymidine monophosphate as one of the essential nucleotides for the synthesis of cellular DNA. In the presence of an effective amount of a thymidylate synthase inhibitor such as an effective amount of a quinazoline of the present invention it is expected that tumour growth will be inhibited.

As previously mentioned a quinazoline of the invention, or a pharmaceutically-acceptable salt thereof, is also of value in the treatment of, for example, allergic conditions such as psoriasis. In using a quinazoline of the invention for this purpose the compound will normally be administered at a dose within the range 50–5000 mg per square meter body area of the animal. In general for the treatment of an allergic condition such as psoriasis topical administration of a quinazoline of the invention is preferred. Thus, for example, for topical administration a daily dose in the range, for example, 1 to 50 mg/kg will be used.

The invention is illustrated but not limited by the following Examples in which unless otherwise stated:

(i) evaporations were carried out by rotary evaporation in vacuo and work-up procedures were carried out after removal of residual solids by filtration;

(ii) operations were carried out at laboratory temperature, that is in the range 18°–20° C. and under an atmosphere of an inert gas such as argon;

(iii) column chromatography (by the flash procedure) and medium pressure liquid chromatography (MPLC) were preformed on Merck Kieselgel silica (Art. 9385) or Merck Lichroprep RP-18 reverse-phase silica (Art. 9303) obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques [proton magnetic resonance spectra were determined using a Jeol FX 900 or a Bruker AM200 spectrometer operating at a field strength of 200 MHz; chemical shifts are reported in parts per million downfield from tetramethylsilane as an internal standard (δ scale) and peak multiplicities are shown thus: s, singlet; d, doublet; d of d's, doublet of doublet's; t, triplet, m, multiplet; fast-atom bombardment (FAB) mass spectral data were obtained using a VG Analytical MS9 spectrometer and xenon gas and, where appropriate, either positive ion data or negative ion data were collected];

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus, a Koffler hot plate apparatus or an oil-bath apparatus; and (viii) the following abbreviations have been used:
THF: tetrahydrofuran;
DMF: N,N-dimethylformamide.
DMA: N,N-dimethylacetamide;
DMSO: dimethylsulphoxide.

EXAMPLE 1

Oxalyl chloride (0.214 g) was added dropwise over 2 minutes to a cold (0°-5° C.), stirred solution of p-[N-(2-methyl-4-oxo-3-(pivaloyloxymethyl)-3,4-dihydroquinazolin-6-ylmethyl)-N-(prop-2-ynyl)amino]benzoic acid (0.504 g) in methylene chloride (13 ml) containing 4 drops of DMF. The pale yellow mixture was stirred at 0°-5° C. for 2 hours and then the solvent was evaporated in vacuo. The residue was suspended in dry methylene chloride (15 ml) and a mixture of (−)-(2R)-2-amino-2-phenylethanol (0.154 g) and triethylamine (0.34 g) was added. The solution was stirred at 20° C. for 16 hours. The solution was diluted with methylene chloride (40 ml), washed with water (2×20 ml), dried (MgSO₄) and evaporated. The residue was purified by chromatography on silica gel using increasingly polar mixtures of ethyl acetate and hexane as eluent.

A mixture of the product so obtained (0.46 g), ethanol (4 ml) and N aqueous sodium hydroxide solution (2 ml) was stirred at laboratory temperature under an atmosphere of argon for 2 hours. The ethanol was evaporated and the resulting aqueous solution was diluted with water (15 ml) and acidified to pH3 with N aqueous hydrochloric acid solution. The mixture was filtered and the solid residue was washed with water (3×10 ml) and dried in vacuo at 60° C. There was thus obtained p-[N-(2-methyl-4-oxo-3,4-dihydroquinazolin-6-ylmethyl)-N-(prop-2-ynyl)amino]-N-[(1R)-2-hydroxy-1-phenylethyl]benzamide (containing one equivalent of water; 0.382 g), m.p. 135°-137° C.

NMR Spectrum: (CD₃SOCD₃) 2.36 (s, 3H, CH₃), 3.16 (t, 1H, C≡CH), 3.55-3.75 (m, 3H, CH₂OH), 4.32 (broad s, 2H, CH₂C≡CH), 4.77 (s, 2H, CH₂N), 4.95-5.08 (m, 1H, CONHCH), 6.84 (d, 2H, aromatic), 7.15-7.40 (m, 5H, aromatic), 7.53 (d, 1H, aromatic), 7.65-7.81 (m, 3H, aromatic), 7.97 (d, 1H, aromatic), 8.27 (d, 1H, NH), 12.2 (broad s, 1H, NH);

Mass spectrum: (positive ion FAB) m/e (P+1) 467;

Elemental Analysis: Found C, 69.6; H, 5.7; N, 11.3; $C_{28}H_{26}N_4O_3$ 1H₂O requires C, 69.4; H, 5.8; N, 11.6%.

The p-[N-(2-methyl-4-oxo-3-(pivaloyloxymethyl)-3,4-dihydroquinazolin-6-ylmethyl)-N-(prop-2-ynyl)amino]benzoic acid used as a starting material above was obtained as follows:

A mixture of tert-butyl p-(prop-2-ynyl)aminobenzoate (16 g; European Patent Application No. 239362), 6-bromomethyl-2-methyl-4-oxo-3-(pivaloyloxymethyl)-3,4-dihydroquinazoline (80 g; European Patent Application No. 239362), 2,6-lutidine (10 ml) and N,N-dimethylacetamide (450 ml) was heated overnight to 55° C. under an atmosphere of argon. The mixture was poured into water (400 ml) and extracted with methylene chloride (2×300 ml). The organic extracts were combined, washed with water, dried (MgSO₄) and evaporated. The residue was purified by column chromatography on silica using initially a 7:3 v/v mixture of hexane and ethyl acetate and then a 1:1 v/v mixture of hexane and ethyl acetate as eluent.

A mixture of the product so obtained and trifluoroacetic acid (400 ml) was stirred at laboratory temperature for 40 minutes. The solvent was evaporated and the residue was purified by column chromatography on silica using initially a 9:1 v/v mixture of hexane and acetone, then a a 4:1 v/v mixture of hexane and acetone and finally methylene chloride as eluent. There was thus obtained p-[N-(2-methyl-4-oxo-3-(pivaloyloxymethyl)-3,4-dihydroquinazolin-6-ylmethyl)-N-(prop-2-ynyl)amino]benzoic acid (26.3 g).

EXAMPLE 2

The process described in Example 1 was repeated except that the appropriate amine was used in place of (−)-(2R)-2-amino-2-phenylethanol. Unless otherwise stated the starting materials were commercially available or prepared by conventional procedures and they were racemic mixtures. There were thus obtained the compounds described in the following table, the structures of which were confirmed by proton magnetic resonance and mass spectrometry and by elemental analysis.

TABLE I

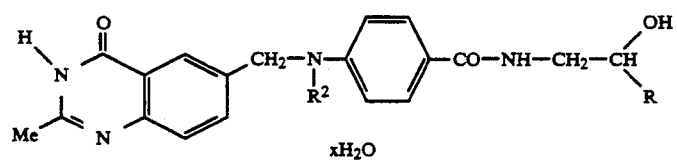

$xH_2O$

| Ex. 2 Compd. No. | R² | R | x | m.p. (°C.) |
| --- | --- | --- | --- | --- |
| 1 | prop-2-ynyl | phenyl | 2.5 | 158-161 |
| 2 | prop-2-ynyl | 4-chlorophenyl | 2.75 | 203-206 |
| 3ᵃ | prop-2-ynyl | 3-trifluoromethylphenyl | 0.5 | 185-188 |

TABLE I-continued

| | | 4-tolyl | 0.75 | 230–233 |
|---|---|---|---|---|
| 4[b] | prop-2-ynyl | | | |

NOTES

[a] The required amine, 2-hydroxy-2-(3-trifluoromethylphenyl)-ethylamine, was prepared from 3-trifluoromethylbenzaldehyde using the procedures described in J. Med. Chem., 1963, 6, 266.
[b] The required amine, 2-hydroxy-2-(4-tolyl)ethylamine, was prepared from 4-methylbenzaldehyde using similar procedures to those described in J. Med. Chem., 1963, 6, 266.

EXAMPLE 3

The process described in Example 1 was repeated except that the appropriate amine was used in place of (−)-(2R)-2-amino-2-phenylethanol. Unless otherwise stated the starting materials were commercially available or prepared by conventional procedures and they were racemic mixtures. There were thus obtained the compounds described in the following table, the structures of which were confirmed by proton magnetic resonance and mass spectrometry and by elemental analysis.

TABLE II

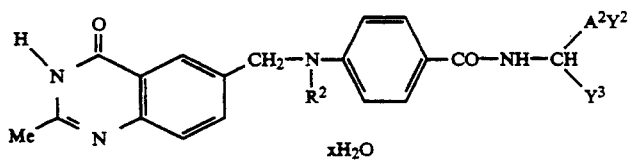

xH₂O

| Ex. 3 Compd. No. | R² | A² | Y² | Y³ | x | m.p. (°C.) |
|---|---|---|---|---|---|---|
| 1[a] | prop-2-ynyl | direct link | cyano | phenyl | 0.5 | 145–146 |
| 2[b] | prop-2-ynyl | CH₂ | phenylthio | phenyl | 0.5 | 187–189 |

NOTES a. The pivaloyloxymethyl protecting group was removed using the following procedure:

N-(α-cyano)benzyl-p-[N-(2-methyl-3-pivaloyloxymethyl-4-oxo-3,4-dihydroquinazolin-6-ylmethyl)-N-(prop-2-ynyl)amino]benzamide (0.43 g) was dissolved in methanol (10 ml) and aqueous N sodium carbonate solution (5 ml) was added followed by sufficient THF (approx. 5 ml) to give a homogeneous solution. The mixture was stirred for 72 hours under an atmosphere of argon and evaporated to dryness. The residue was extracted with hot methanol (3×10 ml). The combined methanol extracts were evaporated and the residue was triturated with ethyl acetate to remove residual starting material. The remaining solid was purified by column chromatography on silica using increasingly polar mixtures of ethyl acetate and methanol as eluent. There was thus obtained N-(α-cyanobenzyl)-p-[N-(2-methyl-4-oxo-3,4-dihydroquinazolin-6-ylmethyl)-N-(prop-2-ynyl)amino]benzamide as a white solid (0.063 g), m.p. 145°–146° C.

b. (1R)-1-Phenyl-2-phenylthioethylamine was used as the amine starting material. Its preparation was as follows:

(−)-(2R)-2-Amino-2-phenylethanol (5.0 g) was dissolved in DMF (50 ml) and N aqueous sodium hydroxide solution (36.4 ml) was added. Di-tert-butyl dicarbonate (8.75 g) was added and the solution was stirred vigorously at laboratory temperature for 72 hours. The mixture was evaporated and the residue was partitioned between ethyl acetate (200 ml) and water (200 ml). The aqueous layer was extracted with further portions of ethyl acetate (2×50 ml) and the combined organic extracts were washed with citric acid solution (10% w/w; 2×200 ml), water (200 ml) and brine (200 ml). Evaporation of the dried (MgSO₄) solution gave 2-(tert-butoxycarbonylamino)-2-phenylethanol (5.76 g) as a white solid, m.p. 137° C.

Methanesulphonyl chloride (0.33 ml) was added dropwise to a mixture of the material so obtained (1.0 g), triethylamine (0.65 ml) and methylene chloride (25 ml) which had been cooled to 0°–5° C. The mixture was stirred at 0°–5° C. for 30 minutes. The mixture was evaporated and the residue was partitioned between ethyl acetate (50 ml) and water (50 ml). The separated organic layer was washed with a saturated aqueous sodium bicarbonate solution (2×50 ml), brine (50 ml) and dried (MgSO₄). Evaporation gave a residue which was dissolved in DMF (10 ml) and a solution of sodium thiophenolate (0.558 g) in DMF (10 ml) was added. The mixture was stirred at 20° C. for 2 hours. The mixture was evaporated and the residue was partitioned between ethyl acetate and water. The organic layer was washed with brine (2×10 ml), dried (MgSO₄) and evaporated. There was thus obtained a white solid (0.50 g) which was dissolved in trifluoroacetic acid (5 ml) and stirred at 20° C. for 15 minutes. The mixture was evaporated to give (1R)-1-phenyl-2-phenylthioethylamine (0.52 g) as its trifluoroacetic acid salt.

EXAMPLE 4 p-[N-(2-Methyl-4-oxo-3,4-dihydroquinazolin-6-ylmethyl)-N-(prop-2-ynyl)amino]-N-(2-hydroxy-2-phenylethyl)benzamide (0.105 g) was dissolved in DMF (3 ml) and acetic anhydride (34 mg) and pyridine (37 mg) were added in turn. The mixture was stirred at 20° C. for 24 hours. The mixture was evaporated and the residue was triturated with water (5 ml). The solid was filtered off, washed with water and dried in air to give N-(2-acetoxy-2-phenylethyl)-p-[N-(2-methyl-4-oxo-3,4-dihydroquinazolin-6-ylmethyl)-N-(prop-2-ynyl)amino]benzamide (0.095 g; containing 1 equivalent of water), m.p. 203°–205° C.

NMR Spectrum: (CD₃SOCD₃) 2.04 (s, 3H, OCOCH₃), 2.33 (s, 3H, CH₃), 3.18 (t, 1H, C≡CH), 3.4–3.65 (m, 2H, NHCH₂), 4.30 (broad s, 2H, CH₂C≡C), 4.75 (s, 2H, CH₂N), 5.82–5.93 (m, 1H, CHOCO), 6.81 (d, 2H, aromatic), 7.28–7.40 (m, 5H, aromatic), 7.53 (d, 1H, aromatic), 7.63–7.75(m, 3H, aromatic), 7.96 (d, 1H, aromatic), 8.30 (broad t, 1H, CONH), 12.1 (broad s, 1H, NH);

Mass Spectrum: (positive ion FAB) m/e (P+1) 509; Elemental Analysis: Found C, 68.5; H, 5.4; N, 10.9; $C_{30}H_{28}N_4O_4$ $1H_2O$ requires C, 68.4; H, 5.7; N, 10.6%.

EXAMPLE 5

The process described in Example 4 was repeated except that the appropriate alcohol was used in place of p-[N-(2-methyl-4-oxo-3,4-dihydroquinazolin-6-ylmethyl)-N-(prop-2-ynyl)amino]-N-(2-hydroxy-2-phenylethyl)benzamide. There were thus obtained the compounds described in the following table, the structures of which were confirmed by proton magnetic resonance and mass spectrometry and by elemental analysis.

TABLE III

[Structural formula with $xH_2O$]

| Ex. 5 Compd. No. | $R^2$ | R | x | m.p. (°C.) |
|---|---|---|---|---|
| 1 | prop-2-ynyl | 3-trifluoromethylphenyl | 0.5 | 185–188 |
| 2 | prop-2-ynyl | 4-tolyl | 0.5 | 198–200 |

EXAMPLE 6 p-[N-2-Methyl-4-oxo-3,4-dihydroquinazolin-6-ylmethyl)-N-(prop-2-ynyl)amino]-N-[(2R)-2-(tert-butoxycarbonylamino)-2-phenylethyl]benzamide (0.30 g) was dissolved in trifluoroacetic acid (1 ml) and the solution was stirred at laboratory temperature for 30 minutes. Diethyl ether (10 ml) was added and the white solid was filtered off, washed with diethyl ether (3×5 ml) and dried. There was thus obtained N-[(2R)-2-amino-2-phenylethyl]-p-[N-(2-methyl-4-oxo-3,4-dihydroquinazolin-6-ylmethyl)-N-(prop-2-ynyl)amino]benzamide (0.25 g; containing 1.5 equivalents of water and 2.5 equivalents of trifluoroacetic acid), m.p. 128°–130° C.

NMR Spectrum: ($CD_3SOCD_3$) 2.37 (s, 3H, $CH_3$), 3.18 (broad s, 1H, C≡C), 3.50–3.80 (m, 3H, $CH_2NH$), 4.32 (broad s, 2H, $CH_2C≡C$), 4.40–4.55 (broad s, 1H, CHNH$_2$), 4.78 (s, 2H, $CH_2N$), 6.82 (d, 2H, aromatic), 7.36–7.50 (m, 5H, aromatic), 7.56 (d, 1H, aromatic), 7.66 (d, 2H, aromatic), 7.72 (doublet of doublets, 1H, aromatic), 7.96 (d, 1H, aromatic), 8.31 (t, 1H, $CH_2NH$), 8.4 (broad s, 3H, $NH_3$), 12.2 (broad s, CONH);

Mass Spectrum: (Positive ion FAB) m/e (P+1) 466;

Elemental Analysis: Found; C, 51.0; H, 4.0; N, 8.4; $C_{28}H_{27}N_5O_2$ $2.5CF_3COOH$ $1.5H_2O$ requires C, 51.0; H, 4.2; N, 9.0%.

The p-[N-(2-methyl-4-oxo-3,4-dihydroquinazolin-6-ylmethyl)-N-(prop-2-ynyl)amino]-N-[(2R)-2-(tert-butoxycarbonylamino)-2-phenylethyl]benzamide used as a starting material was obtained by repetition of the procedure described in Example 1 except that (2R)-(2-tert-butoxycarbonylamino)-2-phenylethylamine was used in place of (−)-(2R)-2-amino-2-phenylethanol. There was thus obtained the required starting material (containing 0.5 equivalents of water), m.p. 222°–224° C.

The (2R)-(2-tert-butoxycarbonylamino)-2-phenylethylamine required as a starting material was prepared as follows:

To a solution of (2R)-(2-tert-butoxycarbonylamino)-2-phenylethanol (0.5 g; prepared from (−)-(2R)-2-amino-2-phenylethanol using a similar process to that described in Note b. below Table II in Example 3) in methylene chloride (25 ml), cooled to 0°–5° C., was added triethylamine (0.32 ml) followed by mesyl chloride (0.16 ml). The mixture was stirred at 0°–5° C. for 30 minutes. The mixture was evaporated and the residue was partitioned between ethyl acetate (50 ml) and water (50 ml). The organic layer was washed with a saturated aqueous sodium bicarbonate solution (2×50 ml), brine (50 ml), dried ($MgSO_4$) and evaporated. The residue was dissolved in DMF (10 ml) and sodium azide (0.21 g) was added. The solution was heated to 50° C. under argon for 16 hours, cooled and evaporated to dryness. The residue was partitioned between ethyl acetate (50 ml) and water (50 ml) and the organic layer was washed with brine (25 ml), dried ($MgSO_4$) and evaporated. The residue so obtained (0.55 g) was dissolved in ethyl acetate (10 ml) and 10% palladium-on-charcoal catalyst (0.6 g) was added. The mixture was stirred for 16 hours under an atmosphere of hydrogen. The solution was filtered and evaporated to give the required starting material (0.5 g).

EXAMPLE 7 p-[N-(2-methyl-4-oxo-3,4-dihydroquinazolin-6-ylmethyl)-N-(prop-2-ynyl)amino]benzoic acid (0.5 g; European Patent Application No. 239362) was dissolved in DMSO (20 ml) and triethylamine (0.53 ml) and diphenylphosphoryl azide (0.35 ml) were added in turn. The mixture was stirred at 20° C. for 1.5 hours. Diphenylmethylamine (0.56 ml) was added and the mixture was stirred at 20° C. for 48 hours. The mixture was poured into water (100 ml), cooled to 5° C. and stirred for 15 minutes. The precipitated solid was filtered off, washed with water (3×10 ml) and dried in vacuo. There was thus obtained N-diphenylmethyl-p-[N-(2-methyl-4-oxo-3,4-dihydroquinazolin-6-ylmethyl)-N-(prop-2-ynyl)amino]benzamide (0.21 g; containing 0.7 equivalents of water), m.p. 227°–231° C.

NMR Spectrum: ($CD_3SOCD_3$) 2.33 (s, 3H, $CH_3$), 3.19 (broad s, 1H, C≡CH), 4.32 (broad s, 2H, $CH_2C≡C$), 4.77 (s, 2H, $CH_2N$), 6.37 (d, 1H, CONHCH), 6.84 (d, 2H, aromatic), 7.15–7.45 (m, 10H, aromatic), 7.53 (d, 1H, aromatic), 7.68 (1H, doublet of doublets, aromatic), 7.80 (d, 2H, aromatic), 7.96 (d, 1H, aromatic), 8.88 (d, 1H, CONHCH);

Mass Spectrum: (Negative ion FAB) m/e (P−1) 511;

Elemental Analysis: Found; C, 75.5; H, 5.6; N, 10.4; $C_{33}H_{28}N_4O_2$ $0.7H_2O$ requires; C, 75.6; H, 5.6; N, 10.6%.

EXAMPLE 8

The process described in Example 1 was repeated except that (R/S)-2-amino-2-methyl-3-phenylpropiononitrile (*Eur. J. Med. Chem. Clin. Ther.*, 1975, 10, 117) was used in place of (−)-(2R)-2-amino-2-phenylethanol and that the N-(2-cyano-1-phenylprop-2-yl)-p-[N-(2-methyl-4-oxo-3-(pivaloyloxymethyl)-3,4-dihydroquinazolin-6-ylmethyl)-N-(prop-2-ynyl)amino]benzamide so produced was dissolved in methanol which had been saturated with ammonia gas and the mixture was stirred at laboratory temperature for 24 hours. The mixture was evaporated to give N-(2-cyano-1-phenylprop-2-yl)-p-[N-(2-methyl-4-oxo-3,4-dihydroquinazolin-6-ylmethyl)-N-(prop-2-ynyl)amino]benzamide, m.p. 208°-209° C.

EXAMPLE 9

A mixture of pentafluorophenyl p-[N-(2-methyl-4-oxo-3-(pivaloyloxymethyl)-3,4-dihydroquinazolin-6-ylmethyl)-N-(prop-2-ynyl)amino]benzoate (0.381 g), α-(1,2-dihydro-2-oxopyrid-6-yl)benzylamine (0.13 g), triethylamine (0.51 ml), N-hydroxybenzotriazole (0.03 g) and DMF (20 ml) was stirred at laboratory temperature for 16 hours. The mixture was evaporated and the residue was triturated in diethyl ether. There was thus obtained p-[N-(2-methyl-4-oxo-3-(pivaloyloxymethyl)-3,4-dihydroquinazolin-6-ylmethyl)-N-(prop-2-ynyl)amino]-N-[α-(1,2-dihydro-2-oxopyrid-6-yl)benzyl]benzamide (0.22 g).

A mixture of the product so obtained, a saturated aqueous ammonium hydroxide solution (10 ml) and methanol (20 ml) was stirred at laboratory temperature for 16 hours. The mixture was concentrated by evaporation of the methanol. The precipitate was filtered off and dried. There was thus obtained p-[N-(2-methyl-4-oxo-3,4-dihydroquinazolin-6-ylmethyl)-N-(prop-2-ynyl)amino]-N-[α-(1,2-dihydro-2-oxopyrid-6-yl)benzyl]benzamide (0.11 g, 61%), m.p. 185°-190° C. (decomposes).

The pentafluorophenyl p-[N-(2-methyl-4-oxo-3-(pivaloyloxymethyl)-3,4-dihydroquinazolin-6-ylmethyl)-N-(prop-2-ynyl)amino]benzoate, used as a starting material, was obtained as follows:

Dicyclohexylcarbodiimide (6.18 g), was added to a suspension of p-[N-(2-methyl-4-oxo-3-(pivaloyloxymethyl)-3,4-dihydroquinazolin-6-ylmethyl)-N-(prop-2-ynyl)amino]benzoic acid (13.83 g) and pentafluorophenol (5.52 g) in ethyl acetate (450 ml) and the mixture was stirred at laboratory temperature for 18 hours. The mixture was filtered and the filtrate was evaporated. The residue was purified by column chromatography on silica gel using a 1:1 v/v mixture of hexane and ethyl acetate as eluent. There was thus obtained the required starting material (13.9 g), m.p. 143°-144° C.

The α-(1,2-dihydro-2-oxopyrid-6-yl)benzylamine used as a starting material was obtained as follows:

A Grignard reagent was prepared by heating together a mixture of bromobenzene (0.96 g), magnesium (0.146 g), diethyl ether (10 ml) and toluene (5 ml). A solution of 6-cyano-2-methoxypyridine (0.82 g) in a 1:1 v/v mixture of toluene and diethyl ether (10 ml) was added dropwise and the mixture was heated to reflux for 2 hours. The mixture was poured into a saturated aqueous ammonium chloride solution (50 ml) and extracted with diethyl ether (3×50 ml). The combined extracts were dried (MgSO4) and evaporated. The residue was purified by column chromatography using increasingly polar mixtures of toluene and ethyl acetate as eluent. There was thus obtained 2-methoxypyrid-6-yl phenyl ketone (0.71 g, 55%) as an oil.

NMR Spectrum (CD3SOCD3) 3.85 (s, 3H), 7.12 (d, 1H), 7.6 (m, 5H), 7.97 (t, 1H), 8.07 (d, 1H).

A mixture of aqueous ammonium hydroxide solution (specific gravity 0.91 g/ml, 6.25 ml) and formic acid (3.15 ml) was heated to 160° C. and the water was removed by distillation. 2-Methoxypyrid-6-yl phenyl ketone (0.71 g) was added and the mixture was heated to 165° C. for 22 hours. The mixture was allowed to cool to laboratory temperature, concentrated hydrochloric acid (25 ml) was added and the resultant mixture was heated to reflux for 8 hours. The mixture was evaporated. The residue was dissolved in water (10 ml) and the solution was basified by the addition of N aqueous sodium hydroxide solution. The mixture was filtered and the filtrate was extracted with ethyl acetate (2×20 ml). The combined extracts were dried (MgSO4) and evaporated. There was thus obtained the required starting material (0.13 g, 20%) as a gum.

NMR Spectrum (CD3SOCD3) 4.91 (s, 1H), 6.2 (m, 2H), 7.4 (m, 6H).

EXAMPLE 10

Oxalyl chloride (0.129 g) was added dropwise over 2 minutes to a cold (0°-5° C.), stirred solution of p-[N-(2-methyl-4-oxo-3-(pivaloyloxymethyl)-3,4-dihydroquinazolin-6-ylmethyl-N-(prop-2-ynyl)amino]benzoic acid (0.305 g) in methylene chloride (15 ml) containing 2 drops of DMF. The pale yellow mixture was stirred at 0°-5° C. for 2 hours and then the solvent was evaporated in vacuo. The residue was suspended in cold (0°-5° C.) methylene chloride (15 ml) and a mixture of (R/S)-(3-nitrophenyl)glycine N-(4-methoxyphenylsulphonyl)amide (0.252 g) and triethylamine (0.206 g) was added. The solution was stirred at 20° C. for 16 hours. The solution was diluted with methylene chloride (40 ml), washed with water (2×20 ml), dried (MgSO4) and evaporated. The residue was purified by chromatography on silica gel using increasingly polar mixtures of ethyl acetate and hexane as eluent to give N-[p-[N-(2-methyl-4-oxo-3-(pivaloyloxymethyl)-3,4-dihydroquinazolin-6-ylmethyl-N-(prop-2-ynyl)amino]benzoyl]-(3-nitrophenyl)glycine N-(4-methoxyphenylsulphonyl)amide (0.302 g).

After repetition of this reaction, a mixture of the product (0.40 g), ethanol (5 ml) and N aqueous sodium hydroxide solution (1 ml) was stirred at laboratory temperature under an atmosphere of argon for 2 hours. The ethanol was evaporated and the resulting aqueous solution was diluted with water (15 ml) and acidified to pH3 with N aqueous hydrochloric acid solution. The mixture was filtered and the solid residue was washed with water (3×10 ml) and dried in vacuo at 60° C. There was thus obtained N-[p-[N-(2-methyl-4-oxo-3,4-dihydroquinazolin-6-ylmethyl)-N-(prop-2-ynyl)amino]benzoyl]-(3-nitrophenyl)glycine N-(4-methoxyphenylsulphonyl)amide (containing 2.5 equivalents of water; 0.179 g), m.p. 169°-171° C.

NMR Spectrum: (CD3SOCD3) 2.33 (s, 3H, CH3), 3.14 (broad s, 1H, C≡CH), 3.84 (s, 3H, CH3), 4.32 (broad s, 2H, CH2), 4.78 (broad s, 2H, CH2), 5.21 (d, 1H, CHCO), 6.82 (d, 2H, aromatic), 7.03 (d, 2H, aromatic), 7.5-7.84 (m, 9H, aromatic), 7.96 (broad s, 1H, aromatic), 8.12-8.20 (m, 2H, aromatic), 8.70 (d, 1H, NH), 12.2 (broad s, 1H, NH);

Mass Spectrum: (positive ion FAB) m/e (P+1) 695;
Elemental Analysis: Found C, 56.5; H, 4.2; N, 10.9; C35H30N6O8S 2.5H2O requires C, 56.8; H, 4.7; N, 11.4%.

The (R/S)-(3-nitrophenyl)glycine N-(4-methoxyphenylsulphonyl)amide used as a starting material was prepared as follows:

(R/S)-(3-Nitrophenyl)glycine (5.00 g; *Acta Chem. Scand.*, 1963, 17, 2391) was dissolved in DMF (30 ml) and N aqueous sodium hydroxide solution (25.5 ml) and di-tert-butyl dicarbonate (6.4 ml) were added in turn. The mixture was stirred at 20° C. for 72 hours. The mixture was evaporated and the residue was dissolved in water (150 ml). The solution was acidified to pH3 by the addition of citric acid solution (20% w/w) and extracted with ethyl acetate (2×100 ml). The organic layer was washed with water (100 ml), with citric acid solution (10% w/w; 3×100 ml) and with water (3×100 ml). The solution was dried (MgSO₄) and evaporated to leave a pale yellow solid (5.37 g).

A solution of a portion (1 g) of the material so obtained in THF (10 ml) was added dropwise over 10 minutes to a solution of carbonyldiimidazole (0.546 g) in THF (10 ml). The mixture was stirred at laboratory temperature for 30 minutes and then heated to reflux for 30 minutes. The mixture was cooled to laboratory temperature and a solution of 4-methoxybenzenesulphonamide (0.631 g) in THF (10 ml) was added, followed 10 minutes later by a solution of 1,8-diazabicyclo-[5.4.0]undec-7-ene (0.513 g) in THF (10 ml). The deep red solution was stirred at 20° C. for 18 hours. N Hydrochloric acid solution (20 ml) was added and the mixture was partitioned between ethyl acetate (100 ml) and water (100 ml). The organic layer was combined with further ethyl acetate extracts (2×50 ml), dried (Na₂SO₄) and evaporated to give a yellow solid (0.96 g).

Trifluoroacetic acid (1 ml) was added to a solution of the compound so obtained (0.92 g) in methylene chloride (20 ml) and the mixture was stirred at 20° C. for 2.5 hours. The solution was evaporated and the residue was chromatographed on a silica gel column using increasingly polar mixtures of hexane, ethyl acetate and methanol as eluent to give the required starting material (0.53 g), m.p. 212°-213° C.

EXAMPLE 11

The process described in Example 10 was repeated except that the appropriate amine was used in place of (R/S)-(3-nitrophenyl)glycine N-(4-methoxyphenylsulphonyl)amide. Unless otherwise stated the starting materials were commercially available or prepared by conventional procedures and they were racemic mixtures. There were thus obtained the compounds described in the following table, the structures of which were confirmed by proton magnetic resonance and mass spectrometry and by elemental analysis.

a. The (S)-4-nitrophenylalanine N-methylamide used as a starting material was prepared as follows:

Thionyl chloride (5.73 g) was added dropwise to cold (0°-5° C.), stirred methanol (6 ml) at such a rate that the temperature did not rise above 5° C. The mixture was stirred at 0°-5° C. for 30 minutes and (S)-4-nitrophenylalanine (5.00 g) was added in three portions. The mixture was stirred for 18 hours and evaporated to leave a white solid (5.22 g). A solution of a portion of the product so obtained (0.91 g) in methanol (8 ml) was stirred at 20° C. whilst a solution of methylamine in water (25% w/w; 10 ml) was added. The mixture was stirred at 20° C. for 4 hours. The mixture was evaporated to leave the required starting material as a pale orange solid (0.89 g).

b. The (R/S)-(3-nitrophenyl)glycine N-(phenylsulphonyl)amide used as a starting material was obtained by repetition of the procedure described in the portion of Example 10 which is concerned with the preparation of starting materials except that benzenesulphonamide was used in place of 4-methoxybenzenesulphonamide.

The procedure described in Example 10 for the removal of the pivaloyloxymethyl protecting group was adjusted as follows:

A solution of (R/S)-N-[p-[N-(2-methyl-4-oxo-3-(pivaloyloxymethyl)-3,4-dihydroquinazolin-6-ylmethyl)-N-(prop-2-ynyl)amino]benzoyl]-(3-nitrophenyl)glycine N-(phenylsulphonyl)amide (0.163 g) in methanol (1 ml) was added to a saturated solution of ammonia gas in methanol (20 ml). The mixture was stirred at laboratory temperature for 42 hours. The mixture was filtered and evaporated. The residue was triturated under diethyl ether. There was thus obtained the required product (0.122 g), as a pale yellow solid.

c. The (R/S)-(3-nitrophenyl)glycine N-(methylsulphonyl)amide used as a starting material was obtained by repetition of the procedure described in the portion of Example 10 which is concerned with the preparation of starting materials except that methanesulphonamide was used in place of 4-methoxybenzenesulphonamide.

The procedure described in Example 10 for the removal of the pivaloyloxymethyl protecting group was adjusted as described in Note b. immediately above.

EXAMPLE 12

Triethylamine (0.1 g) and 1-hydroxybenzotriazole (5 mg) were added in turn to a mixture of pentafluorophenyl p-[N-(2-methyl-4-oxo-3-(pivaloyloxymethyl)-3,4-dihydroquinazolin-6-ylmethyl)-N-(prop-2-ynyl)amino]benzoate (0.2 g), (R/S)-3-nitro-α-(5-tetrazolyl)benzylamine hydrobromide (0.1 g) and DMF (5 ml) and the mixture was stirred at laboratory temperature for 18 hours. The mixture was evaporated in vacuo. The resi-

TABLE IV

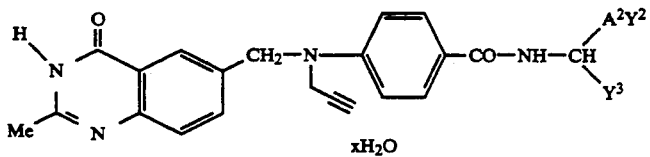

xH₂O

| Ex. 11 Compd. No. | A² | Y² | Y³ | x | m.p. (°C.) |
|---|---|---|---|---|---|
| 1ᵃ | CH₂ | 4-nitrophenyl | N-methylcarbamoyl | 3 | 260–262 |
| 2ᵇ | direct link | 3-nitrophenyl | N-phenylsulphonylcarbamoyl | 3 | 203–206 |
| 3ᶜ | direct link | 3-nitrophenyl | N-methylsulphonylcarbamoyl | — | 159–165 |

NOTES due was partitioned between ethyl acetate and water. The organic phase was washed with water, dried (MgSO4) and evaporated. The residue was triturated under diethyl ether. There was thus obtained p-[N-(2-methyl-4-oxo-3-(pivaloyloxymethyl)-3,4-dihydroquinazolin-6-ylmethyl)-N-(prop-2-ynyl)amino]-N-[3-nitro-α-(5-tetrazolyl)benzyl]benzamide (0.166 g), as an oil.

NMR Spectrum: (CD3CO2D) 1.21 (s, 9H), 2.36 (t, 1H), 2.72 (s, 3H), 4.21 (d, 2H), 4.78 (s, 2H), 6.15 (s, 2H), 6.85 (d, 2H), 7.18 (s, 1H), 7.5–7.6 (m, 1H), 7.7–7.86 (m, 5H), 8.2 (m, 2H), 8.35 (s, 1H).

A mixture of a portion (0.14 g) of the product so obtained and 2N aqueous sodium hydroxide solution (1.5 ml) was stirred at laboratory temperature for 1 hour. Water (3 ml) was added and the mixture was acidified by the addition of 2N aqueous hydrochloric acid solution. The mixture was filtered and the solid so obtained was washed with water and with diethyl ether and dried. There was thus obtained p-[N-(2-methyl-4-oxo-3,4-dihydroquinazolin-6-ylmethyl)-N-(prop-2-ynyl)amino]-N-[3-nitro-α-(5-tetrazolyl)benzyl]benzamide (0.094 g), as a pale yellow solid.

NMR Spectrum: (CD3SOCD3) 2.38 (s, 3H), 3.19 (d, 1H), 4.35 (d, 2H), 4.8 (s, 2H), 6.86 (q, 2H), 7.55–8.03 (m, 8H), 8.2 (m, 1H), 8.4 (t, 1H), 9.37 (m, 1H).

The (R/S)-3-nitro-α-(5-tetrazolyl)benzylamine hydrobromide used as a starting material was obtained as follows:

(R/S)-(3-Nitrophenyl)glycine (5.88 g) was added to a solution of potassium bicarbonate (6 g) in water (140 ml) and the suspension so formed was heated on a steam bath to form a solution. The solution was cooled to laboratory temperature, benzyl chloroformate (6.2 g) was added and the mixture was stirred at laboratory temperature for 18 hours. The mixture was extracted with diethyl ether (3×50 ml). The aqueous layer was acidified by the addition of 2N aqueous hydrochloric acid solution and an ethyl acetate extract was taken. The organic layer was washed with water, dried (MgSO4) and evaporated to give N-(benzyloxycarbonyl)-(3-nitrophenyl)glycine (7.84 g), as a yellow solid.

After repetition of the above reaction a mixture of the product so obtained (15 g), triethylamine (4.6 g) and THF (200 ml), was cooled to −15° C. A solution of isobutyl chloroformate (6.2 g) in THF (30 ml) was added dropwise and the mixture was stirred at −15° C. for 20 minutes. Ammonia gas was led into the mixture during a period of 1 hour and the mixture was cooled to 0° C. The mixture was allowed to stand at laboratory temperature for 16 hours and then evaporated. The residue was triturated under a mixture of methanol and water. The solid so obtained was purified by column chromatography on silica gel using a 19:1 v/v mixture of chloroform and methanol as eluent. There was thus obtained N-(benzyloxycarbonyl)-(3-nitrophenyl)glycine amide (3.12 g), as a solid.

A solution of phosphorus oxychloride (2.3 g) in methylene chloride (15 ml) was added to a mixture of the product so obtained and pyridine (30 ml) which had been cooled to −5° C. The mixture was stirred at 0° C. for 1 hour. The mixture was partitioned between ethyl acetate and water. The organic layer was washed with dilute hydrochloric acid, and with water, dried (Na2SO4) and evaporated. The residue was purified by column chromatography using a 3:1 v/v mixture of hexane and ethyl acetate as eluent. There was thus obtained N-(benzyloxycarbonyl)-(3-nitrophenyl)glycinonitrile (1.96 g), m.p. 96°–99° C.

A portion (1.8 g) of the product so obtained was added to a mixture of sodium azide (0.34 g), ammonium chloride (0.42 g) and DMF (10 ml) and the mixture so obtained was heated to 95° C. for 18 hours. The mixture was filtered and evaporated in vacuo. The residue was suspended in water and acidified to pH1 by the addition of dilute hydrochloric acid. The mixture was extracted with ethyl acetate. The organic layer was washed with water, dried (MgSO4) and evaporated to leave a light yellow solid (1.71 g).

The product so obtained was added to a solution of hydrobromic acid in acetic acid (48% v/v; 5 ml) which had been cooled to 5° C. The mixture was stirred at laboratory temperature for 1 hour. Diethyl ether (50 ml) was added and the mixture was stirred. The supernatant was decanted from a gum which had been deposited. The residual gum was triturated under diethyl ether to give (R/S)-3-nitro-α-(5-tetrazolyl)benzylamine hydrobromide (1.09 g), as an orange solid.

NMR Spectrum (CD3SOCD3) 6.47 (s, 1H), 7.82 (t, 1H), 8.0 (m, 1H), 8.35 (m, 1H), 8.55 (m, 1H), 9.5 (broad s, 3H).

EXAMPLE 13

The process described in Example 12 was repeated except that the appropriate pentafluorophenyl benzoate and the appropriate amine were used. Unless otherwise stated the starting materials were racemic mixtures. There were thus obtained the compounds described in the following Table, the structures of which were confirmed by proton magnetic resonance and mass spectrometry and by elemental analysis.

TABLE V

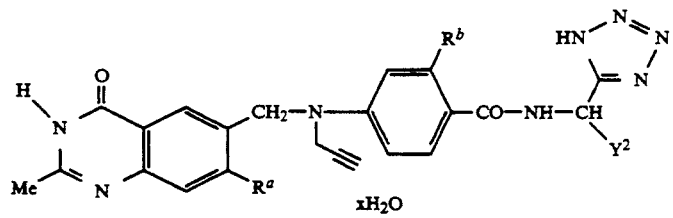

| Ex. 13. Compd. No. | $R^a$ | $R^b$ | $Y^2$ | x | m.p. (°C.) |
| --- | --- | --- | --- | --- | --- |
| 1[a] | methyl | H | 3-nitrophenyl | — | 229–233 |
| 2[b] | fluoro | H | 3-nitrophenyl | 0.3 | — |
| 3[c] | H | fluoro | 3-nitrophenyl | — | — |

TABLE V-continued

| | | | | | |
|---|---|---|---|---|---|
| 4[d] | H | H | phenyl | — | 210–212 |

NOTES a. The p-[N-(2,7-dimethyl-4-oxo-3-(pivaloyloxymethyl)-3,4-dihydroquinazolin-6-ylmethyl)-N-(prop-2-ynyl)amino]benzoic acid used in the preparation of the appropriate pentafluorophenyl benzoate starting material was prepared as follows 2,6,7-Trimethyl-3,4-dihydroquinazolin-4-one (European Patent Specification No. 0284338) was reacted with chloromethyl pivalate using the procedure described in European Patent Specification No. 0239362 for the corresponding reaction of 2,6-dimethyl-3,4-dihydroquinazolin-4-one. There was thus obtained 3-(pivaloyloxymethyl)-2,6,7-trimethyl-3,4-dihydroquinazolin-4-one. The product so obtained was reacted with N-bromosuccinimide in the presence of benzoyl peroxide using the procedure described in European Patent Specification No. 0284338 to give 6-bromomethyl-2,7-dimethyl-3-(pivaloyloxymethyl)-3,4-dihydroquinazolin-4-one in 57% yield, m.p. 149°–152° C.

Using the procedure described in the portion of Example 1 which is concerned with the preparation of p-[N-(2-methyl-4-oxo-3-(pivaloyloxymethyl)-3,4-dihydroquinazolin-6-ylmethyl)-N-(prop-2-ynyl)amino]benzoic acid the material so obtained was converted into the required benzoic acid, in 70% yield, m.p. 226° C. (decomposes).

b. The product, which also contained 0.3 equivalents of diethyl ether and 1.5 equivalents of sodium, gave the following NMR data (CD$_3$SOCD$_3$) 2.32 (s, 3H), 3.16 (t, 1H), 4.32 (d, 2H), 4.78 (s, 2H), 6.54 (s, 1H), 6.87 (d, 1H), 7.37 (d, 1H), 7.58 (t, 1H), 7.77–7.96 (m, 3H), 8.07 (q, 1H), 8.28(s, 1H), 8.83 (d, 1H).

The p-[N-(7-fluoro-2-methyl-4-oxo-3-(pivaloyloxymethyl)-3,4-dihydroquinazolin-6-ylmethyl)-N-(prop-2-ynyl)amino]benzoic acid used in the preparation of the appropriate pentafluorophenyl benzoate starting material is described in copending European Patent Application No. 89312986.6 (to be published as European Patent Application No. 0373891).

c. The product displayed the following NMR data: (CD$_3$SOCD$_3$) 2.35 (s, 3H), 3.25 (s, 1H), 4.39 (s, 2H), 4.84 (s, 2H), 6.58 (t, 2H), 6.73 (d, 1H), 7.52–7.88 (m, 4H), 7.95 (d, 1H), 8.01 (s, 1H), 8.2 (d, 1H), 8.42 (s, 1H), 9.19 (d, 1H).

The o-fluoro-p-[N-(2-methyl-4-oxo-3-(pivaloyloxymethyl)-3,4-dihydroquinazolin-6-ylmethyl)-N-(prop-2-ynyl)amino]benzoic acid used in the preparation of the appropriate pentafluorophenyl benzoate starting material was obtained from 6-bromomethyl-2-methyl-3-(pivaloyloxymethyl)-3,4-dihydroquinazolin-4-one using the procedures described in the portion of Example 1 which is concerned with the preparation of starting materials except that tert-butyl o-fluoro-p-(prop-2-ynyl)aminobenzoate [prepared in 56% yield by the reaction of tert-butyl p-amino-o-fluorobenzoate (copending European Patent Application No. 89312986.6) with propargyl bromide] was used in place of tert-butyl p-(prop-2-ynyl)aminobenzoate.

d. The product, which contained 0.25 equivalents of trifluoroacetic acid, was obtained by repetition of the procedure described in the first paragraph of Example 12 except that p-[N-(2-methyl-4-oxo-3,4-dihydroquinazolin-6-ylmethyl)-N-(prop-2-ynyl)amino]benzoyl azide was used in place of pentafluorophenyl p-[N-(2-methyl-4-oxo-3-(pivaloyloxymethyl)-3,4-dihydroquinazolin-6-ylmethyl)-N-(prop-2-ynyl)amino]benzoate, (R/S)-α-(5-tetrazolyl)benzylamine was used in place of (R/S)-3-nitro-α-(5-tetrazolyl)benzylamine and no 1-hydroxybenzotriazole was added.

The p-[N-(2-methyl-4-oxo-3,4-dihydroquinazolin-6-ylmethyl)-N-(prop-2-ynyl)amino]benzoyl azide, used as a starting material, was obtained as follows:

Diphenylphosphoryl azide (2.80 ml) and triethylamine (3.59 ml) were added successively to a mixture of p-[N-(2-methyl-4-oxo-3,4-dihydroquinazolin-6-ylmethyl)-N-(prop-2-ynyl)amino]benzoic acid (as its trifluoroacetic acid salt; 3.0 g; European Patent Specification No. 0239362), and DMF (35 ml) which had been cooled to approximately 5° C. by immersion in an ice bath. The mixture was stirred at 5° C. for 3 hours and allowed to stand at 5° C. overnight. The precipitated solid was filtered off, washed in turn with DMF and diethyl ether and dried. There was thus obtained the required starting material (2.10 g).

NMR Spectrum: (CD$_3$SOCD$_3$) 2.33 (s, 3H, CH$_3$), 3.24 (t, 1H, C≡C), 4.40 (broad s, 2H, CH$_2$), 4.85 (s, 2H, CH$_2$), 6.89 (d, 2H, aromatic), 7.54 (d, 1H, aromatic), 7.67 (d of d's, 1H, aromatic), 7.78 (d, 2H, aromatic), 7.95 (d, 1H, aromatic), 12.2 (broad s, 1H, NH);

Mass Spectrum: m/e (P) 372.

The (R/S)-α-(5-tetrazolyl)benzylamine used as a starting material was obtained by repetition of the procedure described in the portion of Example 12 which is concerned with the preparation of (R/S)-3-nitro-α-(5-tetrazolyl)benzylamine except that (R/S)-phenylglycine was used as the starting material in place of (R/S)-(3-nitrophenyl)glycine.

EXAMPLE 14

The process described in Example 1 was repeated except that, where necessary, the appropriate benzoic acid was used in place of p-[N-(2-methyl-4-oxo-3-(pivaloyloxymethyl)-3,4-dihydroquinazolin-6-ylmethyl)-N-(prop-2-ynyl)amino]benzoic acid and the appropriate amine was used in place of (−)-(2R)-2-amino-2-phenylethanol. Where an appropriate amine was available as a salt such as a trifluoroacetic acid salt then an extra equivalent of triethylamine was added. Unless otherwise stated the starting materials were racemic mixtures. There were thus obtained the compounds described in the following table, the structures of which were confirmed by proton magnetic resonance and mass spectrometry and by elemental analysis.

TABLE VI

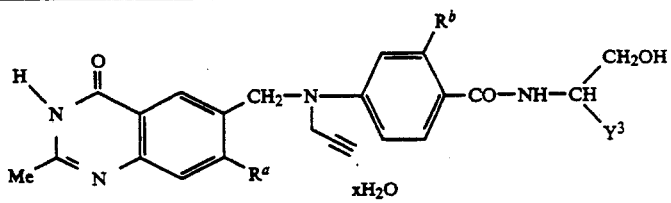

Ex. 14

| Compd. No. | R$^a$ | R$^b$ | Y$^3$ | x | m.p. (°C.) |
|---|---|---|---|---|---|
| 1$^a$ | H | H | 3-nitrophenyl | 2 | 163–167 |
| 2 | Me | H | 3-nitrophenyl | 3 | 155–158 |
| 3$^b$ | H | H | α-hydroxy-4-nitrobenzyl | 1.9 | 185–188 |
| 4$^c$ | H | H | 2-thienyl | 1 | 122–124 |
| 5$^d$ | H | F | 3-nitrophenyl | — | 130–135 |
| 6$^e$ | Me | F | 3-nitrophenyl | — | 124–127 |

NOTES a. The 2-amino-2-(3-nitrophenyl)ethanol, used as a starting material, was obtained as follows:

(R/S)-(3-Nitrophenyl)glycine was reacted with di-tert-butyl dicarbonate using the procedure described in the first paragraph of the portion of Example 10 which is concerned with the preparation of starting materials to give (R/S)-N-(tert-butoxycarbonyl)-(3-nitrophenyl)glycine.

A portion (3.07 g) of the product so obtained was dissolved in DMF (25 ml) and potassium carbonate (1.43 g) and methyl iodide (1.87 ml) were added in turn. The mixture was stirred at laboratory temperature for 72 hours. The mixture was evaporated and the residue was partitioned between ethyl acetate and water. The organic phase was washed with water and with brine, dried (MgSO$_4$) and evaporated to give (R/S)-N-(tert-butoxycarbonyl)-(3-nitrophenyl)glycine methyl ester (3.23 g).

The material so obtained (3.23 g) was dissolved in THF (5 ml) and added dropwise over 15 minutes to a solution of anhydrous lithium chloride (0.89 g) and sodium borohydride (0.80 g) in THF (20 ml). The mixture was stirred for 1 hour at laboratory temperature and then ethanol (60 ml) was added. The mixture was stirred at laboratory temperature overnight and the bulk of the solvents were evaporated. Hydrochloric acid (1N aqueous) was added to bring the pH to 4 and the mixture was extracted with ethyl acetate. The organic phase was washed with water, dried (MgSO$_4$) and evaporated to give (R/S)-2-(tert-butoxycarbonylamino)-2-(3-nitrophenyl)ethanol (3.11 g), m.p. 96°–98° C.

Trifluoroacetic acid (3 ml) was added to a solution of a portion (0.66 g) of the material so obtained in methylene chloride (5 ml) and the mixture was stirred at laboratory temperature for 1 hour. The mixture was evaporated and the residue was triturated under diethyl ether. There was thus obtained the required starting material as its trifluoroacetic acid salt (0.59 g).

b. The (2R)-2-amino-1-(4-nitrophenyl)propane-1,3-diol, used as a starting material, was obtained as follows:

A mixture of D-threo-N-dichloroacetyl-1-(4-nitrophenyl)-2-aminopropane-1,3-diol (Chloramphenicol, 10.2 g) and 1N aqueous hydrochloric acid (140 ml) was heated on a steam bath for 4 hours. The mixture was concentrated to a volume of approximately 30 ml and basified to pH9 by the addition of 2N aqueous sodium hydroxide solution. The precipitate was isolated, washed with cold water and dried to give the required starting material (2.29 g), m.p, 156°–159° C.

c. The (R/S)-2-amino-2-(2-thienyl)ethanol, used a starting material, was obtained as follows:

The procedures described in Note a. immediately above were repeated except that (R/S)-2-thienylglycine was used in place of (R/S)-(3-nitrophenyl)glycine. There was thus obtained the required starting material as its trifluoroacetic acid salt.

NMR Spectrum (CD$_3$SOCD$_3$) 3.78 (m, 2H), 4.64 (m, 1H), 5.69 (broad s, 3H), 7.07 (d of d's, 1H), 7.28 (d of d's, 1H), 7.58 (d of d's, 1H).

d. The product was purified by chromatography on reverse-phase silica gel using a 45:55:0.2 v/v mixture of methanol, water and trifluoroacetic acid as eluent. The product was obtained bearing 0.67 equivalents of trifluoroacetic acid.

e. In this preparation the treatment with N aqueous sodium hydroxide solution to remove the pivaloyloxymethyl group was replaced by treatment of the appropriate intermediate with a saturated solution of ammonia gas in methanol.

The product was purified by chromatography on reverse-phase silica gel using decreasingly polar mixtures of methanol, water and trifluoroacetic acid as eluent. The product was obtained bearing 1.3 equivalents of trifluoroacetic acid.

The p-[N-(2,7-dimethyl-4-oxo-3-(pivaloyloxymethyl)-3,4-dihydroquinazolin-6-ylmethyl)-N-(prop-2-ynyl)amino]-o-fluorobenzoic acid, used as a starting material, was obtained as follows:

A mixture of 6-bromomethyl-2,7-dimethyl-3-(pivaloyloxymethyl)-3,4-dihydroquinazolin-4-one (0.9 g), tert-butyl o-fluoro-p-(prop-2-ynyl)aminobenzoate (0.882 g), potassium carbonate (0.691 g), 18-crown-6 (0.005 g) and N-methylpyrrolidin-2-one (20 ml) was stirred and heated to 90° C. for 6 hours. The mixture was evaporated and the residue was partitioned between ethyl acetate and water. The organic phase was washed with water and brine, dried (MgSO$_4$) and evaporated. The residue was purified by chromatography on silica gel using increasingly polar mixtures of methylene chloride and ethyl acetate as eluent.

A mixture of the product so obtained (0.9 g) and trifluoroacetic acid (20 ml) was stirred at laboratory temperature for 1 hour. The mixture was evaporated and the residue was triturated under diethyl ether. There was thus obtained the required starting material as a solid (0.64 g).

Elemental Analysis Found C, 64.7; H, 5.5; N, 8.2; $C_{27}H_{28}FN_3O_5 \cdot 0.1CF_3CO_2H$ requires C, 64.7; H, 5.6; N, 8.3%.

EXAMPLE 15

The process described in Example 1 was repeated except that the appropriate amine was used in place of (−)-(2R)-2-amino-2-phenylethanol. Unless otherwise stated the starting materials were commercially available or prepared by conventional procedures and they were racemic mixtures. There was thus obtained the compounds described in the following table, the structures of which were confirmed by proton magnetic resonance and mass spectrometry and by elemental analysis.

TABLE VII

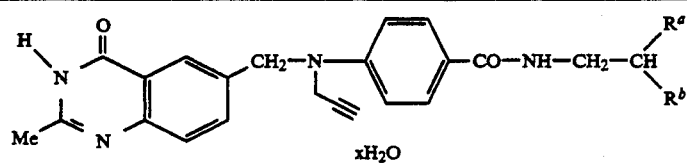

| Ex. 15 Compd. No. | $R^a$ | $R^b$ | x | m.p. (°C.) |
|---|---|---|---|---|
| 1[a] | 4-nitrophenyl | hydroxy | 4 | 264–267 |
| 2[b] | phenyl | methylsulphinyl | 5 | 128–133 |
| 3[c] | phenyl | methylsulphonyl | 1.5 | 131–134 |

NOTES a. The 2-amino-1-(4-nitrophenyl)ethanol, used as a starting material, was obtained as follows:

A mixture of 4-nitrophenacyl bromide (24.4 g), hexamethylenetetramine (16 g) and toluene (500 ml) was heated on a steam bath for 1 hour and then allowed to stand at laboratory temperature for 16 hours. The precipitate was washed with ice-cold ethanol. A mixture of the solid so obtained, concentrated hydrochloric acid (120 ml) and ethanol (150 ml) was stirred at laboratory temperature until a clear solution was obtained. The mixture was allowed to stand overnight at laboratory temperature. The precipitate (33 g) was isolated.

A solution of sodium borohydride (10 g) in dilute aqueous sodium hydroxide solution (75 ml) was added dropwise to a solution of the product so obtained in 1,4-dioxan (175 ml) which had been cooled to 0° C. The mixture was stirred at laboratory temperature for 16 hours. Water (50 ml) was added and the mixture was acidified by the addition of concentrated hydrochloric acid. The acidic solution was washed with ethyl acetate, basified by the addition of dilute sodium hydroxide solution and extracted with ethyl acetate. The organic layer was washed with water, dried (MgSO4) and evaporated. The residue was recrystallised from toluene. There was thus obtained the required starting material (2.7 g), m.p. 127°–133° C.

b. In this preparation the treatment with N aqueous sodium hydroxide solution to remove the pivaloyloxymethyl group was replaced by treatment of the appropriate intermediate with a saturated solution of ammonia gas in methanol.

The 2-methylsulphinyl-2-phenylethylamine, used as a starting material, was obtained as follows:

Mesyl chloride (0.54 ml) was added dropwise to a mixture of 2-(tert-butoxycarbonylamino)-1-phenylethanol (1.5 g), triethylamine (2.64 ml) and methylene chloride (45 ml) which was cooled in an ice-bath to °C. The mixture was stirred at °C. for 1 hour. The mixture was washed with a cold saturated aqueous sodium bicarbonate solution and with water, dried (MgSO4) and evaporated. The mesylate so obtained was added to a solution of sodium methanethiolate (0.66 g) in DMF (10 ml) and the mixture was stirred at laboratory temperature for 18 hours. The mixture was evaporated and the residue was purified by chromatography on silica gel using increasingly polar mixtures of hexane and ethyl acetate as eluent. There was thus obtained N-(tert-butoxycarbonyl)-2-methylthio-2-phenylethylamine (0.98 g) as an oil.

A solution of a portion (0.86 g) of the material so obtained in methanol (20 ml) was cooled to 10° C. and a solution of sodium metaperiodate (0.65 g) in warm water (2.5 ml) was added dropwise over 15 minutes. The mixture was stirred at laboratory temperature for 1 hour. The thick white precipitate was filtered off and the solution was evaporated to dryness. The residue was taken up in ethyl acetate (30 ml), washed with water and dried (MgSO4). The organic phase was evaporated to give N-(tert-butoxycarbonyl)-2-methylsulphinyl-2-phenylethylamine (0.84 g).

A mixture of a portion (0.32 g) of the material so obtained, trifluoroacetic acid (2 ml) and methylene chloride (10 ml) was stirred at laboratory temperature for 1.5 hours. The mixture was evaporated to give the required starting material (0.27 g) as a gum.

NMR Spectrum ($CD_3SOCD_3$) 2.19 and 2.41 (2 s's, 3H), 3.5–3.7 (m, 2H), 4.17 and 4.22 (m, 1H), 7.35–7.50 (m, 5H), 8.0–8.3 (broad s, 3H).

c. The 2-methylsulphonyl-2-phenylethylamine, used as a starting material, was obtained as follows:

A solution of 3-chloroperbenzoic acid (0.52 g of material of 80% purity) in methylene chloride (30 ml) was added dropwise to a stirred solution of N-(tert-butoxycarbonyl)-2-methylsulphinyl-2-phenylethylamine (0.62 g) in methylene chloride (20 ml). The mixture was stirred at laboratory temperature for 18 hours. The mixture was washed in turn with a 5% w/v aqueous solution of sodium metabisulphite, with a saturated aqueous sodium bicarbonate solution and with water, dried (MgSO4) and evaporated.

A mixture of the material so obtained (0.66 g), trifluoroacetic acid (2 ml) and methylene chloride (20 ml) was stirred at laboratory temperature for 2 hours. The mixture was evaporated. There was thus obtained the required starting material as its trifluoroacetic acid salt (0.69 g).

EXAMPLE 16

Using an analogous procedure to that described in Example 4, N-[2-hydroxy-1-(3-nitrophenyl)ethyl]-p-[N-

(2-methyl-4-oxo-3,4-dihydroquinazolin-6-ylmethyl)-N-(prop-2-ynyl)amino]benzamide was reacted with acetic anhydride to give N-[2-acetoxy-1-(3-nitrophenyl)ethyl]-p-[N-(2-methyl-4-oxo-3,4-dihydroquinazolin-6-ylmethyl)-N-(prop-2-ynyl)amino]benzamide (containing 2 equivalents of water) in 56% yield, m.p. 133°-135° C.

EXAMPLE 17

Using an analogous procedure to that described in Example 4, N-[2-hydroxy-2-(4-nitrophenyl)ethyl]-p-[N-(2-methyl-4-oxo-3,4-dihydroquinazolin-6-ylmethyl)-N-(prop-2-ynyl)amino]benzamide was reacted with acetic anhydride to give N-[2-acetoxy-2-(4-nitrophenyl)ethyl]-p-[N-(2-methyl-4-oxo-3,4-dihydroquinazolin-6-ylmethyl)-N-(prop-2-ynyl)amino]benzamide (containing 2.3 equivalents of water) in 88% yield, m.p. 198°-203° C.

EXAMPLE 18

Using an analogous procedure to that described in Example 12, pentafluorophenyl p-[N-(2-methyl-4-oxo-3-(pivaloyloxymethyl)-3,4-dihydroquinazolin-6-ylmethyl)-N-(prop-2-ynyl)amino]benzoate was reacted with (R)-(−)-2-amino-3-phenylpropanol to give N-(1-hydroxy-3-phenylprop-2-yl)-p-[N-(2-methyl-4-oxo-3,4-dihydroquinazolin-6-ylmethyl)benzamide (containing 1 equivalent of sodium chloride) in 42% yield, m.p. 165°-167° C.

EXAMPLE 19

A mixture of pentafluorophenyl p-[N-(2-methyl-4-oxo-3-(pivaloyloxymethyl)-3,4-dihydroquinazolin-6-ylmethyl)-N-(prop-2-ynyl)amino]benzoate (0.49 g), 2-amino-2-(4-fluorophenyl)ethanol trifluoroacetic acid salt (0.2 g), triethylamine (0.54 ml), N-hydroxybenzotriazole (0.04 g) and ethyl acetate (10 ml) was stirred at laboratory temperature for 24 hours. The mixture was evaporated and the residue was purified by chromatography on silica gel using increasingly polar mixtures of hexane and ethyl acetate as eluent.

A mixture of the product so obtained (0.19 g), a saturated solution of ammonia gas in methanol (5 ml) and methanol (2 ml) was stirred at laboratory temperature for 48 hours. The mixture was evaporated and the solid so obtained was dried in vacuo at 60° C. for 3 hours. There was thus obtained N-[1-(4-fluorophenyl)-2-hydroxyethyl]-p-[N-(2-methyl-4-oxo-3,4-dihydroquinazolin-6-ylmethyl)-N-(prop-2-ynyl)amino]benzamide (containing 1.5 equivalents of water, 0.15 g), m.p. 100°-103° C.

NMR Spectrum: (CDCl$_3$) 2.33 (s, 3H, CH$_3$), 3.17 (t, 1H, C≡CH), 3.55-3.75 (m, 2H, CH$_2$OH), 4.30 (d, 2H, CH$_2$Ar), 4.70-4.90 (m, 3H, CH$_2$N+OH), 4.95-5.07 (m, 1H, NHCH), 6.83-7.74 (m, 4H, aromatic), 7.09 (t, 2H, aromatic), 7.35-7.45 (m, 2H, aromatic), 7.52 (d, 1H, aromatic), 7.68 (d of d's, 1H, aromatic), 7.96(d, 1H, aromatic), 8.27 (d, 1H, CONH), 12.13 (broad s, 1H, NH);

Mass Spectrum: (positive ion FAB) m/e (P+1) 485;

Elemental Analysis: Found: C, 65.5; H, 5.2; N, 11.0; C$_{28}$H$_{25}$FN$_4$O$_3$ 1.5H$_2$O requires C, 65.7; H, 5.5; N 11.0%.

The 2-amino-2-(4-fluorophenyl)ethanol trifluoroacetic acid salt, used as a starting material was obtained from 4-fluorophenylglycine using an analogous procedure to that described in Note a. below Table VI in Example 14.

EXAMPLE 20

The process described in Example 19 was repeated except that the appropriate amine was used in place of 2-amino-2-(4-fluorophenyl)ethanol. Unless otherwise stated the starting materials were racemic mixtures. There were thus obtained the compounds described in the following table, the structures of which were confirmed by proton magnetic resonance and mass spectrometry and by elemental analysis.

TABLE VIII $$\text{structure with } A^2Y^2, A^3Y^3 \text{ substituents} \cdot xH_2O$$

| Ex. 20 Compd. No. | A$^2$ | Y$^2$ | A$^3$ | Y$^3$ | x | m.p. (°C.) |
|---|---|---|---|---|---|---|
| 1$^a$ | direct link | phenyl | CH$_2$ | mesyl | 1.5 | 254–256 |
| 2$^b$ | direct link | 3-nitrophenyl | CH$_2$S | 1,2,4-triazol-3-yl | — | 149–157 |
| 3$^c$ | CH$_2$ | dimethylamino | direct link | 3-nitrophenyl | 2 | 235–237 |
| 4$^d$ | direct link | phenyl | direct link | 4-methylthiazol-2-yl | 0.5 | 223–235 |
| 5$^e$ | CH$_2$ | tert-butoxy | direct link | 4-methylthiazol-2-yl | — | 174–175 |
| 6$^f$ | CH$_2$ | hydroxy | direct link | 4-methylthiazol-2-yl | 0.75 | 254–256 |
| 7$^g$ | CH$_2$CH$_2$ | hydroxy | direct link | 3-nitrophenyl | 0.75 | 208–213 |

NOTES a. The (1R)-2-mesyl-1-phenylethylamine, used as a starting material, was obtained as follows:

Mesyl chloride (0.54 ml) was added dropwise to a mixture of (R)-(−)-2-(tert-butoxycarbonylamino)-2-phenylethanol (1.5 g), triethylamine (2.64 ml) and methylene chloride (30 ml) which was cooled in an ice-bath to 0° C. The mixture was stirred at 5° C. for 2 hours. The mixture was evaporated and the residue was partitioned between ethyl acetate and dilute aqueous sodium bicarbonate solution. The organic phase was washed with water and with brine, dried (MgSO$_4$) and evaporated.

The mesylate so obtained was added to a solution of sodium methanethiolate (0.66 g) in DMF (10 ml) and the mixture was stirred at laboratory temperature for 18 hours. The mixture was evaporated and the residue was purified by chromatography on silica gel using increasingly polar mixtures of hexane and ethyl acetate as eluent. There was thus obtained N-(tert-butoxycarbonyl)-2-methylthio-1-phenylethylamine (1.72 g) as a solid.

A solution of 3-chloroperbenzoic acid (1.92 g of material of 80% purity) in methylene chloride (15 ml) was added dropwise to a stirred solution of the product so obtained in methylene chloride (40 ml) which had been cooled to 0° C. The mixture was stirred at 0° C. for 1 hour and then allowed to warm to laboratory temperature. The mixture was stirred at laboratory temperature for 18 hours. The mixture was washed in turn with a 5% w/v aqueous solution of sodium metabisulphite, with a saturated aqueous sodium bicarbonate solution and with brine, dried (MgSO$_4$) and evaporated. The residue was purified by chromatography on silica gel using increasingly polar mixtures of hexane and ethyl acetate as eluent. There was thus obtained N-(tert-butoxycarbonyl)-2-mesyl-1-phenylethylamine (1.27 g) as a solid.

A mixture of the material so obtained, trifluoroacetic acid (2 ml) and methylene chloride (20 ml) was stirred at laboratory temperature for 2 hours. The mixture was evaporated and the residue was triturated under diethyl ether. There was thus obtained the required amine starting material as its trifluoroacetic acid salt (0.71 g).

b. DMF was used in place of ethyl acetate as the reaction solvent. The product, which was purified by chromatography on silica gel using increasingly polar mixtures of methylene chloride, isopropanol and trifluoroacetic acid as eluent, contained 0.2 equivalents of trifluoroacetic acid and 0.8 equivalents of isopropanol.

The 1-(3-nitrophenyl)-2-(1,2,4-triazol-3-ylthio)ethylamine, used as a starting material, was obtained as follows:

Using the procedure described in Note a. immediately above, (R/S)-2-(tert-butoxycarbonylamino)-2-(3-nitrophenyl)ethanol was reacted with mesyl chloride.

A mixture of the mesylate so obtained (1.14 g), 1,2,4-triazole-3-thiol, triethylamine (0.48 g) and DMF (10 ml) was heated to 60° C. for 18 hours. The mixture was evaporated and the residue was purified by chromatography on silica gel using a 7:3 v/v mixture of methylene chloride and ethyl acetate as eluent. There was thus obtained N-(tert-butoxycarbonyl)-1-(3-nitrophenyl)-2-(1,2,4-triazol-3-ylthio)ethylamine (0.5 g).

A mixture of a portion (0.4 g) of the product so obtained and trifluoroacetic acid was stirred at laboratory temperature for 2 hours and evaporated. There was thus obtained the required starting material as its trifluoroacetic acid salt.

c. The 2-dimethylamino-1-(3-nitrophenyl)ethylamine, used as a starting material, was obtained as follows:

Dimethylamine gas was led into a solution of (R/S)-N-(tert-butoxycarbonyl)-(3-nitrophenyl)glycine methyl ester (3 g) in DMF (20 ml) for 10 minutes and the mixture was stirred at laboratory temperature for 10 days. The mixture was evaporated and the residue was purified by chromatography on silica gel using increasingly polar mixtures of petroleum ether (b.p 40°–60° C.) and ethyl acetate as eluent. There was thus obtained N-(tert-butoxycarbonyl)-(3-nitrophenyl)glycine dimethylamide (1.31 g).

Diborane (1M in THF, 1ml) was added dropwise to a solution of the dimethylamide so obtained (0.323 g) in THF (2 ml) which had been cooled to 0°. The mixture was stirred at 0° C. for 1 hour. A further portion of diborane (2 ml of 1M solution) was added and the mixture was heated to reflux for 1 hour. The mixture was allowed to cool to laboratory temperature. The excess of reductant was destroyed by the dropwise addition of 6N aqueous hydrochloric acid (2 ml) and the mixture was heated to reflux for 5 minutes. The mixture was evaporated and the residue was partitioned between ethyl acetate and water. The aqueous extract was basified by the addition of 4N aqueous sodium hydroxide solution and extracted with ethyl acetate. Both organic extracts were combined, washed with water, dried (MgSO$_4$) and evaporated. The residue was purified by chromatography on reverse-phase silica gel using a 80:20:0.2 v/v mixture of water, methanol and trifluoroacetic acid as eluent. There was thus obtained the required starting material (0.211 g) as a gum.

NMR Spectrum (CD$_3$SOCD$_3$) 2.72 (s, 6H), 3.46 (broad s, 2H), 4.95 (t, 1H), 7.8–8.5 (m, 3H).

d. The (R/S) α-(4-methylthiazol-2-yl)benzylamine, used as a starting material, was obtained as follows:

Triethylamine (3.10 ml) and isobutyl chloroformate (2.42 ml) were added in turn to a solution (−)-N-(benzyloxycarbonyl)phenylglycine (5 g) in THF (60 ml) which had been cooled to −15° C. The mixture was stirred at −10° C. for 30 minutes. Gaseous ammonia was led into the mixture for 1 hour during which time the mixture was cooled to −5° C. The mixture was allowed to warm to laboratory temperature and evaporated. The residue was washed with water and dried in vacuo. There was thus obtained N-(benzyloxycarbonyl)phenylglycine amide (4.42 g).

A solution of phosphoryl chloride (1.85 ml) in methylene chloride (20 ml) was added dropwise to a solution of the amide so obtained (3.7 g) in pyridine (50 ml) which had been cooled to −5° C. The mixture was stirred at 0° C. for 1 hour and then partitioned between ethyl acetate and cold water. The organic phase was washed with water and with brine, dried (MgSO$_4$) and evaporated. The residue was purified by chromatography on silica gel using 4:1 v/v mixture of hexane and ethyl acetate as eluent. There was thus obtained N-(benzyloxycarbonyl)-α-cyanobenzylamine (3 g).

During a period of 2 hours hydrogen sulphide was led into a mixture of the benzylamine so obtained (0.5 g), diethylamine (0.78 ml) and DMF (8 ml) which was been heated to 55° C. The mixture was cooled to laboratory temperature and a mixture of ice and water (10 ml) was added. The mixture was stored at 0° C. for 16 hours. The resultant precipitate was isolated and dissolved in chloroform. The solution was dried (MgSO$_4$) and evaporated to give N-(benzyloxycarbonyl)phenylglycine thioamide (0.4 g).

A mixture of the thioamide (0.5 g), chloroacetone (0.28 ml), 2N aqueous hydrochloric acid (2 drops) and propanol (8 ml) was heated to reflux for 2 hours. The mixture was evaporated and the residue was partitioned between ethyl acetate and water. The organic phase was dried (MgSO$_4$) and evaporated. The residue was purified by chromatography on silica gel using a 3:1 v/v mixture of hexane and ethyl acetate as eluent. There was thus obtained (R/S)-N-(benzyloxycarbonyl)-α-(4-methylthiazol-2-yl)benzylamine (0.342 g) as a solid.

A mixture of a portion (0.33 g) of the product so obtained and a 45% w/v solution of hydrogen bromide gas in acetic acid (4.2 ml) was stirred at laboratory temperature for 1 hour. The mixture was stored at 0° C. for 16 hours. The mixture was evaporated and the residue was triturated under diethyl ether. There was thus obtained (R/S)-α-(4-methylthiazol-2-yl)benzylamine dihydrobromide (0.341 g).

NMR Spectrum (CD$_3$SOCD$_3$) 2.43 (s, 3H), 6.04 (q, 1H), 7.40 (s, 1H), 7.47 (m, 3H), 7.60 (m, 2H), 9,14 (broad, 3H).

e. The 2-tert-butoxy-1-(4-methylthiazol-2-yl)ethylamine, used as a starting material was obtained as follows:

Triethylamine (2.84 ml) and isobutyl chloroformate (2.21 ml) were added in turn to a solution of O-tert-butyl-N-(benzyloxycarbonyl)-L-serine (5 g) in THF (60 ml) which had been cooled to −15° C. The mixture was stirred at −10° C. for 30 minutes. Gaseous ammonia was led into the mixture for 1 hour during which time the mixture was cooled to −5° C. The mixture was allowed to warm to laboratory temperature and stirred for 1 hour. The mixture was evaporated and the residue was washed with water and dried in vacuo. There was thus obtained O-tert-butyl-N-(benzyloxycarbonyl)-L-serine amide (4.91 g).

A mixture of a portion (2 g) of the product so obtained, Lawesson's reagent (1.65 g) and acetonitrile (47 ml) was stirred at ambient temperature for 16 hours. The mixture was evaporated and the residue was purified by chromatography on silica gel using increasingly polar mixtures of toluene and ethyl acetate as eluent. There was thus obtained O-tert-butyl-N-(benzyloxycarbonyl)-L-serine thioamide (1.45 g).

A mixture of the thioamide so obtained, chloroacetone (0.783 ml), 2.6-lutidine (1.63 ml) and propanol (22 ml) was heated to reflux for 90 minutes. The mixture was evaporated and the residue was partitioned between ethyl acetate and water. The organic phase was washed with water, dried (MgSO$_4$) and evaporated. The residue was purified by chromatography on silica gel using increasingly polar mixtures of hexane and ethyl acetate as eluent. There was thus obtained (R/S)-N-(tert-butoxycarbonyl)-2-tert-butoxy-1-(4-methylthiazol-2-yl)ethylamine as a gum (1.14 g).

NMR Spectrum (CD$_3$SOCD$_3$) 1.13 (s, 9H), 2.34 (d, 3H), 3.60 and 3.72 (m, 2H), 4.90 (m, 1H), 5.08 (s, 2H), 7.1–7.4 (m, 6H).

Trimethylsilyl iodide (0.455 g) was added dropwise to a stirred solution of a portion (0.69 g) of the ethylamine so obtained in methylene chloride (20 ml) which was cooled in an ice-bath. The mixture was stirred at 0° C. for 10 minutes and at laboratory temperature for 16 hours. Methanol (0.128 ml) was added and the mixture was evaporated. There was thus obtained the required starting material as an oil (0.41 g) which was used without further purification.

f. This product was obtained when the intermediate formed in the preparation of Example 20, compound no. 5, after the coupling step and prior to the treatment with ammonia gas in methanol, was treated initially with trifluoroacetic acid and then with ammonia gas in methanol.

Thus a mixture of N-[2-tert-butoxy-1-(4-methylthiazol-2-yl)ethyl]-p-[N-(2-methyl-4-oxo-3-(pivaloyloxymethyl)-3,4-dihydroquinazolin-6-ylmethyl)-N-(prop-2-ynyl)amino]benzamide (0.719 g) and trifluoroacetic acid (10 ml) was stirred at laboratory temperature for 2 hours. The mixture was evaporated and the residue was purified by chromatography on silica gel using increasingly polar mixtures of methylene chloride and ethanol as eluent. There was thus obtained N-[2-hydroxy-1-(4-methylthiazol-2-yl)ethyl]-p-[N-(2-methyl-4-oxo-3-(pivaloyloxymethyl)-3,4-dihydroquinazolin-6-ylmethyl)-N-(prop-2-ynyl)amino]benzamide as an oil (0.686 g).

A portion (0.159 g) of the material so obtained was treated with ammonia in methanol using the procedure described in the second paragraph of Example 19 to remove the pivaloyloxymethyl group.

g. The 3-amino-3-(3-nitrophenyl)propanol, used as a starting material, was obtained as follows:

Thionyl chloride (1.11 ml) and 3-amino-3-(3-nitrophenyl)propionic acid (0.7 g) were added in turn to stirred methanol (5 ml) which had been cooled −20° C. The mixture was stirred at −20° C. for 10 minutes and at laboratory temperature for 16 hours. The mixture was evaporated to give methyl 3-amino-3-(3-nitrophenyl)propionate (0.83 g), as a solid.

Triethylamine (2 ml) and di-tert-butyl dicarbonate (1.044 g) were added in turn to a solution of the ester so obtained in DMF (5 ml). The mixture was stirred at laboratory temperature for 5 days. The mixture was evaporated and the residue was purified by chromatography on silica gel using a 3:2 v/v mixture of petroleum ether (b.p 40°–60° C.) and ethyl acetate as eluent. There was thus obtained methyl 3-(tert-butoxycarbonylamino)-3-(3-nitrophenyl)propionate (0.855 g).

The ester was added to a stirred suspension of sodium borohydride (0.618 g) and lithium chloride (0.693 g) in THF (20 ml) which was cooled to 10° C. The mixture was stirred at 10° C. for 5 minutes and at laboratory temperature for 4 days. The mixture was evaporated and the residue was purified by chromatography on silica gel using a 1:1 v/v mixture of petroleum ether and ethyl acetate as eluent. There was thus obtained 3-(tert-butoxycarbonylamino)-3-(3-nitrophenyl)propanol (0.195 g) as an oil.

NMR Spectrum (CDCl$_3$) 1.4 (s, 9H), 1.8 (m, 2H), 3.77 (m, 2H), 5.4 (m, 1H), 7.42–7.92 (m, 4H).

A mixture of the propanol so obtained and trifluoroacetic acid (2 ml) was stirred at laboratory temperature for 2 hours and evaporated. There was thus obtained the required starting material which was used without further purification.

EXAMPLE 21

The process described in Example 19 was repeated except that the appropriate amine was used in place of 2-amino-2-(4-fluorophenyl)ethanol. Unless otherwise stated the starting materials were racemic mixtures. There were thus obtained the compounds described in the following table, the structures of which were confirmed by proton magnetic resonance and mass spectrometry and by elemental analysis.

TABLE IX

| Ex 21 Compd. No. | Y$^2$ | x | m.p. (0° C.) |
|---|---|---|---|

| | TABLE IX-continued | | |
|---|---|---|---|
| 1[a] | 4-methylthiazol-2-yl | — | foam |
| 2[b] | 1,2,4-triazol-3-yl | 2.5 | 131–143 |
| 3[c] | 5-oxo-1,2,4-triazol-3-yl | 1 | 150–165 |

NOTES a. DMSO was used in place of ethyl acetate as the reaction solvent. The 3-pivaloyloxymethyl protecting group was removed by stirring a mixture of the protected product (0.22 g), 4N aqueous sodium hydroxide solution (5 ml) and 1,4-dioxane (5 ml) at laboratory temperature for 3 hours. The mixture was evaporated and the product was purified by chromatography on reverse-phase silica gel using a 50:50:0.2 v/v mixture of water, methanol and trifluoroacetic acid as eluent. There was thus obtained the product (containing 2.6 equivalents of trifluoroacetic acid, 0.062 g), as a foam.

The 2-(3-hydroxyisoxazol-5-ylmethylthio)-1-(4-methylthiazol-2-yl)ethylamine, used as a starting material, was obtained as follows:

2-(Benzyloxycarbonylamino)-2-(4-methylthiazol-2-yl)ethanethiol (0.616 g) was added to a solution of sodium ethoxide [prepared by the addition of sodium (0.05 g) to ethanol (8 ml)] and the mixture was stirred at laboratory temperature for 30 minutes. 5-Bromomethyl-3-(tert-butyldimethylsilyloxy)isoxazole (0.6 g) was added and the mixture was stirred at laboratory temperature for 1 hour. The mixture was evaporated to leave a gum (0.814 g).

A mixture of the product so obtained and a 45% w/v solution of hydrogen bromide gas in acetic acid (10 ml) was stirred at laboratory temperature of 90 minutes. The reaction mixture was added dropwise to diethyl ether and the resultant precipitate was isolated. There was thus obtained the required starting material as its hydrobromide salt (0.94 g).

The 2-(benzyloxycarbonylamino)-2-(4-methylthiazol-2-yl)ethanethiol, used above, was obtained as follows:

Triethylamine (206 g) and 4-methoxybenzyl chloride (89 g) were added in turn to a solution of cysteine hydrochloride (107 g) in a 2:1 v/v mixture of ethanol and water (1000 ml). The mixture was stirred at laboratory temperature for 16 hours. The mixture was filtered to give S-(4-methoxybenzyl)cysteine (107.4 g). The filtrate was stored −10° C. for 48 hours and a second crop (22.3 g) of the cysteine derivative was obtained.

Benzyl chloroformate (81.6 g) was added to a stirred mixture of the cysteine derivative so obtained (126 g), 1N aqueous sodium hydroxide solution (523 ml) and water (1000 ml) which was cooled in an ice-bath. The mixture was stirred at 15° C. for 2 hours. The mixture was concentrated by evaporation, acidified to pH4 by the addition of 2N aqueous hydrochloric acid and partitioned between ethyl acetate and water. The organic phase was washed with water, dried (MgSO₄) and evaporated. There was thus obtained N-(benzyloxycarbonyl)-S-(4-methoxybenzyl)cysteine (180 g).

Triethylamine (63 g) and ethyl chloroformate (67 g) were added in turn to a mixture of the cysteine derivative so obtained, 4 angstrom molecular sieves (50 g) and methylene chloride (1000 ml) which had been cooled to −5° C. The mixture was stirred at 0° C. for 1 hour. Gaseous ammonia was led into the mixture for 20 minutes and the mixture was stored at 0° C. for 16 hours. The mixture was filtered and the filtrate was washed with 1N aqueous sodium hydroxide solution, with water and with brine, dried (MgSO₄) and evaporated. There was thus obtained N-(benzyloxycarbonyl)-S-(4-methoxybenzyl)cysteine amide (105 g).

Lawessons reagent (2,4-bis(4-methoxyphenyl)-1,3-dithia-2,4-diphosphetane-2,4-disulphide, 30.3 g) was added to a solution of a portion (18.7 g) of the amide so obtained in acetonitrile (200 ml) and the mixture was stirred at laboratory temperature for 4 hours. The mixture was evaporated and the residue was purified by chromatography using a 2:1 v/v mixture of toluene and ethylacetate as eluent to give the thioamide (19 g).

2,6-Lutidine (4.82 g) and chloroacetone (3.70 g) were added in turn to a solution of a portion (8 g) of the thioamide in ethanol (140 ml) and the mixture was heated to reflux for 7 hours. The mixture was evaporated and the residue was purified by chromatography on silica gel using a 9:1 v/v mixture of methylene chloride and ethyl acetate as eluent. There was thus obtained N-(benzyloxycarbonyl)-2-(4-methoxybenzylthio)-1-(4-methylthiazol-2-yl)ethylamine (7 g).

Anisole (2.5 ml) and mercuric acetate (4 g) were added in turn to a solution of a portion (5.25 g) of the ethylamine so obtained in trifluoroacetic acid (100 ml) which had been cooled to 0° C. The mixture was stirred at 0° C. for 40 minutes and evaporated. 2-Mercaptoethanol (15 ml) was added to a solution of the residue so obtained in methanol (200 ml) which had been cooled to 0° C. The mixture was stirred at 4° C. for 16 hours. The mixture was filtered and the filtrate was evaporated. The residue was purified by chromatography on silica gel using increasingly polar mixtures of methylene chloride and ethyl acetate as eluent. There was thus obtained 2-(benzyloxycarbonylamino)-2-(4-methylthiazol-2-yl)ethanethiol (3 g).

The 5-bromomethyl-3-(tert-butyldimethylsilyloxy)isoxazole, used as a starting material, was obtained as follows:

Triethylamine (11.1 g) and tert-butyldimethylsilyl chloride (15.8 g) were added in turn to a mixture of 3-hydroxy-5-methylisoxazole (9.9 g; Chem. Pharm. Bull. 1966, 14, 1277), 3 angstrom molecular sieves (5 g) and methylene chloride (200 ml) which had been cooled to 3° C. The mixture was stirred at 3° C. for 3 hours. The mixture was concentrated and purified by chromatography on silica gel using a 1:1 v/v mixture of petroleum ether (b.p. 40°–60° C.) and methylene chloride as eluent. There was thus obtained 3-(tert-butyldimethylsilyloxy)-5-methylisoxazole (16.2 g), as an oil.

A mixture of a portion (14.3 g) of the product so obtained, 1,3-dibromo-5,5-dimethylhydantoin (10.1 g), azobisisobutyronitrile (0.1 g) and carbon tetrachloride (450 ml) was heated to reflux for 16 hours. The mixture was filtered and the filtrate was purified by chromatography on silica gel using initially methylene chloride and then a 9:1:0.1 v/v mixture of methylene chloride, methanol and acetic acid as eluent. There was thus obtained 5-bromomethyl-3-(tert-butyldimethylsilyloxy)isoxazole (3.97 g).

b. DMSO was used in place of ethyl acetate as the reaction solvent.

The 2-(3-hydroxyisoxazol-5-ylmethylthio)-1-(1,2,4-triazol-3-yl)ethylamine, used as a starting material, was obtained using an analogous procedure to that described in Note a. above except that 2-(benzyloxycarbonylamino)-2-(1,2,4-triazol-3-yl)ethanethiol was reacted with 5-bromomethyl-3-(tert-butyldimethylsilyloxy)isoxazole.

The 2-(benzyloxycarbonylamino)-2-(1,2,4-triazol-3-yl)ethanethiol starting material was obtained as follows:

Phosphoryl chloride (46 g) was added dropwise to a solution of N-(benzyloxycarbonyl)-S-(4-methoxybenzyl)cysteine amide (75 g) in pyridine (900 ml) which had been cooled to −10° C. The mixture was stirred at 0° C. for 2 hours and at laboratory temperature for 4 hours. The bulk of the pyridine was evaporated and the residue was partitioned between ethyl acetate and ice-cold water. The organic phase was washed with 2N aqueous hydrochloric acid and with water, dried (MgSO4) and evaporated to leave an oil (49.8 g).

Hydrogen chloride gas was led during 15 minutes into a mixture of a portion (20 g) of the product so obtained, ethanol (2.6 g), methylene chloride (20 ml) and diethyl ether (50 ml) which had been cooled to 0° C. The mixture was stirred at 5° C. for 30 minutes and at laboratory temperature for 2 hours. The mixture was evaporated and the residue was partitioned between a 1:1 v/v mixture of methylene chloride and diethyl ether and a cold saturated aqueous potassium carbonate solution. The organic phase was dried (MgSO4) and evaporated to give ethyl 2-(benzyloxycarbonylamino)-3-(4-methoxybenzylthio)propionimidate as a solid (22 g).

Triethylamine (6.06 g) and formylhydrazine (2.4 g) were added in turn to a solution of a portion (8.04 g) of the imino ether so obtained in ethanol (40 ml). The mixture was stirred at laboratory temperature for 4 hours and then stored at 4° C. for 16 hours. The mixture was evaporated and the residue was purified by chromatography on silica gel using increasingly polar mixtures of methylene chloride and methanol as eluent. There was thus obtained a yellow oil (5.3 g).

The product so obtained was dissolved in toluene (40 ml) and the mixture was heated to reflux for 2.5 hours. The solution was stored at 4° C. for 16 hours and the resultant precipitate was isolated. There was thus obtained N-(benzyloxycarbonyl)-2-(4-methoxybenzylthio)-1-(1,2,4-triazol-3-yl)ethylamine (3.81 g).

Anisole (1 ml) and mercuric acetate (1.91 g) were added in turn to a solution of a portion (2.38 g) of the ethylamine so obtained in trifluoroacetic acid (50 ml) which had been cooled to 0° C. The mixture was stirred at 0° C. for 30 minutes and evaporated. 2-Mercaptoethanol (5 ml) was added to a solution of the residue so obtained in methanol (50 ml) which had been cooled to 0° C. The mixture was stirred at 4° C. for 1 hour and at laboratory temperature for 2 hours. The mixture was filtered and the filtrate was evaporated. The residue was purified by chromatography on silica gel using increasingly polar mixtures of methylene chloride and methanol as eluent. There was thus obtained 2-(benzyloxycarbonylamino)-2-(1,2,4-triazol-3-yl)ethanethiol (1.5 g).

c. The product was purified by chromatography on reverse-phase silica gel using decreasingly polar mixtures of methanol, water and trifluoroacetic acid as eluent. The product contained 1 equivalent of water and 1.8 equivalents of trifluoroacetic acid.

The 2-(3-hydroxyisoxazol-5-ylmethylthio)-1-(5-oxo-1,2,4-triazol-3-yl)ethylamine, used as a starting material, was obtained using an analogous procedure to that described in Note a. above except that 2-(benzyloxycarbonylamino)-2-(5-oxo-1,2,4-triazol-3-yl)ethanethiol was reacted with 5-bromomethyl-3-(tert-butyldimethylsilyloxy)isoxazole.

The 2-(benzyloxycarbonylamino)-2-(5-oxo-1,2,4-triazol-3-yl)ethanethiol starting material was obtained as follows:

Triethylamine (3.04 g) and ethyl carbazate (2.08 g) were added in turn to a stirred solution of ethyl 2-(benzyloxycarbonylamino)-3-(4-methoxybenzylthio)propionimidate (4.02 g) in ethanol (20 ml) and the mixture was stirred at laboratory temperature for 6 hours and then stored at 4° C. for 70 hours. The mixture was evaporated and the residue was purified by chromatography on silica gel using increasingly polar mixtures of methylene chloride and methanol as eluent. There was thus obtained a yellow foam (3.9 g).

A portion (1 g) of the product so obtained was heated to 150° C. for 2.5 hours. The material so obtained was purified by chromatography on silica gel using increasingly polar mixtures of petroleum ether (b.p. 40°–60° C.) and ethyl acetate as eluent. There was thus obtained N-(benzyloxycarbonyl)-2-(4-methoxybenzylthio)-1-(5-oxo-1,2,4-triazol-3-yl)ethylamine (0.54 g) as a yellow foam.

Anisole (0.16 ml) and mercuric acetate (0.32 g) were added in turn to a solution of a portion (0.413 g) of the ethylamine so obtained in trifluoroacetic acid (10 ml) which had been cooled to 0° C. The mixture was stirred at 0° C. for 1 hour and evaporated. 2-Mercaptoethanol (1 ml) was added to a mixture of the residue so obtained and methanol (10 ml) and the mixture was stirred at laboratory temperature for 1 hour. The mixture was filtered and the filtrate was evaporated. The residue was purified by chromatography on silica gel using increasingly polar mixtures of methylene chloride and methanol as eluent. There was thus obtained 2-(benzyloxycarbonylamino)-2-(5-oxo-1,2,4-triazol-3-yl)ethanethiol (0.3 g).

EXAMPLE 22

Using an analogous procedure to that described in Example 19, pentafluorophenyl p-[N-(2,7-dimethyl-4-oxo-3-(pivaloyloxymethyl)-3,4-dihydroquinazolin-6-ylmethyl-N-methylamino]benzoate was reacted with 2-amino-2-(3-nitrophenyl)ethanol and the pivaloyloxymethyl protecting group was removed from the resultant product to give p-[N-(2,7-dimethyl-4-oxo-3,4-dihydroquinazolin-6-ylmethyl)-N-methylamino]-N-[2hydroxy-1-(3-nitrophenyl)ethyl]benzamide (containing 1.25 equivalents of water and 0.25 equivalents of pivalic acid) in 73% yield, m.p. 231°–240° C.

The pentafluorophenyl p-[N-(2,7-dimethyl-4-oxo-3-(pivaloyloxymethyl)-3,4-dihydroquinazolin-6-ylmethyl)-N-methylamino]benzoate, used as a starting material, was obtained as follows:

A mixture of 6-bromomethyl-2,7-dimethyl-3-(pivaloyloxymethyl)-3,4-dihydroquinazolin-4-one (12 g), p-methylaminobenzoic acid (5.4 g), 2,6-lutidine (5 g), sodium iodide (5 mg) and DMF (175 ml) was stirred and heated to 60° C. for 20 hours. The mixture was cooled and partitioned between diethyl ether and water. The organic phase was washed with water and with brine, dried (MgSO4) and evaporated. There was thus obtained a light brown solid (16.6 g) which was used without further purification.

Pentafluorophenol (19.6 g) and dicyclohexylcarbodiimide (16.5 g) were added in turn to a solution of the product so obtained (16 g) in DMF (380 ml) which had been cooled in an ice-bath. The mixture was stirred at laboratory temperature for 40 hours. The mixture was evaporated and the residue was purified by chromatography on silica gel using a 98.5:1.5 v/v mixture of chloroform and methanol as eluent. There was thus obtained a light brown solid which was triturated under diethyl ether to give the required starting material (13.55 g).

EXAMPLE 23

Using an analogous procedure to that described in Example 19, pentafluorophenyl p-[N-(7-bromo-2-methyl-4-oxo-3-(pivaloyloxymethyl)-3,4-dihydroquinazolin-6-ylmethyl)-N-(prop-2-ynyl)amino]benzoate was reacted with 2-amino-2-(3-nitrophenyl)ethanol and the pivaloyloxymethyl protecting group was removed from the resultant product to give p-[N-(7-bromo-2-methyl-4-oxo-3,4-dihydroquinazolin-6-ylmethyl)-N-(prop-2-ynyl)amino]-N-[2-hydroxy-1-(3-nitrophenyl)ethyl]benzamide (containing 0.25 equivalents of water) in 61% yield, m.p. 221°-232° C.

The pentafluorophenyl p-[N-(7-bromo-2-methyl-4-oxo-3-(pivaloyloxymethyl)-3,4-dihydroquinazolin-6-ylmethyl)-N-(prop-2-ynyl)amino]benzoate, used as a starting material, was obtained as follows:

A mixture of 7-bromo-6-bromomethyl-2-methyl-3-(pivaloyloxy)methyl)-3,4-dihydroquinazolin-4-one (5.8 g), tert-butyl p-(prop-2-ynyl)aminobenzoate (3.6 g), calcium carbonate (1.3 g) and DMA (200 ml) was stirred and heated to 100° C. for 36 hours. The mixture was evaporated and the residue was partitioned between ethyl acetate and water. The organic phase was washed with water, dried (MgSO₄) and evaporated. The residue was purified by chromatography on silica gel using increasingly polar mixtures of hexane and ethyl acetate as eluent to give a solid (3.5 g).

A mixture of the product so obtained (3.3 g), trifluoroacetic acid (50 ml) and methylene chloride (200 ml) was stirred at laboratory temperature for 1 hour. The mixture was evaporated and the residue was triturated under diethyl ether. Evaporation of the solvent left p-[N-(7-bromo-2-methyl-4-oxo-3-(pivaloyloxymethyl)-3,4-dihydroquinazolin-6-ylmethyl)-N-(prop-2-ynyl)amino]benzoic acid (3.3 g) as a foam.

Pentafluorophenol (2.8 g) and dicyclohexylcarbodiimide (3.2 g) were added in turn to a solution of the benzoic acid so obtained in methylene chloride (300 ml) and the mixture was stirred at laboratory temperature for 3 hours. The mixture was evaporated and the residue was purified by chromatography on silica gel using a 5:1 v/v mixture of toluene and ethyl acetate as eluent. There was thus obtained the required starting material (2.53 g) as a white solid.

The 7-bromo-6-bromomethyl-2-methyl-3-(pivaloyloxymethyl)-3,4-dihydroquinazolin-4-one, used above, was prepared as follows:

Bromine (37 g) was added dropwise to a rigorously stirred mixture of 3-bromo-4-methylaniline (43 g), acetic acid (400 ml) and diethyl ether (400 ml) which had been cooled in an ice-bath. The addition took approximately 30 minutes. The resultant precipitate was isolated and washed with diethyl ether. The solid was partitioned between diethyl ether and a saturated aqueous sodium bicarbonate solution. The organic phase was washed with water, dried (MgSO₄) and evaporated. The residue was purified by chromatography on silica gel using toluene as eluent. There was thus obtained 2,5-dibromo-4-methylaniline (20 g).

Acetic anhydride (8.5 g) and pyridine (6.55 g) were added in turn to a solution of the aniline so obtained in ethyl acetate (200 ml) and the mixture was stirred at laboratory temperature for 3 days. The mixture was evaporated and diethyl ether (200 ml) was added to the residue. The resultant precipitate was isolated and washed with diethyl ether. There was thus obtained 2,5-dibromo-4-methylacetanilide (16 g).

A mixture of a portion (14.5 g) of the acetanilide so obtained, cuprous cyanide (6.35 g) and N-methylpyrrolidin-2-one (200 ml) was stirred and heated to 150° C. for 40 minutes. The mixture was allowed to cool and poured into a mixture of dilute ammonium hydroxide (200 ml) and water (600 ml). The resultant precipitate was isolated and washed with water, dissolved in methylene chloride (1 liter) and dried (MgSO₄). The solvent was evaporated and the residue was triturated under ethyl acetate. There was thus obtained 5-bromo-2-cyano-4-methylacetanilide (9.8 g).

Hydrogen peroxide (150 ml of a 30% w/v aqueous solution) and an aqueous sodium hydroxide solution (4 g in 40 ml) were added in turn to a solution of the acetanilide so obtained in ethanol (200 ml) and the mixture was heated carefully to 55° C. An exothermic reaction was observed and external heating was removed briefly. The mixture was heated to 55° C. for 4 hours. The mixture was cooled to laboratory temperature and dilute aqueous hydrochloric acid was added. The bulk of the ethanol was evaporated. The precipitate was isolated and dried. There was thus obtained 7-bromo-2,6-dimethyl-3,4-dihydroquinazolin-4-one (7.9 g).

A solution of the quinazolin-4-one so obtained in DMSO (60 ml) was added to a stirred suspension of sodium hydride (60% w/w dispersion in mineral oil, 1.9 g) in DMSO (20 ml) and the mixture was stirred at laboratory temperature for 1 hour. A solution of chloromethyl pivalate (9.4 g) in DMSO (20 ml) was added and the mixture was stirred at laboratory temperature for 16 hours. The mixture was poured onto a mixture of dilute aqueous hydrochloric acid and ice, and extracted with ethyl acetate. The organic phase was dried (MgSO₄) and evaporated. The residue was triturated under a mixture of hexane and diethyl ether. There was thus obtained 7-bromo-2,6-dimethyl-3-(pivaloyloxymethyl)-3,4-dihydroquinazolin-4-one (6.3 g).

A mixture of the product so obtained, N-bromosuccinimide (3.2 g), benzoyl peroxide (0.1 g) and chloroform (300 ml) was heated to reflux for 6 hours. The mixture was evaporated and the residue was purified by chromatography on silica gel using a 9:1 v/v mixture of toluene and ethyl acetate as eluent.

There was thus obtained 7-bromo-6-bromomethyl-2-methyl-3-(pivaloyloxymethyl)-3,4-dihydroquinazolin-4-one (6.5 g).

EXAMPLE 24

The procedure described in the first paragraph of Example 1 was repeated except that 2-(α-aminobenzyl)-2-methyl-1,3-dioxolane was used in place (−)-(2R)-2-amino-2-phenylethanol and that the reaction mixture was stirred at 20° C. for 70 hours.

A mixture of the product so obtained (0.9 g), 1N aqueous sodium hydroxide solution (7 ml) and ethanol (35 ml) was stirred at ambient temperature for 4.5 hours. The mixture was evaporated. Water (30 ml) was added to the residue and the mixture was acidified to pH6 by the addition of glacial acetic acid. The precipitate so obtained was washed with water and dried.

A mixture of the product (0.25 g) so obtained, 2N aqueous hydrochloric acid (2.5 ml) and acetone (35 ml)

was heated to 45° C. for 3 hours. The mixture was evaporated and the residue was triturated under water. The solid so obtained was washed with water and dried in vacuo. There was thus obtained p-[N-(2-methyl-4-oxo-3,4-dihydroquinazolin-6-ylmethyl)-N-(prop-2-ynyl-)amino]-N-(2-oxo-1-phenylpropyl)benzamide (containing 3.5 equivalents of water, 0.12 g), m.p. 164°–169° C.

NMR Spectrum: (CD$_3$SOCD$_3$): 2.10 (s, 3H, CH$_3$), 2.55 (s, 3H, CH$_3$), 3.21 (broad s,1H, C≡CH), 4.33 (broad s, 2H, CH$_2$Ar), 4.82 (s, 2H, CH$_2$N), 5.66 (d, 1H, CHPh), 6.84 and 7.78 (m, 4H, aromatic), 7.28–7.47 (m, 5H, aromatic), 7.70–7.89 (m, 2H, aromatic), 8.03 (d, 1H, aromatic), 8.68 (d, 1H, CONH);

Mass Spectrum: (Positive ion FAB) m/e (P+1) 479;
Elemental Analysis: Found, C, 64.5; H, 5.6; N, 10.5; C$_{29}$H$_{26}$N$_4$O$_3$ 3.5H$_2$O requires C, 64.3; H, 5.9; N, 10.4%.

The 2-(α-aminobenzyl)-2-methyl-1,3-dioxolane, used as a starting material, was obtained as follows:

A mixture of phenylglycine (15.1 g), acetic anhydride (100 ml) and pyridine (100 ml) was heated to 90° C. until the evolution of gas was observed to stop. The mixture was evaporated, toluene (300 ml) was added and the mixture was evaporated. A mixture of the residue and 5N aqueous hydrochloric acid (200 ml) was heated to reflux for 4 hours. The mixture was evaporated and the residue was recrystallised from ethanol. There was thus obtained 1-amino-1-phenylpropan-2-one hydrochloride (9.19 g), m.p. 204°–207° C.

A mixture of the product so obtained, ethylene glycol (3.4 ml), p-toluenesulphonic acid (12 g) and toluene (500 ml) was heated to reflux for 8 hours under a Dean and Stark water separator. The mixture was cooled and the precipitate was isolated. There was thus obtained the required starting material as its p-toluenesulphonic acid salt (12.7 g).

NMR Spectrum (CD$_3$SOCD$_3$) 1.09 (s, 3H), 2.29 (s, 3H), 4.02 (m, 4H), 4.48 (m, 1H), 7.12 (d, 2H), 7.4–7.6 (m, 7H), 8.33 (broad s, 3H).

EXAMPLE 25

The procedure described in Example 24 was repeated except that 2-(α-amino-4-chlorobenzyl)-2-methyl-1,3-dioxolane was used in place of 2-(α-aminobenzyl)-2-methyl-1,3-dioxolane. There was thus obtained N-[1-(4-chlorophenyl)-2-oxopropyl]-p-[N-(2-methyl-4-oxo-3,4-dihydroquinazolin-6-ylmethyl)-N-(prop-2-ynyl)amino]-benzamide (containing 4 equivalents of water), m.p. 184°–190° C.

The 2-(α-amino-4-chlorobenzyl)-2-methyl-1,3-dioxolane, used as a starting material, was obtained as follows:

The procedure described in the portion of Example 23 which is concerned with the preparation of starting materials was repeated except that α-amino-4-chlorophenylacetic acid was used in place of phenylglycine. There was thus obtained the required starting material as its p-toluenesulphonic acid salt in 47% yield.

NMR Spectrum (CD$_3$SOCD$_3$) 1.08 (s, 3H), 2.29 (s, 3H), 3.95–4.06 (m, 4H), 4.56 (m, 1H), 7.10 (d, 2H), 7.44–7.60 (m, 6H), 8.33 (broad s, 3H).

EXAMPLE 26

A mixture of pentafluorophenyl p-[N-(2-methyl-4-oxo-3-(pivaloyloxymethyl)-3,4-dihydroquinazolin-6-ylmethyl)-N-(prop-2-ynyl)amino]benzoate (1.08 g), (4S,5S)-(+)-5-amino-2,2-dimethyl-4-phenyl-1,3-dioxane (0.36 g), triethylamine (1.2 ml), N-hydroxybenzotriazole (0.065 g) and ethyl acetate (30 ml) was stirred at laboratory temperature for 72 hours. The mixture was evaporated and the residue was triturated under hexane. The white solid so obtained was washed with diethyl ether.

A mixture of the product so obtained, 2N aqueous hydrochloric acid (15 ml) and acetone (15 ml) was heated to 65° C. for 3 hours. The mixture was evaporated and the residue was partitioned between ethyl acetate and water. The organic layer was dried (MgSO$_4$) and evaporated. The residue was purified by chromatography on silica gel using increasingly polar mixtures of methylene chloride and ethanol as eluent to give a solid (0.54 g).

A saturated solution of ammonia gas in ethanol (20 ml) was added to a solution of the product so obtained in ethanol (3 ml) and the mixture was stirred at laboratory temperature for 48 hours. The mixture was evaporated and the residue was triturated under diethyl ether. There was thus obtained N-[(1S,2S)-1,3-dihydroxy-1-phenylprop-2-yl]-p-[N-(2-methyl-4-oxo-3,4-dihydroquinazolin-6-ylmethyl)-N-(prop-2-ynyl)amino]benzamide (containing 0.25 equivalents of water, 0.24 g), m.p. 210°–212° C.

NMR Spectrum: (CDCl$_3$+CD$_3$SOCD$_3$): 2.37 (t, 1H, C≡CH), 2.57 (s, 3H, CH$_3$), 3.70–3.92 (m, 2H, CH$_2$OH), 4.17 (d, 2H, CH$_2$C≡C), 4.35 (q, 1H, NHCH), 4.76 (s, 2H, CH$_2$N), 5.11 (d, 1H, CHOH), 6.8–7.65 (m, 4H, aromatic), 7.20–7.48 (m, 5H, aromatic), 7.70–7.85 (m, 2H, aromatic), 8.13 (d, 1H, aromatic);

Mass Spectrum: (Positive Ion FAB) m/e (P+1) 497;
Elemental Analysis: Found C, 69.4; H, 5.5; N, 11.4; C$_{29}$H$_{28}$N$_4$O$_4$ 0.25H$_2$O requires C, 69.5; H, 5.7; N, 11.2%.

EXAMPLE 27

Using similar procedures to those described in Example 10, p-[N-(2,7-dimethyl-4-oxo-3-(pivaloyloxymethyl)-3,4-dihydroquinazolin-6-ylmethyl)-N-(prop-2-ynyl)amino]benzoic acid and (R/S)-(3-nitrophenyl)glycine N-(methylsulphonyl)amide were reacted to give N-[p-[N-(2,7-dimethyl-4-oxo-3,4-dihydroquinazolin-6-ylmethyl)-N-(prop-2-ynyl)amino]benzoyl]-(3-nitrophenyl)glycine N-(methylsulphonyl)amide (containing 4.5 equivalents of water) in 22% yield, m.p. 237°–242° C. (after trituration of the product under diethyl ether).

EXAMPLE 28

A mixture of pentafluorophenyl p-[N-(4-oxo-2-pivaloylamino-3,4-dihydroquinazolin-6-ylmethyl)-N-(prop-2-ynyl)amino]benzoate (0.3 g), the trifluoroacetic acid salt of 2-amino-2-(3-nitrophenyl)ethanol (0.2 g), triethylamine (0.41 ml) and DMSO (10 ml) was stirred at laboratory temperature for 48 hours. The mixture was evaporated and the residue was purified by chromatography on silica gel using ethyl acetate as eluent to give a pale yellow oil (0.35 g).

A mixture of the product so obtained and 2N aqueous sodium hydroxide solution was stirred at ambient temperature for 16 hours. The mixture was evaporated and the residue was purified by chromatography on reverse-phase silica gel using decreasingly polar mixtures of methanol, water and trifluoroacetic acid as eluent. The solid so obtained was stirred in water (5 ml) and the acidity of the mixture was reduced to pH5 by the addition of 1N aqueous sodium hydroxide solution. The mixture was filtered and the solid was washed in turn with water, acetone and diethyl ether. There was thus obtained p-[N-(2-amino-4-oxo-3,4-dihydroquinazolin-6-ylmethyl)-N-(prop-2-ynyl)amino]-N-[2-hydroxy-1-(3- nitrophenyl)ethyl]benzamide (containing 0.8 equivalents of sodium chloride, 0.12 g), m.p. 236°–240° C.

NMR Spectrum (CD$_3$SOCD$_3$): 3.18 (s, 1H, C≡CH), 3.65–3.75 (m, 2H, CH$_2$OH), 4.30 (broad s, 2H, CH$_2$Ar), 4.71 (s, 2H, CH$_2$N), 5.08–5.18 (m, 1H, CHNH), 6.84 and 7.78 (m, 4H, aromatic), 7.25 (d, 1H, aromatic), 7.55–7.67 (m, 2H, aromatic), 7.78–7.90 (m, 2H, aromatic), 8.09 (d, 1H, aromatic), 8.26 (broad s, 1H, aromatic), 8.52 (d, 1H, CONH).

Mass Spectrum: (positive ion FAB) m/e (P+1) 513;
Elemental analysis: Found C, 58.2; H, 4.1; N, 14.6; C$_{28}$H$_{24}$N$_6$O$_5$0.8NaCl requires C, 58.0; H, 4.3; N, 15.0%.

The pentafluorophenyl p-[N-(4-oxo-2-pivaloylamino-3,4-dihydroquinazolin-6-ylmethyl)-N-(prop-2-ynyl)amino]benzoate, used as a starting material, was obtained as follows:

A mixture of 6-bromomethyl-4-oxo-2-pivaloylamino-3,4-dihydroquinazoline (14 g; *J. Het. Chem.*, 1975, 12, 1283) tert-butyl p-(prop-2-ynyl)aminobenzoate (12 g; European Patent Application No. 239362), 2,6-lutidine (4.87 g), sodium iodide (0.25 g) and DMF was heated to 95° C. for 10 hours. The solvent was evaporated and the residue was triturated in a 10:1 v/v mixture of ethyl acetate and methylene chloride. The solid so obtained was washed with ethyl acetate and diethyl ether. There was thus obtained tert-butyl p-[N-(4-oxo-2-pivaloylamino-3,4-dihydroquinazolin-6-ylmethyl)-N-(prop-2-ynyl)amino]benzoate (15.18 g).

A mixture of a portion (8.5 g) of the product so obtained, trifluoroacetic acid (15 ml) and methylene chloride (150 ml) was stirred at laboratory temperature for 4 hours. The mixture was evaporated and the residue was triturated in a 4:1 v/v mixture of diethyl ether and ethyl acetate. The solid so obtained was washed with diethyl ether. There was thus obtained p-[N-(4-oxo-2-pivaloylamino-3,4-dihydroquinazolin-6-ylmethyl)-N-(prop-2-ynyl)amino]benzoic acid (7.1 g).

NMR Spectrum (CD$_3$SOCD$_3$) 1.25 (s, 9H, CMe$_3$), 3.21 (t, 1H, C≡CH), 4.35 (broad s, 2H, CH$_2$C≡C), 4.79 (s, 2H, CH$_2$), 6.8–7.8 (m, 4H, aromatic), 7.49 (1H, m, aromatic), 7.70 (1H, m, aromatic), 7.95 (1H, d, aromatic).

A solution of dicyclohexylcarbodiimide (1.93 g) in DMSO (5 ml) was added to a mixture of a portion (3 g) of the benzoic acid so obtained, pentafluorophenol (2.23 g), triethylamine (2.11 g), ethyl acetate (48 ml) and DMSO (43 ml). The mixture was stirred at laboratory temperature for 2 days. The mixture was evaporated and the residue was purified by chromatography on silica gel using increasingly polar mixtures of hexane and ethyl acetate as eluent. There was thus obtained the required starting material as a white foam (1.22 g).

EXAMPLE 29

A solution of m-chloroperbenzoic acid (0.024 g of material of 60% purity) in DMF (0.5 ml) was added dropwise to a solution of p-[N-(2-methyl-4-oxo-3,4-dihydroquinazolin-6-ylmethyl)-N-(prop-2-ynyl)amino]-N-[1-(3-nitrophenyl)-2-(1,2,4-triazol-3-ylthio)ethyl]benzamide (0.05 g) in DMF (0.5 ml) and the mixture was stirred at laboratory temperature for 3 hours. The mixture was evaporated and the residue was purified by chromatography on silica gel using increasingly polar mixtures of methylene chloride, methanol and acetic acid as eluent. There was thus obtained p-[N-(2-methyl-4-oxo-3,4-dihydroquinazolin-6-ylmethyl)-N-(prop-2-ynyl)amino]-N-[1-(3-nitrophenyl)-2-(1,2,4-triazol-3-ylsulphinyl)ethyl]benzamide (containing 1 equivalent of water, 1.2 equivalents of acetic acid and 0.2 equivalents of diethyl ether, 0.046 g), m.p. 182°–198° C.

NMR Spectrum: (CD$_3$SOCD$_3$) 2.34 (s, 3H, CH$_3$), 3.08 (s, 1H, C≡CH), 3.70–4.00 (m, 2H, CH$_2$SO), 4.34 (s, 2H, NCH$_2$C≡C), 4.79 (s, 2H, ArCH$_2$N), 5.30–5.45 (m, 1H, CHNH), 7.89 (m, 2H, aromatic), 7.52–8.00 (m, 5H, aromatic), 8.01 (s, 1H, aromatic), 8.14 (m, 1H, aromatic), 8.29 (m, 1H, aromatic), 8.78 and 8.81 (2 s's, 1H, aromatic), 9.0 (m, 1H, CONHCH);

Mass Spectrum; (Positive ion FAB) m/e (P+1) 611;
Elemental Analysis Found; C, 55.2; H, 4.7; N, 15.2; C$_{30}$H$_{28}$N$_8$O$_5$S1H$_2$O1.2CH$_3$COOH0.2Et$_2$O requires: C, 55.5; H, 5.1; N, 15.6%.

EXAMPLE 30

A solution of m-chloroperbenzoic acid (0.097 g of material of 60% purity) in DMF (1 ml) was added dropwise to a solution of p-[N-(2-methyl-4-oxo-3,4-dihydroquinazolin-6-ylmethyl)-N-(prop-2-ynyl)amino]-N-[1-(3-nitrophenyl)-2-(1,2,4-triazol-3-ylthio)ethyl]benzamide (0.1 g) in DMF (2 ml) and the mixture was stirred at laboratory temperature for 3 hours. A second portion (0.04 g) of m-chloroperbenzoic acid was added and the mixture was stirred at laboratory temperature for a further 3 hours. The mixture was evaporated and the residue was purified by chromatography on reverse-phase silica gel using decreasingly polar mixtures of methanol, water and trifluoroacetic acid as eluent. The product so obtained was further purified by chromatography on silica gel using increasingly polar mixtures of methylene chloride, methanol and acetic acid as eluent. There was thus obtained p-[N-(2-methyl-4-oxo-3,4-dihydroquinazolin-6-ylmethyl)-N-(prop-2-ynyl)amino]-N-[1-(3-nitrophenyl)-2-(1,2,4-triazol-3-ylsulphonyl)ethyl]benzamide (containing 1.2 equivalents of acetic acid and 1.4 equivalents of trifluoroacetic acid, 0.056 g), m.p. 248°–251° C.

NMR Spectrum: (CD$_3$SOCD$_3$) 2.32 (s, 3H, CH$_3$), 3.17 (s, 1H, C≡CH), 3.78 (m, 1H, CH$_A$H$_B$SO$_2$), 4.06 (m, CH$_A$H$_B$SO$_2$), 4.31 (s, 2H, NCH$_2$), 4.77 (s, 2H, CH$_2$), 5.50–5.63 (m, 1H, NCH), 6.65 and 7.67 (m, 4H, aromatic), 7.50–7.85 (m, 3H, aromatic), 7.97 (s, 1H), 8.06 (d, 1H, aromatic), 8.21 (s, 1H, aromatic), 9.04 (d, 1H, CONH), 12.10 (broad s, 1H, NH);

Mass Spectrum; (Positive ion FAB): m/e (P+1) 627;
Elemental Analysis: Found C, 49.5; H, 3.8; N, 12.9; C$_{30}$H$_{26}$N$_8$O$_6$S 1.2CH$_3$CO$_2$H 1.4CF$_3$COOH requires C, 49.2; H, 3.8; N, 13.0%.

EXAMPLE 31

A mixture of pentafluorophenyl p-[N-(2,7-dimethyl-4-oxo-3-(pivaloyloxymethyl)-3,4-dihydroquinazolin-6-ylmethyl)-N-(prop-2-ynyl)amino]benzoate [1.28 g; prepared from the corresponding benzoic acid and pentafluorophenol using an analogous procedure to that described in the portion of Example 9 which is concerned with the preparation of starting materials], 1-(3-nitrophenyl)-2-(1,2,4-triazol-3-ylthio)ethylamine trifluoroacetic acid salt (0.73 g), triethylamine (2.02 g) and DMSO (15 ml) was stirred at laboratory temperature for 16 hours. The mixture was evaporated and the residue was purified by chromatography on silica gel using increasingly polar mixtures of ethyl acetate and isopropanol as eluent to give an oil (0.474 g).

A mixture of the material so obtained and a saturated solution of ammonia gas in methanol (15 ml) was stirred at ambient temperature for 24 hours. The mixture was evaporated and the residue was triturated under diethyl ether. There was thus obtained p-[N-(2,7-dimethyl-4-oxo-3,4-dihydroquinazolin-6-ylmethyl)-N-(prop-2-ynyl)amino]-N-[1-(3-nitrophenyl)-2-(1,2,4-triazol-3-ylthio)ethyl]benzamide (containing 1 equivalent of water, 0.382 g), m.p. 219°-236° C.

NMR Spectrum (CD$_3$SOCD$_3$) 2.30 and 2.43 (2 s's, 6H), 3.16 (s, 1H), 3.45-3.70 (m, 2H), 4.26 (s, 2H), 4.66 (s, 2H), 5.49 (m, 1H), 6.8-8.3 (m, 8H), 8.45 (broad s, 1H), 8.9 (s, 1H).

Mass Spectrum (Positive ion FAB): m/e (P+1) 609;

Elemental Analysis Found C, 59.9; H, 5.3; N, 18.1; C$_{31}$H$_{28}$N$_8$O$_4$S 1H$_2$O requires C, 59.4; H, 4.8; N, 17.9%.

EXAMPLE 32

Using a similar procedure to that described in Example 29, p-[N-(2,7-dimethyl-4-oxo-3,4-dihydroquinazolin-6-ylmethyl)-N-(prop-2-ynyl)amino]-N-[1-(3-nitrophenyl)-2-(1,2,4-triazol-3-ylthio)ethyl]benzamide (0.14 g) was reacted with m-chloroperbenzoic acid (0.066 g of material of 60% purity) to give a crude product which was purified by chromatography on reverse-phase silica gel using a 50:50:0.2 v/v mixture of methanol, water and trifluoroacetic acid as eluent, and further purified by chromatography on silica gel using a 4:1 v/v mixture of methylene chloride and isopropanol as eluent. There was thus obtained p-[N-(2,7-dimethyl-4-oxo-3,4-dihydroquinazolin-6-ylmethyl)-N-(prop-2-ynyl)amino]-N-[1-(3-nitrophenyl)-2-(1,2,4-triazol-3-ylsulphinyl)ethyl]benzamide (containing 0.75 equivalents of water and 0.7 equivalents of trifluoroacetic acid, 0.074 g).

NMR Spectrum (CD$_3$SOCD$_3$) 2.31 and 2.45 (2 s's, 6H), 3.19 (s, 1H), 3.65-4.0 (m, 2H), 4.29 (s, 2H), 4.68 (s, 2H), 5.3 and 5.6 (2m's, 1H), 7.6-8.3 (m, 8H), 8.6 and 8.9 (2 s's, 1H);

Elemental Analysis: Found C, 54.6; H, 4.6; N, 15.4; C$_{31}$H$_{28}$N$_8$O$_5$S 0.75H$_2$O 0.7CF$_3$CO$_2$H requires C, 54.2; H, 4.2; N, 15.5%.

EXAMPLE 33

Using a similar procedure to that described in Example 30, p-[N-(2,7-dimethyl-4-oxo-3,4-dihydroquinazolin-6-ylmethyl)-N-(prop-2-ynyl)amino]-N-[1-(3-nitrophenyl)-2-(1,2,4-triazol-3-ylthio)ethyl]benzamide (0.15 g) was reacted with m-chloroperbenzoic acid (0.142 g of material of 60% purity) during 6 hours to give a crude product which was purified by chromatography on reverse-phase silica gel using a 53:47:0.2 v/v mixture of methanol, water and trifluoroacetic acid as eluent. There was thus obtained p-[N-(2,7-dimethyl-4-oxo-3,4-dihydroquinazolin-6-ylmethyl)-N-(prop-2-ynyl)amino]-N-[1-(3-nitrophenyl)-2-(1,2,4-triazol-3-ylsulphonyl)ethyl]benzamide (containing 0.75 equivalents of water and 0.7 equivalents of trifluoroacetic acid, 0.065 g).

NMR Spectrum (CD$_3$SOCD$_3$) 2.30 and 2.44 (2 s's, 6H), 3.19 (s, 1H), 3.6-4.0 (m, 2H), 4.27 (s, 2H), 4.69 (s, 2H), 5.62 (m, 1H), 6.8-8.3 (m, 8H), 8.77 (s, 1H), 8.84 (d, 1H);

Mass Spectrum (Positive ion FAB): m/e (P+1) 641.

EXAMPLE 34

The following illustrate representative pharmaceutical dosage forms containing the compound of formula I, or a pharmaceutically-acceptable salt thereof (hereafter compound X), for therapeutic or prophylactic use in humans:

| | | mg/tablet |
|---|---|---|
| (a) | Tablet I | |
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 mg |
| | Lactose Ph.Eur | 488.5 |
| | Magnesium stearate | 1.5 |
| (e) | Injection I | (50 mg/ml) |
| | Compound X | 5.0% w/v |
| | 1M Sodium hydroxide solution | 15.0% v/v |
| | 0.1M Hydrochloric acid (to adjust pH to 7.6) | |
| | Polyethylene glycol 400 | 4.5% w/v |
| | Water for injection to 100% | |
| (f) | Injection II | (10 mg/ml) |
| | Compound X | 1.0% w/v |
| | Sodium phosphate BP | 3.6% w/v |
| | 0.1M Sodium hydroxide solution | 15.0% v/v |
| | Water for injection to 100% | |
| (g) | Injection III | (1 mg/ml, buffered to pH 6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

The above formulations may be obtained by conventional procedures well known in the pharmaceutical art. The tablets (a) to (c) may be enteric coated by conventional means, for example to provide a coating of cellulose acetate phthalate.

CHEMICAL FORMULAE

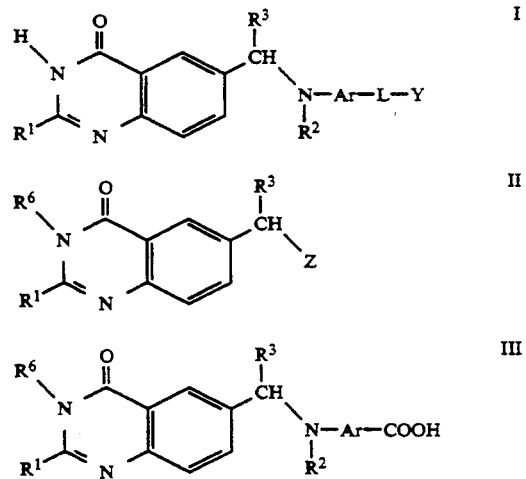

-continued
CHEMICAL FORMULAE

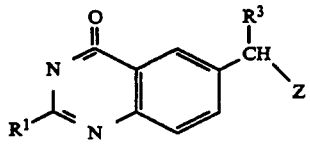

IV

What we claim is:
1. A quinazoline of the formula I

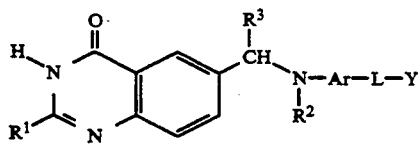

I wherein
- $R^1$ is hydrogen or amino, or alkyl or alkoxy each of up to 4 carbon atoms; or
- $R^1$ is alkyl of up to 3 carbon atoms which bears a hydroxy substituent, or which bears one, two or three fluoro substituents; or
- $R^1$ is hydroxyalkoxy of up to 3 carbon atoms or alkoxyalkoxy of up to 4 carbon atoms;
- wherein the quinazoline ring may bear no further substituent or may bear at the 5-, 7- or 8-position one further substituent selected from halogeno and from alkyl and alkoxy each of up to 3 carbon atoms;
- wherein $R^2$ is hydrogen, alkyl, alkenyl, alkynyl, hydroxyalkyl, halogenoalkyl or cyanoalkyl each of up to 4 carbon atoms;
- wherein $R^3$ is hydrogen or alkyl of up to 3 carbon atoms;
- wherein Ar is phenylene, thienylene, pyridylene, pyrimidinylene or thiazolylene which may be unsubstituted or may bear one or two substituents selected from halogeno, hydroxy, amino and nitro, and from alkyl, alkoxy and halogenoalkyl each of up to 3 carbon atoms;
- wherein L is a group of the formula —CO.NH—, —NH.CO—, —CO.$NR^4$—, —$NR^4$.CO—, —CH=CH— or —CO.O—, wherein $R^4$ is alkyl of up to 4 carbon atoms; and
- wherein Y is a group of the formula

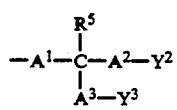

in which
- $R^5$ is hydrogen or alkyl of up to 3 carbon atoms;
- $A^1$ is a direct link or is alkylene of up to 4 carbon atoms, $A^2$ is a direct link to $Y^2$ or is alkylene of up to 4 carbon atoms, $A^2$ is a direct link to $Y^3$ or is alkylene of up to 4 carbon atoms wherein optionally a constituent methylene group is replaced by an oxy, thio, sulphinyl, sulphonyl, imino or hydroxymethylene group;
- $Y^2$ is aryl, arylthio, arylsulphinyl or arylsulphonyl each of up to 10 carbon atoms or heteroaryl, heteroarylthio, heteroarylsulphinyl or heteroarylsulphonyl; and
- $Y^3$ is hydroxy, amino, cyano, halogeno or trifluoroacetyl, or alkoxy, alkylamino, dialkylamino, halogenoalkyl, alkylthio, alkylsulphinyl, alkylsulphonyl, alkanoyloxy, alkanoyl or hydroxyalkanoyl each of up to 4 carbon atoms, or $Y^3$ is aryl, arylthio, arylsulphinyl or arylsulphonyl each of up to 10 carbon atoms, or heteroaryl, heteroarylthio, heteroarylsulphinyl or heteroarylsulphonyl, or in addition $Y^3$ is sulpho, N-hydroxycarbamoyl, N-cyanocarbamoyl, carbazoyl or sulphanoyl, or N-alkylsulphamoyl, N,N-dialkylsulphamoyl, N-acylsulphamoyl, N-alkylcarbamoyl, N,N-dialkylcarbamoyl, N-alkylcarbamoyloxy, N,N-dialkylcarbamoyloxy or N-alkylsulphonylcarbamoyl each of up to 4 carbon atoms, N-phenylsulphonylcarbamoyl or 5-tetrazolyl; and
- wherein each of said aryl, arylthio, arylsulphinyl, arylsulphonyl, heteroaryl, heteroarylthio, heteroarylsulphinyl or heteroarylsulphonyl groups may be unsubstituted or may bear one or two substituents selected from hydroxy, oxo, thioxo, amino, nitro, cyano, carbamoyl and halogeno, from alkyl, N-alkylcarbamoyl, N,N-dialkylcarbamoyl, alkylthio, alkylsulphinyl, alkylsulphonyl, alkoxy and halogenoalkyl each of up to 4 carbon atoms, and from phenyl and phenylalkyl of up to 10 carbon atoms; and
- wherein said phenyl and phenylalkyl substituents or said N-phenylsulphonylcarbamoyl group may bear a substituent selected from nitro, cyano and halogeno and from alkyl and alkoxy each of up to 3 carbon atoms;

or a pharmaceutically-acceptable salt thereof;
provided that, in the group of the formula -L-Y, no constituent methylene or methine group is attached to more than one heteroatom which is not in a heteroaryl ring.

2. A quinazoline of the formula I as claimed in claim 1 wherein
- $R^1$ is hydrogen or amino, or alkyl or alkoxy each of up to 4 carbon atoms; or
- $R^1$ is alkyl of up to 3 carbon atoms which bears a hydroxy substituent, or which bears one, two or three fluoro substituents; or
- $R^1$ is hydroxyalkoxy of up to 3 carbon atoms or alkoxyalkoxy of up to 4 carbon atoms;
- wherein the quinazoline ring may bear no further substituent or may bear at the 5-, 7- or 8-position one further substituent selected from halogeno and from alkyl and alkoxy each of up to 3 carbon atoms; wherein $R^2$ is hydrogen, alkyl, alkenyl, alkynyl, hydroxyalkyl, halogenoalkyl or cyanoalkyl each of up to 4 carbon atoms;
- wherein $R^3$ is hydrogen or alkyl of up to 3 carbon atoms;
- wherein Ar is phenylene, thienylene, pyridylene, pyrimidinylene or thiazolylene which may be unsubstituted or may bear one or two substituents selected from halogeno, hydroxy, amino and nitro, and from alkyl, alkoxy and halogenoalkyl each of up to 3 carbon atoms; wherein L is a group of the formula —CO.NH—, —NH.CO—, —CO.$NR^4$—, —$NR^4$.CO—, —CH=CH— or —CO.O—, wherein $R^4$ is alkyl of up to 4 carbon atoms; and
- wherein Y is a group of the formula

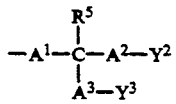

in which

R[5] is hydrogen or alkyl of up to 3 carbon atoms;

A[1] is a direct link or is alkylene of up to 4 carbon atoms, A[2] is a direct link to Y[2] or is alkylene of up to 4 carbon atoms, A[3] is a direct link to Y[3] or is alkylene of up to 4 carbon atoms;

Y[2] is aryl, arylthio, arylsulphinyl or arylsulphonyl each of up to 10 carbon atoms, or heteroaryl; and Y[3] is hydroxy, amino, cyano, halogeno or trifluoroacetyl, or alkoxy, alkylamino, dialkylamino, halogenoalkyl, alkylthio, alkylsulphinyl, alkylsulphonyl, alkanoyloxy, alkanoyl or hydroxyalkanoyl each of up to 4 carbon atoms, or Y[3] is aryl, arylthio, arylsulphinyl or arylsulphonyl each of up to 10 carbon atoms or heteroaryl, or in addition Y[3] is sulpho, N-hydroxycarbamoyl, N-cyanocarbamoyl, carbazoyl or sulphamoyl, or N-alkylsulphamoyl, N,N-dialkylsulphamoyl, N-acylsulphamoyl, N-alkylcarbamoyl, N,N-dialkylcarbamoyl, N-alkylcarbamoyloxy, N,N-dialkylcarbamoyloxy or N-alkylsulphonylcarbamoyl each of up to 4 carbon atoms, N-phenylsulphonylcarbamoyl or 5-tetrazolyl; and wherein each of said aryl, arylthio, arylsulphinyl, arylsulphonyl or heteroaryl groups may be unsubstituted or may bear one or two substituents selected from hydroxy, oxo, thioxo, amino, nitro, cyano, carbamoyl and halogeno, from alkyl, N-alkylcarbamoyl, N,N-dialkylcarbamoyl, alkylthio, alkylsulphinyl, alkylsulphonyl, alkoxy and halogenoalkyl each of up to 4 carbon atoms, and from phenyl and phenylalkyl of up to 10 carbon atoms; and wherein said phenyl and phenylalkyl substituents or said N-phenylsulphonylcarbamoyl group may bear a substituent selected from nitro, cyano and halogeno and from alkyl and alkoxy each of up to 3 carbon atoms;

or a pharmaceutically-acceptable salt thereof; provided that, in the group of the formula -L-Y, no constituent methylene or methine group is attached to more than one heteroatom which is not in a heteroaryl ring.

3. A quinazoline of the formula I as claimed in claim 1 wherein

R[1] is methyl;

wherein R[2] is methyl, ethyl or prop-2-ynyl;

wherein the quinazoline ring may bear no further substituent or may bear a 7-fluoro or 7-methyl substituent;

wherein R[3] is hydrogen;

wherein Ar is 1,4-phenylene or thien-2,5-diyl, or is thiazol-2,5-diyl with the group -L-Y in the 2-position, or is 2-fluoro-1,4-phenylene with the group -L-Y in the 1-position;

wherein L is a group of the formula —CO.NH— and wherein Y is a group of the formula

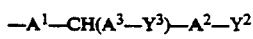

in which

A[1] is a direct link to the methine group or is methylene,

A[2] is a direct link to Y[2] or is methylene,

A[3] is a direct link to Y[3] or is methylene;

Y[2] is phenyl or phenylthio which may be unsubstituted or may bear a substituent selected from nitro, chloro, methyl, methoxy and trifluoromethyl; and Y[3] is hydroxy, cyano, acetoxy or 1,2-dihydro-2-oxopyrid-6-yl, or Y[3] is phenyl or phenylthio which may be unsubstituted or may bear a substituent selected from nitro, chloro, methyl, methoxy and trifluoromethyl, or in addition Y[3] is N-methylsulphonylcarbamoyl, N-phenylsulphonylcarbamoyl or 5-tetrazolyl; and wherein said N-phenylsulphonylcarbamoyl group may bear a substituent selected from nitro, chloro, methyl and methoxy; or a pharmaceutically-acceptable salt thereof;

provided that, in the group of the formula -L-Y, no constituent methylene or methine group is attached to more than one heteroatom.

4. A quinazoline of the formula I as claimed in claim 1 wherein

R[1] is amino or methyl;

wherein R[2] is methyl, ethyl or prop-2-ynyl;

wherein the quinazoline ring may bear no further substituent or may bear a 7-fluoro, 7-chloro, 7-bromo or 7-methyl substituent;

wherein R[3] is hydrogen;

wherein Ar is 1,4-phenylene or thien-2,5-diyl, or is thiazol-2,5-diyl with the group -L-Y in the 2-position, or is 2-fluoro-1,4-phenylene with the group -L-Y in the 1-position;

wherein L is a group of the formula —CO.NH—; and wherein Y is a group of the formula

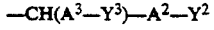

in which

A[2] is a direct link to Y[2] or is methylene;

A[3] is a direct link to Y[3] or is methylene or ethylene;

Y[2] is phenyl or 3-nitrophenyl; and

Y[3] is hydroxy, cyano, methoxy, ethoxy, tert-butoxy, dimethylamino, phenyl, 1,2,4-triazol-3-ylthio or 1,2,4-triazol-3-ylsulphinyl; or a pharmaceutically-acceptable salt thereof.

5. A quinazoline of the formula I as claimed in claim 1 wherein

R[1] is methyl;

wherein R[2] is methyl, ethyl or prop-2-ynyl;

wherein the quinazoline ring may bear no further substituent or may bear a 7-fluoro, 7-chloro, 7-bromo or 7-methyl substituent;

wherein R[3] is hydrogen;

wherein Ar is 1,4-phenylene or thien-2,5-diyl, or is thiazol-2,5-diyl with the group -L-Y in the 2-position, or is 2-fluoro-1,4-phenylene with the group -L-Y in the 1-position;

wherein L is a group of the formula —CO.NH—; and wherein Y is a group of the formula

in which

Y[2] is phenyl which may be unsubstituted or may bear a nitro substituent; and

Y[3] is N-methylsulphonylcarbamoyl, N-phenylsulphonylcarbamoyl or 5-tetrazolyl, and wherein said N-phenylsulphonylcarbamoyl group may bear a substituent selected from nitro, chloro, methyl and methoxy; or a pharmaceutically-acceptable salt thereof.

6. A quinazoline of the formula I as claimed in claim 1 wherein
$R^1$ is methyl;
wherein $R^2$ is methyl or prop-2-ynyl;
wherein the quinazoline ring may bear no further substituent or may bear a 7-fluoro, 7-bromo or 7-methyl substituent;
wherein $R^3$ is hydrogen;
wherein Ar is 1,4-phenylene or is 2-fluoro-1,4-phenylene with the group -L-Y in the 1-position;
wherein L is a group of the formula —CO.NH—; and
wherein Y is a group of the formula

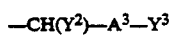
—CH(Y$^2$)—A$^3$—Y$^3$ in which
$A^3$ is methylene or ethylene;
$Y^2$ is 3-nitrophenyl; and
$Y^3$ is hydroxy;
or a pharmaceutically-acceptable salt thereof.

7. A quinazoline of the formula I as claimed in claim 1 wherein
$R^1$ is methyl;
wherein $R^2$ is prop-2-ynyl;
wherein the quinazoline ring may bear no further substituent or may bear a 7-fluoro or 7-methyl substituent;
wherein $R^3$ is hydrogen;
wherein Ar is 1,4-phenylene or is 2-fluoro-1,4-phenylene with the group -L-Y in the 1-position;
wherein L is a group of the formula —CO.NH—; and
wherein Y is a group of the formula

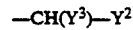
—CH(Y$^3$)—Y$^2$ in which
$Y^2$ is phenyl which may be unsubstituted or may bear a nitro substituent; and
$Y^3$ is N-methylsulphonylcarbamoyl, N-phenylsulphonylcarbamoyl, N-(4-methoxyphenylsulphonyl)carbamoyl or 5-tetrazolyl; or a pharmaceutically-acceptable salt thereof.

8. A quinazoline selected from the group of compounds:
N-[2-hydroxy-1-(3-nitrophenyl)ethyl]-p-[N-(2-methyl-4-oxo-3,4-dihydroquinazolin-6-ylmethyl)-N-(prop-2-ynyl)amino]benzamide,
p-[N-(2,7-dimethyl-4-oxo-3,4-dihydroquinazolin-6-ylmethyl)-N-(prop-2-ynyl)amino]-N-[2-hydroxy-1-(3-nitrophenyl)ethyl]benzamide,
p-[N-(2,7-dimethyl-4-oxo-3,4-dihydroquinazolin-6-ylmethyl)-N-(prop-2-ynyl)amino]-o-fluoro-N-[2-hydroxy-1-(3-nitrophenyl)ethyl]benzamide,
p-[N-(2,7-dimethyl-4-oxo-3,4-dihydroquinazolin-6-ylmethyl)-N-methylamino]-N-[2-hydroxy-1-(3-nitrophenyl)ethyl]benzamide and
p-[N-(7-bromo-2-methyl-4-oxo-3,4-dihydroquinazolin-6-ylmethyl)-N-(prop-2-ynyl)amino]-N-[2-hydroxy-1-(3-nitrophenyl)ethyl]benzamide.

9. A quinazoline selected from the group of compounds:
o-fluoro-p-[N-(2-methyl-4-oxo-3,4-dihydroquinazolin-6-ylmethyl)-N-(prop-2-ynyl)amino]-N-[3-nitro-α-(5-tetrazolyl)benzyl]benzamide,
p-[N-(2,7-dimethyl-4-oxo-3,4-dihydroquinazolin-6-ylmethyl)-N-(prop-2-ynyl)amino]-N-[3-nitro-α-(5-tetrazolyl)benzyl]benzamide,
p-[N-(7-fluoro-2-methyl-4-oxo-3,4-dihydroquinazolin-6-ylmethyl)-N-(prop-2-ynyl)amino]-N-[3-nitro-α-(5-tetrazolyl)benzyl]benzamide,
N-[p-[N-(2-methyl-4-oxo-3,4-dihydroquinazolin-6-ylmethyl)-N-(prop-2-ynyl)amino]benzoyl-(3-nitrophenyl)glycine N-(4-methoxyphenylsulphonyl)amide and
N-[p-[N-(2,7-dimethyl-4-oxo-3,4-dihydroquinazolin-6-ylmethyl)-N-(prop-2-ynyl)amino]benzoyl-(3-nitrophenyl)glycine N-(methylsulphonyl)amide.

10. A pharmaceutical composition which comprises a quinazoline as claimed in claim 1, or a pharmaceutically-acceptable salt thereof, in association which a pharmaceutically-acceptable diluent or carrier.

* * * * *